US007250272B2

(12) United States Patent
Sato et al.

(10) Patent No.: US 7,250,272 B2
(45) Date of Patent: Jul. 31, 2007

(54) G PROTEIN-COUPLED RECEPTOR PROTEIN AND DNA THEREOF

(75) Inventors: Syuji Sato, Tsukuba (JP); Yasushi Shintani, Toyonaka (JP); Nobuyuki Miyajima, Tsukuba (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 272 days.

(21) Appl. No.: 10/398,870

(22) PCT Filed: Oct. 12, 2001

(86) PCT No.: PCT/JP01/08977

§ 371 (c)(1),
(2), (4) Date: Apr. 9, 2003

(87) PCT Pub. No.: WO02/31145

PCT Pub. Date: Apr. 18, 2002

(65) Prior Publication Data

US 2004/0110920 A1 Jun. 10, 2004

(51) Int. Cl.
*C07K 14/705* (2006.01)
*C12N 15/12* (2006.01)
*G01N 33/566* (2006.01)

(52) U.S. Cl. ................. 435/69.1; 435/7.21; 435/252.3; 435/320.1; 530/350; 536/23.5

(58) Field of Classification Search ............... 435/7.21, 435/69.1, 252.3, 320.1; 530/350; 536/23.5
See application file for complete search history.

(56) References Cited

U.S. PATENT DOCUMENTS

2003/0130495 A1* 7/2003 Turner et al. .............. 536/23.5

FOREIGN PATENT DOCUMENTS

| | | |
|---|---|---|
| JP | 2001245666 | 9/2001 |
| WO | WO 01/18206 | 3/2001 |
| WO | WO 01/48015 | 7/2001 |
| WO | WO 01/48188 | 7/2001 |
| WO | WO 01/48189 | 7/2001 |

OTHER PUBLICATIONS

Mahlmann et al. "Structure, function, and phylogeny of [Arg$^8$]vasotocin receptors from teleost fish and toad" Proc. Natl. Acad. Sci USA 91:1342-1345 (Feb. 1994).
Jeffrey M. Stadel, et al., "Orphan G Protein-coupled Receptors: a Neglected Opportunity for Pioneer Drug Discovery", TiPS, (1997), pp. 430-437, vol. 18, No. 11.
Ulrik Gether, et al., "Uncovering Molecular Mechanisms Involved in Activation of G Protein-Coupled Receptors", Endocrine News, (2000), pp. 90-113, vol. 21, No. 1, XP-002169986.
Norman H. Lee, et al., "Molecular Biology of G-Protein-Coupled Receptors", Drug News and Perspectives, (1993), pp. 488-497, vol. 6, No. 7, XP 000677175.
Catherine D. Strader, et al., "Structure and Function of G Protein-Coupled Receptors", Annual Review of Biochemistry, (1994), pp. 101-132, vol. 63, XP001041816.

* cited by examiner

*Primary Examiner*—John Ulm
(74) *Attorney, Agent, or Firm*—Edwards Angell Palmer & Dodge, LLP; Gregory B. Butler, Esq.

(57) ABSTRACT

The present invention aims at providing a useful and novel G protein-coupled receptor protein and DNA thereof.

The G protein-coupled receptor protein of the present invention and the like, and the polynucleotides encoding the receptor protein and the like, are useful for; 1) determination of ligands (agonists); 2) preparation of antibodies and antisera; 3) construction of recombinant receptor protein expression systems; 4) development of the receptor binding assay systems using the expression systems and screening of pharmaceutical candidate compounds; 5) effecting drug design based on comparison with structurally similar ligand receptors; 6) reagents for preparation of probes and PCR primers for gene diagnosis; 7) production of transgenic animals; and 8) pharmaceutical drugs for the gene prophylaxis and gene therapy.

20 Claims, 15 Drawing Sheets

Fig.3

MPANFTEGSFDSSGTGQTLDSSPVACTETVTFTEVVEGKEWGSFYYSFKTEQLITLWVLFVFTIVGNSVVLFSTW

RRKKKSRMTFFVTQLAITDSFTGLVNILTDINWRFTGDFTAPDLVCRVVRYLQVVLLYASTYVLVSLSIDRYHAI

VYPMKFLQGEKQARVLIVIAWSLSFLFSIPTLIIFGKRTLSNGEVQCWALWPDDSYWTPYMTIVAFLVYFIPLTI

ISIMYGIVIRTIWIKSKTYETVISNCSDGKLCSSYNRGLISKAKIKAIKYSIIIILAFICCWSPYFLFDILDNFN

LLPDTQERFYASVIIQNLPALNSAINPLIYCVFSSSISFPCREQRSQDSRMTFRERTERHEMQILSKPEFI

Fig.4

MPANFTEGSFDSSGTGQTLDSSPVACTETVTFTEVVEGKEWGSFYYSFKTEQLITLWVLFVFTIVGNSVVLFSTW

RRKKKSRMTFFVTQLAITDSFTGLVNILTDIIWRFTGDFTAPDLVCRVVRYLQVVLLYASTYVLVSLSIDRYHAI

VYPMKFLQGEKQARVLIVIAWSLSFLFSIPTLIIFGKRTLSNGEVQCWALWPDDSYWTPYMTIVAFLVYFIPLTI

ISIMYGIVIRTIWIKSKTYETVISNCSDGKLCSSYNRGLISKAKIKAIKYSIIIILAFICCWSPYFLFDILDNFN

LLPDTQERFYASVIIQNLPALNSAINPLIYCVFSSSISFPCRERRSQDSRMTFRERTERHEMQILSKPEFI 1.6
-1.6
1
100
200
300
4.0
2.0
0.0
-2.0
-4.0

Fig.9

MPANLTEGSFHANQTVPMLDSSPVACTEIVTFTEALVAEEWGSFYSSFKTEQLITLW
VLFVVTIVGNSVVLFSTCRRKRKSRMTFFVTQLAITGDFMAPDLVCRVVRYLQVVLL
YASTYVLVSLSIDRYHAIVYPMKFLQGEKQAKVLIGIAWSLSFLFSIPTLIIFGKRTLSN
GEVQCWALWPDDSYWTPYMTIVAFLVYFIPLAIISVTYGLVIRTIWMKSKTHETVISNC
SDGKLCCSYNRGLISKAKIKAIKYSIVIILAFICCWSPYFLFDILDNFNVLPDTKERFY
ASVIIQNLPALNSAINPLIYCIFSSSICSPCKMQRSQDSRMTYRERSERHEMQILSKPE
FI 1.6
-1.6
1
100
200
300
4.0
2.0
0.0
-2.0
-4.0

Fig.11

MPANLTEGSFHANQTVPMLDSSPVACTEIVTFTEALVAEEWGSFYSSFKTEQLITLW
VLFVVTIVGNSVVLFSTCRRKRKSRMTFFVTQLAITDSFTGLINILTDIIWRFTGDFM
APDLVCRVVRYLQVVLLYASTYVLVSLSIDRYHAIVYPMKFLQGEKQAKVLIGIAWSL
SFLFSIPTLIIFGKRTLSNGEVQCWALWPDDSYWTPYMTIVAFLVYFIPLAIISVIYGLV
IRTIWMKSKTHETVISNCSDGKLCCSYNRGLISKAKIKAIKYSIVIILAFICCWSPYFLF
DILDNFNVLPDTKERFYASVIIQNLPALNSAINPLIYCIFSSSICSPCKMQRSQDSRMT
YRERSERHEMQILSKPEFI

Fig.13

```
MPANLTEGSF HANQTVPMLD SSPVACTEIV TFTEALEAEE WGSFYSSFKT EQLITLWVLF   60
VFTIVGNSVV LFSTWRRKRK SRMTFFVTQL AITDSFTGLI NILTDIIWRF TGDFMAPDLV  120
CRIVRYLQVV LLYASTYVLV SLSIDRYHAI VYPMKFLQGE KQAKVLIGIA WSLSFLFSIP  180
TLIIFGKRTL SNGEVQCWAL WPDDSYWTPY MTIVAFLVYF IPLTIISVIY GLVIRTIWIK  240
SKAHETVISN CSDGELCCSY NRGLISKAKI KAIKYSIVII LAFICCWSPY FLFDMLDNFN  300
LLPDTKERFY ASVIIQNLPA LNSAINPLIY CIFSGSLCSP CKVQRSQDSR MTYRERSERH  360
EMQILSKPEF I                                                       371
```

G PROTEIN-COUPLED RECEPTOR PROTEIN AND DNA THEREOF

This application is the National Phase filing of International Patent Application No. PCT/JP01/08977, filed 12 Oct. 2001.

FIELD OF THE INVENTION

The present invention relates to a novel G protein-coupled receptor protein derived from human colon cancer, or its salts and DNA encoding the same.

BACKGROUND ART

Physiological active substances such as various hormones and neurotransmitters regulate the biological function via specific receptor proteins present on cell membranes. Many of these receptor proteins are coupled with guanine nucleotide-binding protein (hereinafter sometimes simply referred to as G protein) and mediate the intracellular signal transduction via activation of G protein. These receptor proteins possess the common structure containing seven transmembrane domains and are thus collectively referred to as G protein-coupled receptors or seven-transmembrane receptors (7TMR).

G protein-coupled receptor proteins present on the cell surface of each functional cell and organ in the body, and play important physiological roles as the target of the molecules that regulate the functions of the cells and organs, e.g., hormones, neurotransmitters, physiologically active substances and the like. Receptors transmit signals to cells via binding with physiologically active substances, and the signals induce various reactions such as activation and inhibition of the cells.

To clarify the relationship between substances that regulate complex biological functions in various cells and organs, and their specific receptor proteins, in particular, G protein-coupled receptor proteins, would elucidate the functional mechanisms in various cells and organs in the body to provide a very important means for development of drugs closely associated with the functions.

For example, in various organs, their physiological functions are controlled in vivo through regulation by many hormones, hormone-like substances, neurotransmitters or physiologically active substances. In particular, physiologically active substances are found in numerous sites of the body and regulate the physiological functions through their corresponding receptor proteins. However, it is supposed that many unknown hormones, neurotransmitters or many other physiologically active substances still exist in the body and, as to their receptor proteins, many of these proteins have not yet been reported. In addition, it is still unknown if there are subtypes of known receptor proteins.

It is very important for development of drugs to clarify the relationship between substances that regulate elaborated functions in vivo and their specific receptor proteins. Furthermore, for efficient screening of agonists and antagonists to receptor proteins in development of drugs, it is required to clarify functional mechanisms of receptor protein genes expressed in vivo and express the genes in an appropriate expression system.

In recent years, random analysis of cDNA sequences has been actively studied as a means for analyzing genes expressed in vivo. The sequences of cDNA fragments thus obtained have been registered on and published to databases as Expressed Sequence Tag (EST). However, since many ESTs contain sequence information only, it is difficult to predict their functions from the information.

Substances that inhibit binding between G protein-coupled proteins and physiologically active substances (i.e., ligands) and substances that bind and induce signals similar to those induced by physiologically active substances (i.e., ligands) have been used as pharmaceuticals, as antagonists and agonists specific to the receptors, that regulate the biological functions. Therefore, discovery and gene cloning (e.g., cDNA) of a novel G protein-coupled receptor that can be targeted for pharmaceutical development are very important means in search for a specific ligand, agonist, and antagonist of the novel G protein-coupled receptor.

However, not all G protein-coupled receptors have been discovered. There are unknown G protein-coupled receptors and many of these receptors in which the corresponding ligands are yet unidentified are called orphan receptors. Therefore, search and functional elucidation of a novel G protein-coupled receptor is awaited.

G protein-coupled receptors are useful in searching for a novel physiological active substance (i.e., ligand) using the signal transduction activity as the index and in search for agonists and antagonists of the receptor. Even if no physiological ligand is found, agonists and antagonist of the receptor may be prepared by analyzing the physiological action of the receptor through inactivation experiment of the receptor (knockout animal). Ligands, agonists, antagonists, etc. of the receptor are expected to be used as prophylactic/therapeutic and diagnostic agents for diseases associated with dysfunction of the G protein-coupled receptor.

Lowering or accentuation in functions of the G protein coupled receptor due to genetic aberration of the receptor in vivo causes some disorders in many cases. In this case, the G protein coupled receptor may be used not only for administration of antagonists or agonists of the receptor, but also for gene therapy by transfer of the receptor gene into the body (or some specific organs) or by introduction of the antisense nucleic acid of the receptor gene into the body (or the specific organ). In the gene therapy, information on the base sequence of the receptor gene is essentially required for investigating deletion or mutation in the gene. The receptor gene is also applicable as prophylactic/therapeutic and diagnostic agents for diseases associated with dysfunction of the receptor.

The present invention provides a novel and useful G protein-coupled receptor protein as described above. That is, the present invention provides a novel G protein-coupled receptor protein, its partial peptides and salts thereof, as well as polynucleotides (DNA and RNA, and derivatives thereof) containing the polynucleotides (DNA and RNA, and derivatives thereof) encoding the G protein-coupled receptor protein or its partial peptides, recombinant vectors containing the polynucleotides, transformants bearing the recombinant vectors, methods for manufacturing the G protein-coupled receptor protein or its salts, antibodies to the G protein-coupled receptor protein, its partial peptides and salts thereof, compounds that alter the expression level of said G protein-coupled receptor protein, methods for determination of ligands to the G protein-coupled receptor protein, methods for screening the compounds (antagonists and agonists) or salts thereof that alter the binding property of ligands and the G protein-coupled receptor protein, kits for use in the screening methods, compounds (antagonists and agonists) or salts thereof that alter the binding property of ligands obtainable by the screening methods or obtainable using the screening kits and the G protein-coupled receptor protein, and pharmaceutical compositions comprising the compounds (antagonists and agonists) that alter the binding property of ligands to the G protein-coupled receptor protein, or compounds or salts thereof that alter the expression level of the G protein-coupled receptor protein.

DISCLOSURE OF THE INVENTION

As a result of extensive investigations, the present inventors have succeeded in isolating cDNAs encoding novel G protein-coupled receptor proteins derived from human colon cancer, and in sequencing the full-length base sequences. When the base sequences were translated into the amino acid sequences, 1 to 7 transmembrane domains were found to be on the hydrophobic plot, establishing that the proteins encoded by these cDNAs are seven-transmembrane type G protein-coupled receptor proteins. In addition, the inventors acquired mouse homologues. Based on these findings, the present inventors have continued further extensive studies and as a result, have come to accomplish the present invention.

Thus, the present invention relates to the following features.

(1) A G protein-coupled receptor protein containing the same or substantially the same amino acid sequence as the amino acid sequence represented by SEQ ID NO: 1 or SEQ ID NO: 3, or a salt thereof.

(2) A G protein-coupled receptor protein having an amino acid sequence represented by SEQ ID NO: 1 according to (1), or a salt thereof.

(3) A G protein-coupled receptor protein having an amino acid sequence represented by SEQ ID NO: 3 according to (1), or a salt thereof.

(4) A G protein-coupled receptor protein containing the same or substantially the same amino acid sequence as the amino acid sequence represented by SEQ ID NO: 10 or SEQ ID NO: 14, or a salt thereof.

(5) A G protein-coupled receptor protein having an amino acid sequence represented by SEQ ID NO: 10 according to (4), or a salt thereof.

(6) A G protein-coupled receptor protein having an amino acid sequence represented by SEQ ID NO: 14 according to (4), or a salt thereof.

(7) A G protein-coupled receptor protein containing the same or substantially the same amino acid sequence as the amino acid sequence represented by SEQ ID NO: 64, or a salt thereof.

(8) A G protein-coupled receptor protein having an amino acid sequence represented by SEQ ID NO: 64 according to (7), or a salt thereof.

(9) A partial peptide of the G protein-coupled receptor protein according to (1), (4) or (7), or a salt thereof.

(10) A polynucleotide containing a polynucleotide encoding the G protein-coupled protein according to (1), (4) or (7).

(11) A polynucleotide according to (10), which is DNA.

(12) A DNA according to (11), which is represented by SEQ ID NO: 2, SEQ ID NO: 4, SEQ ID NO: 11, SEQ ID NO: 15 or SEQ ID NO: 65.

(13) A recombinant vector containing the polynucleotide according to (10).

(14) A transformant transformed with the recombinant vector according to (13).

(15) A method of manufacturing the G protein-coupled receptor protein or its salt according to (1), (4) or (7), which comprises culturing the transformant according to (14) and producing the G protein-coupled receptor protein according to (1), (4) or (7).

(16) An antibody to the G protein-coupled receptor protein according to (1), (4) or (7), the partial peptide according to (9), or a salt of said protein or partial peptide.

(17) An antibody according to (16), which is a neutralizing antibody capable of inactivating signal transduction of the G protein-coupled receptor protein according to (1), (4) or (7).

(18) An antibody according to (16), which is a neutralizing antibody capable of activating signal transduction of the G protein-coupled receptor protein according to (1), (4) or (7).

(19) A diagnostic product comprising an antibody according to (16).

(20) A drug comprising an antibody according to (16).

(21) A ligand to the G protein-coupled receptor protein according to (1), (4) or (7), or a salt thereof, which is obtainable using the G protein-coupled receptor protein according to (1), (4) or (7), or the partial peptide or salts thereof.

(22) A drug comprising the ligand to the G protein-coupled receptor according to (21).

(23) A method of determining a ligand to the G protein-coupled receptor protein according to (1), (4) or (7), or its salt, which comprises using the G protein-coupled receptor protein according to (1), (4) or (7), or the partial peptide, or salts thereof.

(24) A method of screening a compound that alters the binding property between a ligand and the G protein-coupled receptor protein according to (1), (4) or (7), or its salt, which comprises using the G protein-coupled receptor protein according to (1), (4) or (7), or the partial peptide, or salts thereof.

(25) A kit of screening a compound that alters the binding property between a ligand and the G protein-coupled receptor protein according to (1), (4) or (7), or its salt, which comprises using the G protein-coupled receptor protein according to (1), (4) or (7), or the partial peptide, or salts thereof.

(26) A compound or its salt that alters the binding property between a ligand and the G protein-coupled receptor protein according to (1), (4) or (7), or its salt, which is obtainable using the screening method according to (24) or the screening kit according to (25).

(27) A drug comprising the compound or salt thereof according to (26).

(28) A polynucleotide that hybridizes to the polynucleotide according to (10) under a highly stringent condition.

(29) An antipolynucleotide comprising a base sequence complementary to the polynucleotide according to (10) or a part of the base sequence.

(30) A method of quantifying mRNA of the G protein-coupled receptor protein according to (1), (4) or (7), which comprises using the polynucleotide according to (10) or a part of the polynucleotide.

(31) A method of quantifying the G protein-coupled receptor protein according to (1), (4) or (7), which comprises using the antibody according to (16).

(32) A diagnostic method for a disease associated with functions of the G protein-coupled receptor protein according to (1), (4) or (7), which comprises using the quantification method according to (30) or (31).

(33) A method of screening a compound or its salt that alters the expression level of the G protein-coupled receptor protein according to (1), (4) or (7), which comprises using the quantification method according to (30).

(34) A method of screening a compound or its salt that alters the amount of the G protein-coupled receptor protein according to (1), (4) or (7) in cell membrane, which comprises using the quantification method according to (30).

(35) A compound or its salt that alters the expression level of the G protein-coupled receptor protein according to (1), (4) or (7), which is obtainable using the screening method according to (33).

(36) A compound or its salt that alters the amount of the G protein-coupled receptor protein according to (1), (4) or (7) in cell membrane, which is obtainable using the screening method according to (34).

(37) A drug comprising the compound or salt thereof according to (35).

(38) A drug comprising the compound or salt thereof according to (36).

(39) The drug according to (27), (37) or (38), which is a prophylactic and/or therapeutic agent for central nervous diseases, endocrine diseases, metabolic diseases or cancer.

(40) A preventive and/or therapeutic method for central nervous diseases, endocrine diseases, metabolic diseases or cancer, which comprises administering an effective amount of the compound according to (26), (35) or (36), or its salt to mammals.

(41) Use of the compound according to (26), (35) or (36), or its salt for manufacturing a prophylactic and/or therapeutic agent for central nervous diseases, endocrine diseases, metabolic diseases or cancer.

(42) A diagnostic product comprising a polynucleotide containing a polynucleotide, which encodes the G protein coupled receptor protein according to (1).

(43) A diagnostic product, which comprises combining a polynucleotide containing a polynucleotide containing a base sequence represented by SEQ ID NO: 2 and a polynucleotide containing a base sequence represented by SEQ ID NO: 4.

(44) A diagnostic product, which comprises combining (i) a polynucleotide encoding the G protein coupled receptor protein according to (1) and (ii) a polynucleotide encoding a G protein coupled receptor protein having an amino acid sequence represented by SEQ ID NO: 16, or a polynucleotide encoding a G protein coupled receptor protein having an amino acid sequence represented by SEQ ID NO: 18.

(45) The diagnostic product according to (42) to (44), which is a diagnostic product for central nervous diseases, endocrine diseases, metabolic diseases or cancer.

(46) A diagnostic method, which comprises measuring an expression level of the G protein coupled receptor protein according to (1), or its salt by using a polynucleotide containing a polynucleotide encoding the G protein coupled receptor protein according to (1).

(47) A diagnostic method, which comprises measuring an expression level of the G protein coupled receptor protein containing an amino acid sequence represented by SEQ ID NO: 1, or its salt, and the G protein coupled receptor protein containing an amino acid sequence represented by SEQ ID NO: 3, or its salt, by using a polynucleotide containing a polynucleotide containing a base sequence represented by SEQ ID NO: 2, and a polynucleotide containing a polynucleotide containing a base sequence represented by SEQ ID NO: 4.

(48) A diagnostic method, which comprises measuring an expression level of (i) the G protein coupled receptor protein containing an amino acid sequence represented by SEQ ID NO: 1, or its salt, and (ii) the G protein coupled receptor protein containing an amino acid sequence represented by SEQ ID NO: 16, or its salt, or the G protein coupled receptor protein containing an amino acid sequence represented by SEQ ID NO: 18, or its salt, by using (i) a polynucleotide containing a polynucleotide containing a base sequence represented by SEQ ID NO: 2, and (ii) a polynucleotide containing a polynucleotide containing a base sequence represented by SEQ ID NO: 17, or a polynucleotide containing a polynucleotide containing a base sequence represented by SEQ ID NO: 19.

(49) A diagnostic method, which comprises measuring an expression level of (i) the G protein coupled receptor protein containing an amino acid sequence represented by SEQ ID NO: 3, or its salt, and (ii) the G protein coupled receptor protein containing an amino acid sequence represented by SEQ ID NO: 16, or its salt, or the G protein coupled receptor protein containing an amino acid sequence represented by SEQ ID NO: 18, or its salt, by using (i) a polynucleotide containing a polynucleotide containing a base sequence represented by SEQ ID NO: 4, and (ii) a polynucleotide containing a polynucleotide containing a base sequence represented by SEQ ID NO: 17, or a polynucleotide containing a polynucleotide containing a base sequence represented by SEQ ID NO: 19.

(50) The diagnostic method according to (46) to (49), which is a diagnostic method for central nervous diseases, endocrine diseases, metabolic diseases or cancer.

(51) A non-human transgenic animal having a DNA encoding the G protein coupled receptor protein according to (1), (4) or (7), or its mutated DNA.

(52) The animal according to (51), wherein the non-human animal is a rodent.

(53) The animal according to (52), wherein the rodent is mouse or rat.

(54) A recombinant vector, which contains a foreign DNA encoding the G protein coupled receptor protein according to (1), (4) or (7), or its mutated DNA, and expresses in non-human animal.

(55) A non-human mammalian embryonic stem cell, wherein the DNA encoding the G protein coupled receptor protein according to (1), (4) or (7) is inactivated.

(56) The embryonic stem cell according to (55), wherein the non-human mammal is a rodent.

(57) The embryonic stem cell according to (56), wherein the rodent is mouse.

(58) A non-human mammal, which is insufficient for DNA expression, wherein the DNA encoding the G protein coupled receptor protein according to (1), (4) or (7) is inactivated.

(59) The non-human mammal according to (58), wherein the non-human mammal is a rodent.

(60) The non-human mammal according to (59), wherein the rodent is mouse.

The present invention further relates to the following features.

(61) A G protein-coupled receptor protein or its salt according to (1), wherein said protein contains (i) the amino acid sequence shown by SEQ ID NO: 1 or SEQ ID NO: 3, of which at least 1 or 2 (preferably approximately 1 to 30, more preferably approximately 1 to 10, most preferably several (1 to 5)) amino acids are deleted, (ii) the amino acid sequence shown by SEQ ID NO: 1 or SEQ ID NO: 3, to which at least 1 or 2 (preferably approximately 1 to 30, more preferably approximately 1 to 10, most preferably several (1 to 5)) amino acids are added; (iii) the amino acid sequence shown by SEQ ID NO: 1 or SEQ ID NO: 3, in which at least 1 or 2 (preferably approximately 1 to 30, more preferably approximately 1 to 10, most preferably several (1 to 5)) amino acids are substituted; or (iv) the amino acid sequence containing a combination of these amino acid sequences.

(62) A G protein-coupled receptor protein or its salt according to (4), wherein said protein contains (i) the amino acid sequence shown by SEQ ID NO: 10 or SEQ ID NO: 14, of which at least 1 or 2 (preferably approximately 1 to 30, more preferably approximately 1 to 10, most preferably several (1 to 5)) amino acids are deleted, (ii) the amino acid sequence shown by SEQ ID NO: 10 or SEQ ID NO: 14, to which at least 1 or 2 (preferably approximately 1 to 30, more preferably approximately 1 to 10, most preferably several (1 to 5)) amino acids are added; (iii) the amino acid sequence shown by SEQ ID NO: 10 or SEQ ID NO: 14, in which at least 1 or 2 (preferably approximately 1 to 30, more preferably approximately 1 to 10, most preferably several (1 to 5)) amino acids are substituted; or (iv) the amino acid sequence containing a combination of these amino acid sequences.

(63) A G protein-coupled receptor protein or its salt according to (7), wherein said protein contains (i) the amino acid sequence shown by SEQ ID NO: 64, of which at least 1 or 2 (preferably approximately 1 to 30, more preferably approximately 1 to 10, most preferably several (1 to 5)) amino acids are deleted, (ii) the amino acid sequence shown by SEQ ID NO: 64, to which at least 1 or 2 (preferably approximately 1 to 30, more preferably approximately 1 to 10, most preferably several (1 to 5)) amino acids are added; (iii) the amino acid sequence shown by SEQ ID NO: 64, in which at least 1 or 2 (preferably approximately 1 to 30, more preferably approximately 1 to 10, most preferably several (1 to 5)) amino acids are substituted; or (iv) the amino acid sequence containing a combination of these amino acid sequences.

(64) A method of determining a ligand according to (21), which comprises contacting the G protein-coupled receptor protein according to (1), (4) or (7), or its salt, or the partial peptide or its salt with a test compound.

(65) A method of determining a ligand according to (63), in which said ligand is, for example, angiotensin, bombesin, canavinoid, cholecystokinin, glutamine, serotonin, melatonin, neuropeptide Y, an opioid, a purine, vasopressin, oxytocin, PACAP (e.g., PACAP27, PACAP38), secretin, glucagon, calcitnonin, adrenomedulin, somatostatin, GHRH, CRF, ACTH, GRP, PTH, vasoactive intestinal and related polypeptide (VIP), somatostatin, dopamine, motilin, amylin, bradykinin, calcitonin gene-related peptide (CGRP), a leukotriene, pancreastatin, a prostaglandin, thromboxane, adenosine, adrenaline, a chemokine superfamily (e.g., IL-8, GROα, GROβ, GROγ, NAP-2, ENA-78, GCP-2, PF4, IP10, Mig, CXC chemokine subfamily such as PBSF/SDF-1, etc.; CC chemokine subfamily such as MCAF/MCP-1, MCP-2, MCP-3, MCP-4, eotaxin, RANTES, MIP1-α, MIP-1β, HCC-1, MIP-3α/LARC, MIP-3β/ELC, I-309, TARC, MIPF-1, MIPF-2/eotaxin-2, MDC, DC-CK1/PARC, SLC, etc.; C chemokine subfamily such as lymphotactin; CX3C chemokine subfamily such as fractalkine, etc., etc.), endothelin, enterogastrin, histamine, neurotensin, TRH, pancreatic polypeptide, galanin, lysophosphatidic acid (LPA) or sphingosine 1-phosphate.

(66) A method of screening according to (24), in which (i) contact of a ligand with the G protein-coupled receptor protein according to (1), (4) or (7), or its salt, or the partial peptide or its salt is compared with (ii) contact of the ligand and a test compound with the G protein-coupled receptor protein according to (1), (4) or (7), or its salt, or the partial peptide or its salt.

(67) A method of screening a compound or its salt that alters the binding property between a ligand and the G protein-coupled receptor protein according to (1), (4) or (7), or its salt, which comprises measuring the amounts of a labeled ligand bound to the G protein-coupled receptor protein according to (1), (4) or (7), or its salt, or to the partial peptide or its salt, (i) when the labeled ligand is brought in contact with the G protein-coupled receptor protein according to (1), (4) or (7), or its salt, or with the partial peptide or its salt, and (ii) when the labeled ligand and a test compound are brought in contact with the G protein-coupled receptor protein according to (1), (4) or (7), or its salt, or with the partial peptide or its salt; and comparing the amounts measured in (i) and (ii).

(68) A method of screening a compound or its salt that alters the binding property between a ligand and the G protein-coupled receptor protein according to (1), (4) or (7), or its salt, which comprises measuring the amounts of a labeled ligand bound to a cell containing the G protein-coupled receptor protein according to (1), (4) or (7), (i) when the labeled ligand is brought in contact with the cell containing the G protein-coupled receptor protein according to (1), (4) or (7), and (ii) when the labeled ligand and a test compound are brought in contact with the cell containing the G protein-coupled receptor protein according to (1), (4) or (7); and comparing the amounts measured in (i) and (ii).

(69) A method of screening a compound or its salt that alters the binding property between a ligand and the G protein-coupled receptor protein according to (1), (4) or (7), or its salt, which comprises measuring the amounts of a labeled ligand bound to a cell membrane fraction containing the G protein-coupled receptor protein according to (1), (4) or (7), (i) when the labeled ligand is brought in contact with the cell membrane fraction, and (ii) when the labeled ligand and a test compound are brought in contact with the cell membrane fraction; and comparing the amounts measured in (i) and (ii).

(70) A method of screening a compound or its salt that alters the binding property between a ligand and the G protein-coupled receptor protein according to (1), (4) or (7), or its salt, which comprises measuring the amounts of a labeled ligand bound to a G protein-coupled receptor protein expressed in a cell membrane, (i) when the labeled ligand is brought in contact with the G protein-coupled receptor protein expressed in a cell membrane of the transformant according to (14) by culturing the transformant and (ii) when the labeled ligand and a test compound are brought in contact with the G protein-coupled receptor protein expressed in a cell membrane of the transformant according to (14) by culturing the transformant; and comparing the amounts measured in (i) and (ii).

(71) A method of screening a compound or its salt that alters the binding property between a ligand and the G protein-coupled receptor protein according to (1), (4) or (7), or its salt, which comprises measuring the G protein-coupled receptor protein-mediated cell stimulating activities, (i) when a compound that activates the G protein-coupled receptor protein according to (1), (4) or (7), or its salt is brought in contact with a cell containing the G protein-coupled receptor protein according to (1), (4) or (7), and (ii) when a compound that activates the G protein-coupled receptor protein according to (1), (4) or (7), or its salt and a test compound are brought in contact with a cell containing the G protein-coupled receptor protein according to (1), (4) or (7); and comparing the activities measured in (i) and (ii).

(72) A method of screening a compound or its salt that alters the binding property between a ligand and the G protein-coupled receptor protein according to (1), (4) or (7), or its salt, which comprises measuring the G protein-coupled receptor protein-mediated cell stimulating activities, when a compound that activates the G protein-coupled receptor protein according to (1), (4) or (7), or its salt is brought in contact with a G protein-coupled receptor protein expressed in a cell membrane of the transformant according to (14) by culturing the transformant, and when the compound that activates the G protein-coupled receptor protein according to (1), (4) or (7), or its salt and a test compound are brought in contact with the G protein-coupled receptor protein expressed in a cell membrane of the transformant according to (14) by culturing the transformant; and comparing the protein-mediated activities measured in (i) and (ii).

(73) A method of screening according to (71) or (72), in which said compound that activates the protein according to (1), (4) or (7) is angiotensin, bombesin, canavinoid, cholecystokinin, glutamine, serotonin, melatonin, neuropeptide Y, an opioid, a purine, vasopressin, oxytocin, PACAP (e.g., PACAP27, PACAP38), secretin, glucagon, calcitnonin, adrenomedulin, somatostatin, GHRH, CRF, ACTH, GRP, PTH, vasoactive intestinal and related polypeptide (VIP), somatostatin, dopamine, motilin, amylin, bradykinin, calcitonin gene-related peptide (CGRP), a leukotriene, pancreastatin, a prostaglandin, thromboxane, adenosine, adrenaline, a chemokine superfamily (e.g., IL-8, GROα, GROβ, GROγ, NAP-2, ENA-78, GCP-2, PF4, IP10, Mig, CXC chemokine subfamily such as PBSF/SDF-1, etc.; CC chemokine subfamily such as MCAF/MCP-1, MCP-2, MCP-3, MCP-4, eotaxin, RANTES, MIP1-α, MIP-1 β, HCC-1, MIP-3α/LARC, MIP-3β/ELC, 1-309, TARC, MIPF-1, MIPF-2/eotaxin-2, MDC, DC-CK1/PARC, SLC, etc.; C chemokine subfamily such as lymphotactin; CX3C chemokine subfamily such as fractalkine, etc.), endothelin, enterogastrin, histamine, neurotensin, TRH, pancreatic polypeptide, galanin, lysophosphatidic acid (LPA) or sphingosine 1-phosphate.

(74) A compound or its salt that alters the binding property between a ligand and the G protein-coupled receptor protein according to (1), (4) or (7), or its salt, which is obtainable by the screening methods according to (33) through (40).

(75) A drug comprising a compound or its salt that alters the binding property between a ligand and the G protein-coupled receptor protein according to (1), (4) or (7), or its salt, which is obtainable by the screening methods according to (66) through (73).

(76) A kit for screening according to (25), comprising a cell containing the G protein-coupled receptor protein according to (1), (4) or (7).

(77) A screening kit according to (25), comprising a cell membrane fraction containing the G protein-coupled receptor protein according to (1), (4) or (7).

(78) A screening kit according to (25), comprising a G protein-coupled receptor protein expressed on the cell membrane of the transformant according to (14) by culturing the transformant.

(79) A compound or its salt that alters the binding property of a ligand and the G protein-coupled receptor protein according to (1), (4) or (7), or its salt, which is obtainable using the screening kits according to (76) through (78).

(80) A drug comprising a compound or its salt that alters the binding property of a ligand compound or its salt that alters the binding property between a ligand and the G protein-coupled receptor protein according to (1), (4) or (7), or its salt, which is obtainable using the screening kits according to (76) through (78).

(81) A method of quantifying the G protein-coupled receptor protein according to (1), (4) or (7), the partial peptide, or a salt thereof, which comprises contacting the antibody according to (16) with the G protein-coupled receptor protein according to (1), (4) or (7), the partial peptide, or a salt thereof.

(82) A method of quantifying the G protein-coupled receptor protein according to (1), (4) or (7), the partial peptide or salts thereof in a test fluid, which comprises competitively reacting the antibody according to (16) with a test fluid and a labeled form of the G protein-coupled receptor protein according to (1), (4) or (7), the partial peptide or salts thereof; and measuring the ratios bound to the antibody of the labeled form of the G protein-coupled receptor protein according to (1), (4) or (7), the partial peptide or salts thereof.

(83) A method of quantifying the G protein-coupled receptor protein according to (1), (4) or (7), the partial peptide, or salts thereof in a test fluid, which comprises reacting a test fluid simultaneously or sequentially with the antibody according to (16) immobilized on a carrier and the labeled antibody according to (16), and then measuring the activity of the label on the immobilizing carrier.

BRIEF DESCRIPTION OF THE DRAWINGS

FIG. 3 shows an amino acid sequence of TGR23-1 represented by single letter symbols. (SEQ ID NO.: 1)

FIG. 4 shows an amino acid sequence of TGR23-2 represented by single letter symbols. (SEQ ID NO.: 3)

FIG. 9 shows an amino acid sequence of mouse TGR23-1 represented by single letter symbols.

FIG. 11 shows an amino acid sequence of mouse TGR23-B represented by single letter symbols.

FIG. 13 shows an amino acid sequence of rat TGR23 represented by single letter symbols.

BEST MODE FOR CARRYING OUT THE INVENTION

Figure 1:
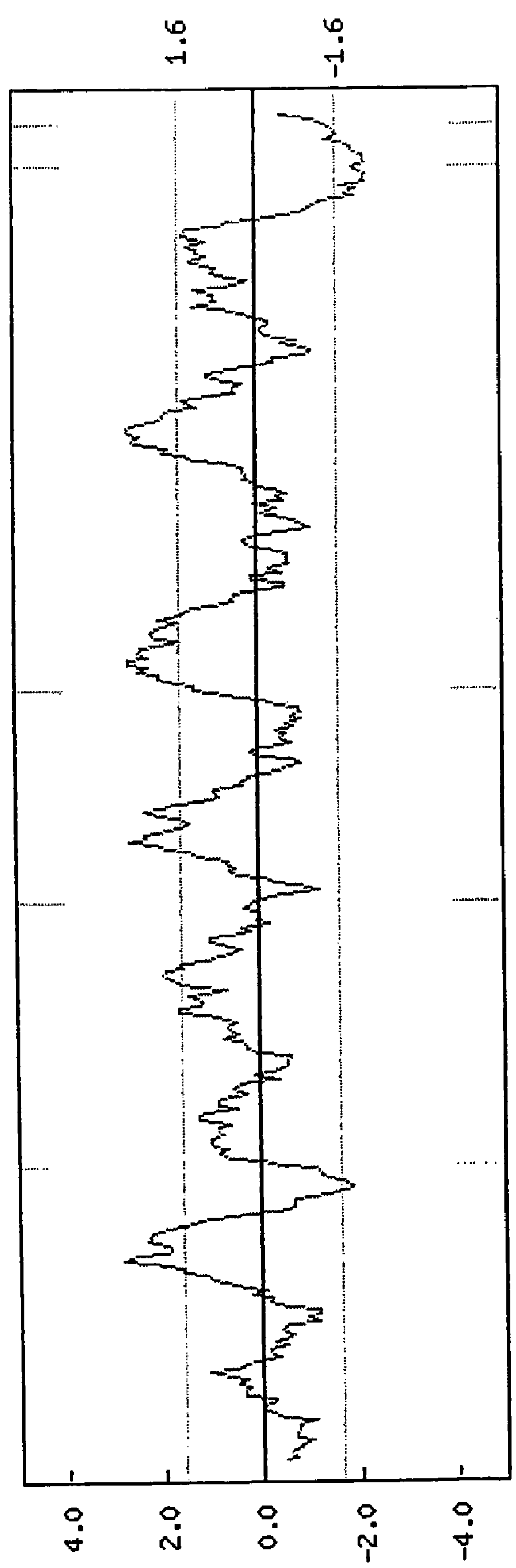
FIG. 1 shows a hydrophobicity plot of TGR23-1.

The G protein-coupled receptor protein of the present invention (hereinafter sometimes merely referred to as the receptor protein) is (1) a receptor protein, which contains the same or substantially the same amino acid sequence as the amino acid sequence shown by SEQ ID NO: 1 or SEQ ID NO: 3, (2) a receptor protein, which contains the same or substantially the same amino acid sequence as the amino acid sequence shown by SEQ ID NO: 10 or SEQ ID NO: 14, and (3) a receptor protein, which contains the same or substantially the same amino acid sequence as the amino acid sequence shown by SEQ ID NO: 64.

The receptor protein of the present invention may be any protein derived from any cells (e.g., retina cells, splenocytes, nerve cells, glial cells, β cells of pancreas, bone marrow cells, mesangial cells, Langerhans' cells, epidermic cells, epithelial cells, endothelial cells, fibroblasts, fibrocytes, myocytes, fat cells, immune cells (e.g., macrophage, T cells, B cells, natural killer cells, mast cells, neutrophil, basophil, eosinophil, monocyte, leukocytes), megakaryocyte, synovial cells, chondrocytes, bone cells, osteoblasts, osteoclasts, mammary gland cells, hepatocytes or interstitial cells, the corresponding precursor cells, stem cells, cancer cells (e.g., breast cancer cell lines (GI-101), colon cancer cell lines (CX-1, GI-112), lung cancer cell lines (LX-1, GI-117), ovarian cancer cell lines (GI-102), prostate cancer cell lines, etc.), etc.), or any tissues where such cells are present, e.g., brain or any region of the brain (e.g., olfactory bulb, amygdaloid nucleus, basal ganglia, hippocampus, thalamus, hypothalamus, subthalamic nucleus, cerebral cortex, medulla oblongata, cerebellum, occipital pole, frontal lobe, temporal lobe, putamen, caudate nucleus, corpus callosum, substantia nigra), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, peripheral blood cells, prostate, testis, ovary, placenta, uterus, bone, joint, skeletal muscle, etc., or hemocyte type cells or their cultured cells (e.g., MEL, M1, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01, etc.), from human and other mammals (e.g., guinea pigs, rats, mice, rabbits, swine, sheep, bovine, monkeys, etc.). The receptor protein may also be a synthetic protein.

The amino acid sequence which has substantially the same amino acid sequence as that represented by SEQ ID NO: 1 or SEQ ID NO: 3 includes an amino acid sequence having at least about 50% homology, preferably at least about 60% homology, more preferably at least about 70% homology, much more preferably at least about 80% homology, among others preferably at least about 90% homology and most preferably at least about 95% homology, to the amino acid sequence represented by SEQ ID NO: 1 or SEQ ID NO: 3.

Examples of the protein which contains substantially the same amino acid sequence as that shown by SEQ ID NO: 1 or SEQ ID NO: 3 include a protein having substantially the same amino acid sequence as that shown by SEQ ID NO: 1 or SEQ ID NO: 3 and having the activity substantially equivalent to the amino acid sequence represented by SEQ ID NO: 1 or SEQ ID NO: 3, etc.

Examples of the substantially equivalent activity include a ligand binding activity, a signal transduction activity, etc. The term "substantially equivalent" is used to mean that the nature of the activity is the same. Therefore, although it is preferred that activities such as the ligand binding and signal transduction activities, etc. be equivalent (e.g., about 0.01- to about 100-fold, preferably about 0.5- to about 20-fold, more preferably about 0.5- to about 2-fold), quantitative factors such as a level of the activity, a molecular weight of the protein, etc. may differ.

The amino acid sequence which has substantially the same amino acid sequence as that represented by SEQ ID NO: 10 or SEQ ID NO: 14 includes an amino acid sequence having at least about 50% homology, preferably at least about 60% homology, more preferably at least about 70% homology, much more preferably at least about 80% homology, among others preferably at least about 90% homology and most preferably at least about 95% homology, to the amino acid sequence represented by SEQ ID NO: 10 or SEQ ID NO: 14.

Examples of the protein which contains substantially the same amino acid sequence as that shown by SEQ ID NO: 10 or SEQ ID NO: 14 include a protein having substantially the same amino acid sequence as that shown by SEQ ID NO: 10 or SEQ ID NO: 14 and having the activity substantially equivalent to the amino acid sequence represented by SEQ ID NO: 10 or SEQ ID NO: 14, etc.

Examples of the substantially equivalent activity include a ligand binding activity, a signal transduction activity, etc. The term "substantially equivalent" is used to mean that the nature of the activity is the same. Therefore, although it is preferred that activities such as the ligand binding and signal transduction activities, etc. be equivalent (e.g., about 0.01- to about 100-fold, preferably about 0.5- to about 20-fold, more preferably about 0.5- to about 2-fold), quantitative factors such as a level of the activity, a molecular weight of the protein, etc. may differ.

The amino acid sequence which has substantially the same amino acid sequence as that represented by SEQ ID NO: 64 includes an amino acid sequence having at least about 50% homology, preferably at least about 60% homology, more preferably at least about 70% homology, much more preferably at least about 80% homology, among others preferably at least about 90% homology and most preferably at least about 95% homology, to the amino acid sequence represented by SEQ ID NO: 64.

Examples of the protein which contains substantially the same amino acid sequence as that shown by SEQ ID NO: 64 include a protein having substantially the same amino acid sequence as that shown by SEQ ID NO: 64 and having the activity substantially equivalent to the amino acid sequence represented by SEQ ID NO: 64, etc.

Examples of the substantially equivalent activity include a ligand binding activity, a signal transduction activity, etc. The term "substantially equivalent" is used to mean that the nature of the activity is the same. Therefore, although it is preferred that activities such as the ligand binding and signal transduction activities, etc. be equivalent (e.g., about 0.01- to about 100-fold, preferably about 0.5- to about 20-fold, more preferably about 0.5- to about 2-fold), quantitative factors such as a level of the activity, a molecular weight of the protein, etc. may differ.

The activities such as ligand binding and signal transduction activities or the like can be determined according to a publicly known method with some modifications, for example, by the ligand determination methods or the screening methods that will be later described.

Proteins containing the following amino acid sequences are used as the receptor protein of the present invention: (1) (i) amino acid sequences represented by SEQ ID NO: 1 or SEQ ID NO: 3, wherein at least 1 or 2 amino acids (preferably approximately 1 to 30 amino acids, more preferably approximately 1 to 10 amino acids, most preferably several (1 to 5) amino acids) are deleted; (ii) amino acid sequences represented by SEQ ID NO: 1 or SEQ ID NO: 3, to which at least 1 or 2 amino acids (preferably approximately 1 to 30 amino acids, more preferably approximately 1 to 10 amino acids, and most preferably several (1 to 5) amino acids) are added; (iii) amino acid sequences represented by SEQ ID NO: 1 or SEQ ID NO: 3, in which at least 1 or 2 amino acids (preferably approximately 1 to 30 amino acids, more preferably approximately 1 to 10 amino acids, and most preferably several (1 to 5) amino acids) are substituted by other amino acids; or (iv) combination of the amino acid sequences described in the above; (2) (i) amino acid sequences represented by SEQ ID NO: 10 or SEQ ID NO: 14, wherein at least 1 or 2 amino acids (preferably approximately 1 to 30 amino acids, more preferably approximately 1 to 10 amino acids, most preferably several (1 to 5) amino acids) are deleted; (ii) amino acid sequences represented by SEQ ID NO: 10 or SEQ ID NO: 14, to which at least 1 or 2 amino acids (preferably approximately 1 to 30 amino acids, more preferably approximately 1 to 10 amino acids, and most preferably several (1 to 5) amino acids) are added; (iii) amino acid sequences represented by SEQ ID NO: 10 or SEQ ID NO: 14, in which at least 1 or 2 amino acids (preferably approximately 1 to 30 amino acids, more preferably approximately 1 to 10 amino acids, and most preferably several (1 to 5) amino acids) are substituted by other amino acids; or (iv) combination of the amino acid sequences described in the above; (3) (i) amino acid sequences represented by SEQ ID NO: 64, wherein at least 1 or 2 amino acids (preferably approximately 1 to 30 amino acids, more preferably approximately 1 to 10 amino acids, most preferably several (1 to 5) amino acids) are deleted; (ii) amino acid sequences represented by SEQ ID NO: 64, to which at least 1 or 2 amino acids (preferably approximately 1 to 30 amino acids, more preferably approximately 1 to 10 amino acids, and most preferably several (1 to 5) amino acids) are added; (iii) amino acid sequences represented by SEQ ID NO: 64, in which at least 1 or 2 amino acids (preferably approximately 1 to 30 amino acids, more preferably approximately 1 to 10 amino acids, and most preferably several (1 to 5) amino acids) are substituted by other amino acids; or (iv) combination of the amino acid sequences described in the above.

Throughout the present specification, the receptor proteins are represented in accordance with the conventional way of describing peptides, that is, the N-terminus (amino terminus) at the left hand and the C-terminus (carboxyl terminus) at the right hand. In the receptor proteins of the present invention including the receptor proteins containing the amino acid sequence shown by SEQ ID NO: 1 or SEQ ID NO: 3, the C-terminus is usually in the form of a carboxyl group (—COOH) or a carboxylate (—$COO^-$) but may be in the form of an amide (—$CONH_2$) or an ester (—COOR).

Examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl group such as a phenyl-$C_{1-2}$-alkyl group, e.g., benzyl, phenethyl, etc., or an α-naphthyl-$C_{1-2}$-alkyl group such as α-naphthylmethyl, etc.; and the like. In addition, pivaloyloxymethyl or the like, which is used widely as an ester for oral administration, may also be used.

Where the receptor protein of the present invention contains a carboxyl group (or a carboxylate) at a position other than the C-terminus, it may be amidated or esterified and such an amide or ester is also included within the receptor protein of the present invention. The ester group may be the same group as that described with respect to the C-terminus described above.

Furthermore, examples of the receptor protein of the present invention include variants of the above receptor proteins, wherein the amino group at the N-terminal methionine residue of the protein supra is protected with a protecting group (for example, a $C_{1-6}$ acyl group such as a $C_{2-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{2-6}$ alkanoyl group, e.g., formyl group, acetyl group, etc.), or conjugated proteins such as glycoproteins bound to sugar chains.

Specific examples of the receptor protein of the present invention which can be used include a receptor protein containing an amino acid sequence represented by SEQ ID NO: 1 or SEQ ID NO: 3, a receptor protein containing an amino acid sequence represented by SEQ ID NO: 10 or SEQ ID NO: 14, a receptor protein containing an amino acid sequence represented by SEQ ID NO: 64, etc.

As partial peptides of the receptor protein of the present invention (hereinafter sometimes referred to as the partial peptides), any partial peptide can be used so long as it can be a partial peptide of the receptor protein. Among the receptor protein molecules of the present invention, for example, those having a site exposed to the outside of a cell membrane and having a receptor binding activity can be used.

Specifically, the partial peptide of (1) the receptor protein containing the amino acid sequence represented by SEQ ID NO: 1 or SEQ ID NO: 3, (2) the receptor protein containing the amino acid sequence represented by SEQ ID NO: 10 or SEQ ID NO: 14, or (3) the receptor protein containing the amino acid sequence represented by SEQ ID NO: 64 is a peptide containing the parts analyzed to be extracellular domains (hydrophilic domains) in the hydrophobic plotting analysis. A peptide containing a hydrophobic domain in part can be used as well. In addition, the peptide may contain each domain separately or plural domains together.

In the receptor protein of the present invention, preferred partial peptides are those having at least 20, preferably at least 50, and more preferably at least 100 amino acids, in the amino acid sequence which constitutes the receptor protein of the present invention.

The amino acid sequence having substantially the same amino acid sequence includes an amino acid sequence having at least about 50% homology, preferably at least about 60% homology, more preferably at least about 70% homology, much more preferably at least about 80% homology, among others preferably at least about 90% homology and most preferably at least about 95% homology, to these amino acid sequences.

Herein, the term "receptor binding activity substantially equivalent" refers to the same significance as defined above. The "receptor binding activity substantially equivalent" can be assayed in the same manner as given above.

The partial peptide of the present invention may contain an amino acid sequence, wherein at least 1 or 2 amino acids (preferably approximately 1 to 10 amino acids, more preferably several (1 to 5) amino acids) are deleted; to which at least 1 or 2 amino acids (preferably approximately 1 to 20 amino acids, more preferably approximately 1 to 10 amino acids, and most preferably several (1 to 5) amino acids) are added; or, in which at least 1 or 2 amino acids (preferably approximately 1 to 10 amino acids, more preferably several and most preferably approximately 1 to 5 amino acids) are substituted by other amino acids.

In the partial peptide of the present invention, the C-terminus is normally a carboxyl group (—COOH) or carboxylate (—$COO^-$) but the C-terminus may be in the form of an amide (—$CONH_2$) or an ester (—COOR), as has been described with the protein of the present invention.

As in the receptor protein of the present invention described above, the partial peptide of the present invention further includes those in which the amino group of the amino acid residue of the N-terminal methionine residue is protected by a protecting group, those in which the N-terminal residue is cleaved in vivo and the produced glutamine residue is pyroglutaminated, those in which substituents on the side chains of amino acids in the molecule are protected by appropriate protecting groups, conjugated peptides such as so-called glycoproteins, to which sugar chains are bound, and the like.

For salts of the receptor protein or the partial peptide of the present invention, preferred are salts with physiologically acceptable acids, especially physiologically acceptable acid addition salts. Examples of the salts include salts with, for example, inorganic acids (e.g., hydrochloric acid, phosphoric acid, hydrobromic acid, sulfuric acid); salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The receptor protein of the present invention or salts thereof may be manufactured by a publicly known method used to purify a receptor protein from human and other mammalian cells or tissues described above, or by culturing a transformant that contains the DNA encoding the receptor protein of the present invention, as will be later described. Furthermore, the receptor protein or its salts may also be manufactured by the methods for synthesizing proteins or by modifications thereof, which will also be described hereinafter.

Where the receptor protein or its salts are manufactured from human and mammalian tissues or cells, human and mammalian tissues or cells are homogenized, then extracted with an acid or the like, and the extract is isolated and purified by a combination of chromatography techniques such as reverse phase chromatography, ion exchange chromatography, and the like.

To synthesize the receptor protein of the present invention, its partial peptide, or salts or amides thereof according to the present invention, commercially available resins that are used for protein synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmehtylphenyl acetamidomethyl resin, polyacrylamide resin, 4-(2',4'-dimethoxyphenyl-hydroxymethyl)phenoxy resin, 4-(2',4'-dimethoxyphenyl-Fmoc-aminoethyl) phenoxy resin, etc. Using these resins, amino acids in which α-amino groups and functional groups on the side chains are appropriately protected are condensed on the resin in the order of the sequence of the objective protein according to various condensation methods publicly known in the art. At the end of the reaction, the receptor protein is cut out from the resin and at the same time, the protecting groups are removed. Then, intramolecular disulfide bond-forming reaction is performed in a highly diluted solution to obtain the objective protein or its amides.

For condensation of the protected amino acids described above, a variety of activation reagents for protein synthesis may be used, and carbodiimides are particularly preferable. Examples of such carbodiimides include DCC, N,N'-diisopropylcarbodiimide, N-ethyl-N'-(3-dimethylaminoprolyl) carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be chosen from solvents known to be usable for protein condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitrites such as acetonitrile, propionitrile, etc.; esters such as methyl acetate, ethyl acetate, etc.; and appropriate mixtures of these solvents. The reaction temperature is appropriately chosen from the range known to be applicable to protein binding reactions and is usually selected in the range of approximately −20° C. to 50° C. The activated amino acid derivatives are used generally in an excess of 1.5 to 4 times. The condensation is examined by a test using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole.

Examples of the protecting groups used to protect the amino groups of the starting compounds include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower alkanoyl group, such as acetyl group, an aroyl group such as benzoyl group, and a group derived from carbonic acid such as benzyloxycarbonyl group, ethoxycarbonyl group, etc. Examples of a group appropriately used for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br-Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting compounds include the corresponding acid anhydrides, azides, activated esters (esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)). As the activated amino acids, in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethane-sulfonic acid or trifluoroacetic acid, or a mixture solution of these acids; a treatment with a base such as diisopropylethylamine, triethylamine, piperidine or piperazine; and reduction with sodium in liquid ammonia. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol or 1,4-butanedithiol, as well as by a treatment with an alkali such as a dilute sodium hydroxide solution and dilute ammonia.

Protection of functional groups that should not be involved in the reaction of the starting materials, protecting groups, elimination of the protecting groups and activation of functional groups involved in the reaction may be appropriately selected from publicly known groups and publicly known means.

In another method for obtaining the amides of the protein, for example, the α-carboxyl group of the carboxy terminal amino acid is first protected by amidation; the peptide (protein) chain is then extended from the amino group side to a desired length. Thereafter, a protein in which only the protecting group of the N-terminal α-amino group in the peptide chain has been eliminated from the protein and a protein in which only the protecting group of the C-terminal carboxyl group has been eliminated are prepared. The two proteins are condensed in a mixture of the solvents described above. The details of the condensation reaction are the same as described above. After the protected protein obtained by the condensation is purified, all the protecting groups are eliminated by the method described above to give the desired crude protein. This crude protein is purified by various known purification means. Lyophilization of the major fraction gives the amide of the desired protein.

To prepare the esterified protein, for example, the α-carboxyl group of the carboxy terminal amino acid is condensed with a desired alcohol to prepare the amino acid ester, which is followed by procedure similar to the preparation of the amidated protein above to give the ester form of the desired protein.

The partial peptide or its salts in the protein of the present invention can be manufactured by publicly known methods for peptide synthesis, or by cleaving the protein of the present invention with an appropriate peptidase. For the methods for peptide synthesis, for example, either solid phase synthesis or liquid phase synthesis may be used. That is, the partial peptide or amino acids that can construct the protein of the present invention are condensed with the remaining part. Where the product contains protecting groups, these protecting groups are removed to give the desired peptide. Publicly known methods for condensation and elimination of the protecting groups are described in (1)-(5) below.

(1) M. Bodanszky & M. A. Ondetti: Peptide Synthesis, Interscience Publishers, New York (1966)

(2) Schroeder & Luebke: The Peptide, Academic Press, New York (1965)

(3) Nobuo Izumiya, et al.: *Peptide Gosei-no-Kiso to Jikken* (Basics and experiments of peptide synthesis), published by Maruzen Co. (1975)

(4) Haruaki Yajima & Shunpei Sakakibara: *Seikagaku Jikken Koza* (Biochemical Experiment) 1, *Tanpakushitsu no Kagaku* (Chemistry of Proteins) IV, 205 (1977)

(5) Haruaki Yajima, ed.: *Zoku Iyakuhin no Kaihatsu* (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the partial peptide of the present invention. When the partial peptide obtained by the above methods is in a free form, the peptide can be converted into an appropriate salt by a publicly known method; when the protein is obtained in a salt form, it can be converted into a free form by a publicly known method.

The polynucleotide encoding the receptor protein of the present invention may be any polynucleotide so long as it contains the base sequence (DNA or RNA, preferably DNA) encoding the receptor protein of the present invention described above. Such a polynucleotide may also be any one of DNA encoding the receptor protein of the present invention, RNA such as mRNA, etc., and may be double-stranded or single-stranded. Where the polynucleotide is double-stranded, it may be double-stranded DNA, double-stranded RNA or DNA:RNA hybrid. Where the polynucleotide is single-stranded, it may be a sense strand (i.e., a coding strand) or an antisense strand (i.e., a non-coding strand).

Using the polynucleotide encoding the receptor protein of the present invention, mRNA of the receptor protein of the present invention can be quantified by, for example, the publicly known method published in separate volume of *Jikken Igaku* 15 (7) "New PCR and its application" (1997), or by its modifications.

The DNA encoding the receptor protein of the present invention may be any of genomic DNA, genomic DNA library, cDNA derived from the cells and tissues described above, cDNA library derived from the cells and tissues described above and synthetic DNA. The vector to be used for the library may be any of bacteriophage, plasmid, cosmid and phagemid. The DNA may also be directly amplified by reverse transcriptase polymerase chain reaction (hereinafter abbreviated as RT-PCR) using the total RNA or mRNA fraction prepared from the cells and tissues described above.

Specifically, the DNA encoding the receptor protein of the present invention may be (1) DNA containing the base sequence shown by SEQ ID NO: 2 or SEQ ID NO: 4, or DNA hybridizable to DNA containing the base sequence represented by SEQ ID NO: 2 or SEQ ID NO: 4 under highly stringent conditions and encoding a receptor protein having the activities substantially equivalent to those of the receptor protein containing the amino acid sequence represented by SEQ ID NO: 1 or SEQ ID NO: 3 (e.g., a ligand binding activity, a signal transduction activity, etc.), (2) DNA containing the base sequence shown by SEQ ID NO: 11 or SEQ ID NO: 15, or DNA hybridizable to DNA containing the base sequence represented by SEQ ID NO: 11 or SEQ ID NO: 15 under highly stringent conditions and encoding a receptor protein having the activities substantially equivalent to those of the receptor protein containing the amino acid sequence represented by SEQ ID NO: 10 or SEQ ID NO: 14 (e.g., a ligand binding activity, a signal transduction activity, etc.), (3) DNA containing the base sequence shown by SEQ ID NO: 65, or DNA hybridizable to DNA containing the base sequence represented by SEQ ID NO: 65 under highly stringent conditions and encoding a receptor protein having the activities substantially equivalent to those of the receptor protein containing the amino acid sequence represented by SEQ ID NO: 64 (e.g., a ligand binding activity, a signal transduction activity, etc.).

Specific examples of the DNA hybridizable to the base sequence represented by SEQ ID NO: 2 or SEQ ID NO: 4 under highly stringent conditions include DNA containing a base sequence having at least about 70% homology, preferably at least about 80% homology, more preferably at least about 90% homology and most preferably at least about 95% homology, to the base sequence represented by SEQ ID NO: 2 or SEQ ID NO: 4.

Specific examples of the DNA hybridizable to the base sequence represented by SEQ ID NO: 11 or SEQ ID NO: 15 under highly stringent conditions include DNA containing a base sequence having at least about 70% homology, preferably at least about 80% homology, more preferably at least about 90% homology and most preferably at least about 95% homology, to the base sequence represented by SEQ ID NO: 11 or SEQ ID NO: 15.

Specific examples of the DNA hybridizable to the base sequence represented by SEQ ID NO: 65 under highly stringent conditions include DNA containing a base sequence having at least about 70% homology, preferably at least about 80% homology, more preferably at least about 90% homology and most preferably at least about 95% homology, to the base sequence represented by SEQ ID NO: 65.

The hybridization can be carried out by publicly known methods or by modifications of these methods, for example, according to the method described in Molecular Cloning, 2nd (J. Sambrook et al., Cold Spring Harbor Lab. Press, 1989). A commercially available library may also be used according to the instructions of the attached manufacturer's protocol. Preferably, the hybridization can be carried out under highly stringent conditions.

The highly stringent conditions used herein are, for example, those in a sodium concentration at about 19 mM to about 40 mM, preferably about 19 mM to about 20 mM at a temperature of about 50° C. to about 70° C., preferably about 60° C. to about 65° C. In particular, hybridization conditions in a sodium concentration of about 19 mM at a temperature of about 65° C. are most preferred.

More specifically, (1) for the DNA encoding the receptor protein having the amino acid sequence represented by SEQ ID NO: 1 or SEQ ID NO: 3, there may be employed DNA having the base sequence represented by SEQ ID NO: 2 or SEQ ID NO: 4; (2) for the DNA encoding the receptor protein having the amino acid sequence represented by SEQ ID NO: 10 or SEQ ID NO: 14, there may be employed DNA having the base sequence represented by SEQ ID NO: 11 or SEQ ID NO: 15; (3) for the DNA encoding the receptor protein having the amino acid sequence represented by SEQ ID NO: 64, there may be employed DNA having the base sequence represented by SEQ ID NO: 65.

The polynucleotide comprising a part of the base sequence of the DNA encoding the receptor protein of the present invention or a part of the base sequence complementary to the DNA is used to mean to embrace not only the DNA encoding the partial peptide of the present invention described below but also RNA.

According to the present invention, antisense polynucleotides (nucleic acids) that can inhibit the replication or expression of G protein-coupled receptor protein genes can be designed and synthesized based on the base sequence information of the cloned or determined DNA encoding the G protein-coupled receptor protein. Such a polynucleotide (nucleic acid) is capable of hybridizing to RNA of G protein-coupled receptor protein gene to inhibit the synthesis or function of said RNA or capable of modulating or controlling the expression of a G protein-coupled receptor protein gene via interaction with G protein-coupled receptor protein-associated RNA. Polynucleotides complementary to the selected sequences of RNA associated with G protein-coupled receptor protein and polynucleotides specifically hybridizable to the G protein-coupled receptor protein-associated RNA are useful in modulating or controlling the expression of a G protein-coupled receptor protein gene in vivo and in vitro, and useful for the treatment or diagnosis of diseases. The term "corresponding" is used to mean homologous to or complementary to a particular sequence of the nucleotide, base sequence or nucleic acid including the gene. The term "corresponding" between nucleotides, base sequences or nucleic acids and peptides (proteins) usually refer to amino acids of a peptide (protein) under the order derived from the sequence of nucleotides (nucleic acids) or their complements. In the G protein-coupled receptor protein genes, the 5' end hairpin loop, 5' end 6-base-pair repeats, 5' end untranslated region, polypeptide translation initiation codon, protein coding region, ORF translation initiation codon, 3' end untranslated region, 3' end palindrome region, and 3' end hairpin loop, may be selected as preferred target regions, though any other region may be selected as a target in the G protein-coupled receptor protein genes.

The relationship between the targeted nucleic acids and the polynucleotides complementary to at least a part of the target, specifically the relationship between the target and the polynucleotides hybridizable to the target, can be denoted to be "antisense". Examples of the antisense polynucleotides include polynucleotides containing 2-deoxy-D-ribose, polynucleotides containing D-ribose, any other type of polynucleotides which are N-glycosides of a purine or pyrimidine base, or other polymers containing non-nucleotide backbones (e.g., protein nucleic acids and synthetic sequence-specific nucleic acid polymers commercially available) or other polymers containing nonstandard linkages (provided that the polymers contain nucleotides having such a configuration that allows base pairing or base stacking, as is found in DNA or RNA), etc. The antisense polynucleotides may be double-stranded DNA, single-stranded DNA, single-stranded RNA or a DNA:RNA hybrid, and may further include unmodified polynucleotides (or unmodified oligonucleotides), those with publicly known types of modifications, for example, those with labels known in the art, those with caps, methylated polynucleotides, those with substitution of one or more naturally occurring nucleotides by their analogue, those with intramolecular modifications of nucleotides such as those with uncharged linkages (e.g., methyl phosphonates, phosphotriesters, phosphoramidates, carbamates, etc.) and those with charged linkages or sulfur-containing linkages (e.g., phosphorothioates, phosphorodithioates, etc.), those having side chain groups such as proteins (nucleases, nuclease inhibitors, toxins, antibodies, signal peptides, poly-L-lysine, etc.), saccharides (e.g., monosaccharides, etc.), those with intercalators (e.g., acridine, psoralen, etc.), those containing chelators (e.g., metals, radioactive metals, boron, oxidative metals, etc.), those containing alkylating agents, those with modified linkages (e.g., a anomeric nucleic acids, etc.), and the like. Herein the terms "nucleoside", "nucleotide" and "nucleic acid" are used to refer to moieties that contain not only the purine and pyrimidine bases, but also other heterocyclic bases, which have been modified. Such modifications may include methylated purines and pyrimidines, acylated purines and pyrimidines and other heterocyclic rings. Modified nucleotides and modified nucleotides also include modifications on the sugar moiety, wherein, for example, one or more hydroxyl groups may optionally be substituted with a halogen atom(s), an aliphatic group(s), etc., or may be converted into the corresponding functional groups such as ethers, amines, or the like.

The antisense polynucleotide (nucleic acid) of the present invention is RNA, DNA or a modified nucleic acid (RNA, DNA). Specific examples of the modified nucleic acid are, but not limited to, sulfur and thiophosphate derivatives of nucleic acids and those resistant to degradation of polynucleoside amides or oligonucleoside amides. The antisense nucleic acids of the present invention can be modified preferably based on the following design, that is, by increasing the intracellular stability of the antisense nucleic acid, increasing the cellular permeability of the antisense nucleic acid, increasing the affinity of the nucleic acid to the targeted sense strand to a higher level, or minimizing the toxicity, if any, of the antisense nucleic acid.

Many of such modifications are known in the art, as disclosed in J. Kawakami, et al., Pharm. Tech. Japan, Vol. 8, pp. 247, 1992; Vol. 8, pp. 395, 1992; S. T. Crooke, et al. ed., Antisense Research and Applications, CRC Press, 1993; etc.

The antisense nucleic acid of the present invention may contain altered or modified sugars, bases or linkages. The antisense nucleic acid may also be provided in a specialized form such as liposomes, microspheres, or may be applied to gene therapy, or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached to the nucleic acid at the 3' or 5' ends thereof and may also be attached thereto through a base, sugar, or intramolecular nucleoside linkage. Other moieties may be capping groups specifically placed at the 3' or 5' ends of the nucleic acid to prevent degradation by nucleases such as exonuclease, RNase, etc. Such capping groups include, but are not limited to, hydroxyl protecting groups known in the art, including glycols such as polyethylene glycol, tetraethylene glycol and the like.

The inhibitory action of the antisense nucleic acid can be examined using the transformant of the present invention, the gene expression system of the present invention in vivo and in vitro, or the translation system of the G protein-coupled receptor protein in vivo and in vitro. The nucleic acid can be applied to cells by a variety of publicly known methods.

The DNA encoding the partial peptide of the present invention may be any DNA so long as it contains the base sequence encoding the partial peptide of the present invention described above. The DNA may also be any of genomic DNA, genomic DNA library, cDNA derived from the cells and tissues described above, cDNA library derived from the cells and tissues described above and synthetic DNA. The vector to be used for the library may be any of bacteriophage, plasmid, cosmid and phagemid. The DNA may also be directly amplified by reverse transcriptase polymerase chain reaction (hereinafter abbreviated as RT-PCR) using mRNA fraction prepared from the cells and tissues described above.

Specifically, the DNA encoding the partial peptide of the present invention may be any one of, for example, (1) DNA having a partial base sequence of the DNA containing the base sequence represented by SEQ ID NO: 2 or SEQ ID NO: 4, (2) DNA having a DNA hybridizable to the DNA containing the base sequence represented by SEQ ID NO: 2 or SEQ ID NO: 4 under highly stringent conditions and having a partial base sequence of the DNA encoding a protein which has the activities (e.g., a ligand-biding activity, a signal transduction activity, etc.) substantially equivalent to those of the peptide of the receptor protein represented by SEQ ID NO: 1 or SEQ ID NO: 3, (3) DNA having a partial base sequence of the DNA containing the base sequence represented by SEQ ID NO: 11 or SEQ ID NO: 15, (4) DNA having a DNA hybridizable to the DNA containing the base sequence represented by SEQ ID NO: 11 or SEQ ID NO: 15 under highly stringent conditions and having a partial base sequence of the DNA encoding a protein which has the activities (e.g., a ligand-biding activity, a signal transduction activity, etc.) substantially equivalent to those of the peptide of the receptor protein represented by SEQ ID NO: 10 or SEQ ID NO: 14, (5) DNA having a partial base sequence of the DNA containing the base sequence represented by SEQ ID NO: 65, or (6) DNA having a DNA hybridizable to the DNA containing the base sequence represented by SEQ ID NO: 65 under highly stringent conditions and having a partial base sequence of the DNA encoding a protein which has the activities (e.g., a ligand-biding activity, a signal transduction activity, etc.) substantially equivalent to those of the peptide of the receptor protein represented by SEQ ID NO: 64.

Specific examples of the DNA that is hybridizable to the base sequence represented by SEQ ID NO: 2 or SEQ ID NO: 4 under highly stringent conditions include DNA containing a base sequence having at least about 70% homology, preferably at least about 80% homology, more preferably at least about 90% homology and most preferably at least about 95% homology, to the base sequence represented by SEQ ID NO: 2 or SEQ ID NO: 4.

Specific examples of the DNA that is hybridizable to the base sequence represented by SEQ ID NO: 11 or SEQ ID NO: 15 under highly stringent conditions include DNA containing a base sequence having at least about 70% homology, preferably at least about 80% homology, more preferably at least about 90% homology and most preferably at least about 95% homology, to the base sequence represented by SEQ ID NO: 11 or SEQ ID NO: 15.

Specific examples of the DNA that is hybridizable to the base sequence represented by SEQ ID NO: 65 under highly stringent conditions include DNA containing a base sequence having at least about 70% homology, preferably at least about 80% homology, more preferably at least about 90% homology and most preferably at least about 95% homology, to the base sequence represented by SEQ ID NO: 65.

For cloning of the DNA that completely encodes the receptor protein of the present invention or its partial peptide (hereinafter sometimes collectively referred to as the receptor protein of the present invention), the DNA may be either amplified by PCR using synthetic DNA primers containing a part of the base sequence of DNA encoding the peptide of the present invention, or the DNA inserted into an appropriate vector can be selected by hybridization with a labeled DNA fragment or synthetic DNA that encodes a part or entire region of the receptor protein of the present invention. The hybridization can be carried out, for example, according to the method described in Molecular Cloning, 2nd, J. Sambrook et al., Cold Spring Harbor Lab. Press, 1989. The hybridization may also be performed using commercially available library in accordance with the protocol described in the attached instructions.

Conversion of the base sequence of the DNA can be effected by publicly known methods such as the ODA-LA PCR method, the Gupped duplex method or the Kunkel method or its modification by using a publicly known kit available as Mutan™-G or Mutan™-K (both manufactured by Takara Shuzo Co., Ltd.).

The cloned DNA encoding the receptor protein can be used as it is, depending upon purpose or, if desired, after digestion with a restriction enzyme or after addition of a linker thereto. The DNA may contain ATG as a translation initiation codon at the 5' end thereof and may further contain TAA, TGA or TAG as a translation termination codon at the 3' end thereof. These translation initiation and termination codons may also be added by using an appropriate synthetic DNA adapter.

The expression vector for the receptor protein of the present invention can be manufactured, for example, by (a) excising the desired DNA fragment from the DNA encoding the receptor protein of the present invention, and then (b) ligating the DNA fragment with an appropriate expression vector downstream a promoter in the vector.

Examples of the vector include plasmids derived form *E. coli* (e.g., pCR4, pCR2.1, pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNAI/Neo, etc.

The promoter used in the present invention may be any promoter if it matches well with a host to be used for gene expression. In the case of using animal cells as the host, examples of the promoter include SRα promoter, SV40 promoter, LTR promoter, CMV promoter, HSV-TK promoter, etc.

Among them, CMV promoter or SRα promoter is preferably used. Where the host is bacteria of the genus *Escherichia*, preferred examples of the promoter include trp promoter, lac promoter, recA promoter, $\lambda P_L$ promoter, Ipp promoter, etc. In the case of using bacteria of the genus *Bacillus* as the host, preferred example of the promoter are SPO1 promoter, SPO2 promoter and penP promoter. When yeast is used as the host, preferred examples of the promoter are PHO5 promoter, PGK promoter, GAP promoter and ADH promoter. When insect cells are used as the host, preferred examples of the promoter include polyhedrin prompter and P10 promoter.

In addition to the foregoing examples, the expression vector may further optionally contain an enhancer, a splicing signal, a polyA addition signal, a selection marker, SV40 replication origin (hereinafter sometimes abbreviated as SV40ori) etc. Examples of the selection marker include dihydrofolate reductase (hereinafter sometimes abbreviated as dhfr) gene [methotrexate (MTX) resistance], ampicillin resistant gene (hereinafter sometimes abbreviated as $Amp^r$), neomycin resistant gene (hereinafter sometimes abbreviated as $Neo^r$, G418 resistance), etc. In particular, when dhfr gene is used as the selection marker in CHO ($dhfr^-$) cells, selection can also be made on thymidine free media.

If necessary and desired, a signal sequence that matches with a host is added to the N-terminus of the receptor protein of the present invention. Examples of the signal sequence that can be used are Pho A signal sequence, OmpA signal sequence, etc. in the case of using bacteria of the genus *Escherichia* as the host; α-amylase signal sequence, subtilisin signal sequence, etc. in the case of using bacteria of the genus *Bacillus* as the host; MFα signal sequence, SUC2 signal sequence, etc. in the case of using yeast as the host; and insulin signal sequence, α-interferon signal sequence, antibody molecule signal sequence, etc. in the case of using animal cells as the host, respectively.

Using the vector containing the DNA encoding the receptor protein of the present invention thus constructed, transformants can be manufactured.

Examples of the host, which may be employed, are bacteria belonging to the genus *Escherichia*, bacteria belonging to the genus *Bacillus*, yeast, insect cells, insects and animal cells, etc.

Specific examples of the bacteria belonging to the genus *Escherichia* include *Escherichia coli* K12 DH1 (Proc. Natl. Acad. Sci. U.S.A., 60, 160 (1968)), JM103 (Nucleic Acids Research, 9, 309 (1981)), JA221 (Journal of Molecular Biology, 120, 517 (1978)), HB101 (Journal of Molecular Biology, 41, 459 (1969)), C600 (Genetics, 39, 440 (1954)), DH5α (Inoue, H., Nojima, H., Gene, 96, 23-28 (1990)), DH10B (Proc. Natl. Acad. Sci. USA, 87, 4645-4649 (1990)), etc.

Examples of the bacteria belonging to the genus *Bacillus* include *Bacillus subtilis* MI114 (Gene, 24, 255 (1983)), 207-21 (Journal of Biochemistry, 95, 87 (1984)), etc.

Examples of yeast include *Saccharomyces cereviseae* AH22, $AH22R^-$, NA87-11A, DKD-5D, 20B-12, *Schizosaccharomyces pombe* NCYC1913, NCYC2036, *Pichia pastoris* KM71, etc.

Examples of insect cells include, for the virus AcNPV, *Spodoptera frugiperda* cells (Sf cells), MG1 cells derived from mid-intestine of *Trichoplusia ni*, High Five™ cells derived from egg of *Trichoplusia ni*, cells derived from *Mamestra brassicae*, cells derived from *Estigmena acrea*, etc.; and for the virus BmNPV, *Bombyx mori* N cells (BmN cells), etc. are used. Examples of the Sf cell which can be used are Sf9 cells (ATCC CRL1711) and Sf21 cells (both cells are described in Vaughn, J. L. et al., In Vivo, 13, 213-217 (1977).

As the insect, for example, a larva of *Bombyx mori* can be used (Maeda, et al., Nature, 315, 592 (1985)).

Examples of animal cells include monkey cells COS-7, Vero, Chinese hamster cells CHO (hereinafter referred to as CHO cells), dhfr gene deficient Chinese hamster cells CHO (hereinafter simply referred to as CHO($dhfr^-$) cell), mouse L cells, mouse AtT-20, mouse myeloma cells, rat GH3, human FL cells, etc.

Bacteria belonging to the genus *Escherichia* can be transformed, for example, by the method described in Proc. Natl. Acad. Sci. U.S.A., 69, 2110 (1972) or Gene, 17, 107 (1982).

Bacteria belonging to the genus *Bacillus* can be transformed, for example, by the method described in Molecular & General Genetics, 168, 111 (1979).

Yeast can be transformed, for example, by the method described in Methods in Enzymology, 194, 182-187 (1991), Proc. Natl. Acad. Sci. U.S.A., 75, 1929 (1978), etc.

Insect cells or insects can be transformed, for example, according to the method described in Bio/Technology, 6, 47-55(1988), etc.

Animal cells can be transformed, for example, according to the method described in *Saibo Kogaku* (Cell Engineering), extra issue 8, *Shin Saibo Kogaku Jikken Protocol* (New Cell Engineering Experimental Protocol), 263-267 (1995), published by Shujunsha, or Virology, 52, 456 (1973).

Thus, the transformant transformed with the expression vector containing the DNA encoding the G protein-coupled receptor protein can be obtained.

Where the host is bacteria belonging to the genus *Escherichia* or the genus *Bacillus*, the transformant can be appropriately incubated in a liquid medium which contains materials required for growth of the transformant such as carbon sources, nitrogen sources, inorganic materials, and so on. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials are calcium chloride, sodium dihydrogenphosphate, magnesium chloride, etc. In addition, yeast extract, vitamins, growth promoting factors etc. may also be added to the medium. Preferably, pH of the medium is adjusted to about 5 to about 8.

A preferred example of the medium for incubation of the bacteria belonging to the genus *Escherichia* is M9 medium supplemented with glucose and Casamino acids (Miller, Journal of Experiments in Molecular Genetics, 431-433, Cold Spring Harbor Laboratory, New York, 1972). If necessary and desired, a chemical such as 3β-indolylacrylic acid can be added to the medium thereby to activate the promoter efficiently.

Where the bacteria belonging to the genus *Escherichia* are used as the host, the transformant is usually cultivated at about 15° C. to about 43° C. for about 3 hours to about 24 hours. If necessary and desired, the culture may be aerated or agitated.

Where the bacteria belonging to the genus *Bacillus* are used as the host, the transformant is cultivated generally at about 30° C. to about 40° C. for about 6 hours to about 24 hours. If necessary and desired, the culture can be aerated or agitated.

Where yeast is used as the host, the transformant is cultivated, for example, in Burkholder's minimal medium (Bostian, K. L. et al., Proc. Natl. Acad. Sci. U.S.A., 77, 4505 (1980)) or in SD medium supplemented with 0.5% Casamino acids (Bitter, G. A. et al., Proc. Natl. Acad. Sci. U.S.A., 81, 5330 (1984)). Preferably, pH of the medium is adjusted to about 5 to about 8. In general, the transformant is cultivated at about 20° C. to about 35° C. for about 24 hours to about 72 hours. If necessary and desired, the culture can be aerated or agitated.

Where insect cells or insects are used as the host, the transformant is cultivated in, for example, Grace's Insect Medium (Grace, T. C. C., Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary and desired, the culture can be aerated or agitated.

Where animal cells are employed as the host, the transformant is cultivated in, for example, MEM medium containing about 5% to about 20% fetal bovine serum (Science, 122, 501 (1952)), DMEM medium (Virology, 8, 396 (1959)), RPMI 1640 medium (The Journal of the American Medical Association, 199, 519 (1967)), 199 medium (Proceeding of the Society for the Biological Medicine, 73, 1 (1950)), etc. Preferably, pH of the medium is adjusted to about 6 to about 8. The transformant is usually cultivated at about 30° C. to about 40° C. for about 15 hours to about 60 hours and, if necessary and desired, the culture can be aerated or agitated.

As described above, the G protein-coupled receptor protein of the present invention can be produced into the cell, in the cell membrane or out of the cell of the transformant.

The receptor protein of the present invention can be separated and purified from the culture described above by the following procedures.

When the receptor protein of the present invention is extracted from the culture or cells, after cultivation the transformants or cells are collected by a publicly known method and suspended in a appropriate buffer. The transformants or cells are then disrupted by publicly known methods such as ultrasonication, a treatment with lysozyme and/or freeze-thaw cycling, followed by centrifugation, filtration, etc. Thus, the crude extract of the receptor protein of the present invention can be obtained. The buffer used for the procedures may contain a protein modifier such as urea or guanidine hydrochloride, or a surfactant such as Triton X-100™, etc. When the receptor protein is secreted in the culture, after completion of the cultivation the supernatant can be separated from the transformants or cells to collect the supernatant by a publicly known method.

The receptor protein contained in the supernatant or the extract thus obtained can be purified by appropriately combining the publicly known methods for separation and purification. Such publicly known methods for separation and purification include a method utilizing difference in solubility such as salting out, solvent precipitation, etc.; a method utilizing mainly difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When the receptor protein thus obtained is in a free form, it can be converted into the salt by publicly known methods or modifications thereof. On the other hand, when the receptor protein is obtained in the form of a salt, it can be converted into the free form or in the form of a different salt by publicly known methods or modifications thereof.

The receptor protein produced by the recombinant can be treated, prior to or after the purification, with an appropriate protein modifying enzyme so that the receptor protein can be appropriately modified to partially remove a polypeptide. Examples of the protein-modifying enzyme include trypsin, chymotrypsin, arginyl endopeptidase, protein kinase, glycosidase or the like.

The activity of the thus produced receptor protein of the present invention or salts thereof can be determined by a test binding to a labeled ligand, by an enzyme immunoassay using a specific antibody, or the like.

Antibodies to the receptor protein of the present invention, its partial peptides, or salts thereof may be any of polyclonal antibodies and monoclonal antibodies, as long as they are capable of recognizing the receptor protein of the present invention, its partial peptides, or salts thereof.

The antibodies to the receptor protein of the present invention, its partial peptides, or salts thereof (hereinafter sometimes merely referred to as the receptor protein of the present invention) may be manufactured by publicly known methods for manufacturing antibodies or antisera, using as antigens the receptor protein of the present invention.

[Preparation of Monoclonal Antibody]

(a) Preparation of Monoclonal Antibody-Producing Cells

The receptor protein of the present invention is administered to mammals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once in every two to six weeks and 2 to 10 times in total. Examples of the applicable mammals are monkeys, rabbits, dogs, guinea pigs, mice, rats, sheep and goats, with mice and rats being preferred.

In the preparation of monoclonal antibody-producing cells, warm-blooded animals, e.g., mice, immunized with an antigen wherein the antibody titer is noted is selected, then the spleen or lymph node is collected after 2 to 5 days from the final immunization and antibody-producing cells contained therein are fused with myeloma cells to give monoclonal antibody-producing hybridomas. Measurement of the antibody titer in antisera may be made, for example, by reacting a labeled form of the receptor protein, which will be described later, with the antiserum followed by assaying the binding activity of the labeling agent bound to the antibody. The fusion may be operated, for example, by the known Koehler and Milstein method (Nature, 256, 495, 1975). Examples of the fusion accelerator are polyethylene glycol (PEG), Sendai virus, etc., of which PEG is preferably employed.

Examples of the myeloma cells are NS-1, P3U1, SP2/0, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by incubating at about 20 to about 40° C., preferably at about 30 to about 37° C. for about 1 to about 10 minutes, an efficient cell fusion can be carried out.

Various methods can be used for screening of a monoclonal antibody-producing hybridoma. Examples of such methods include a method which comprises adding the supernatant of hybridoma to a solid phase (e.g., microplate) adsorbed with the receptor protein etc. as an antigen directly or together with a carrier, adding an anti-immunoglobulin antibody (when mouse cells are used for the cell fusion, anti-mouse immunoglobulin antibody is used) labeled with a radioactive substance or an enzyme, or Protein A and detecting the monoclonal antibody bound to the solid phase, and a method which comprises adding the supernatant of hybridoma to a solid phase adsorbed with an anti-immunoglobulin antibody or Protein A, adding the receptor protein labeled with a radioactive substance or an enzyme and detecting the monoclonal antibody bound to the solid phase.

The monoclonal antibody can be selected by publicly known methods or by modifications of these methods. In general, the selection can be effected in a medium for animal cells supplemented with HAT (hypoxanthine, aminopterin and thymidine). Any selection and growth medium can be employed as far as the hybridoma can grow therein. For example, RPMI 1640 medium containing 10% to 20%, preferably 100% to 20% fetal bovine serum, GIT medium (Wako Pure Chemical Industries, Ltd.) containing 10% to 100% fetal bovine serum, a serum free medium for cultivation of a hybridoma (SFM-101, Nissui Seiyaku Co., Ltd.) and the like can be used for the selection and growth medium. The cultivation is carried out generally at 20° C. to 40° C., preferably at about 37° C., for 5 days to 3 weeks, preferably 1 to 2 weeks. The cultivation can be conducted normally in 5% $CO_2$. The antibody titer of the culture supernatant of hybridomas can be determined as in the assay for the antibody titer in antisera described above.

(b) Purification of Monoclonal Antibody

Separation and purification of a monoclonal antibody can be carried out by methods applied to conventional separation and purification of immunoglobulins, as in the conventional methods for separation and purification of polyclonal antibodies [e.g., salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A, Protein G, etc. and dissociating the binding to obtain the antibody].

[Preparation of Polyclonal Antibody]

The polyclonal antibody of the present invention can be manufactured by publicly known methods or modifications thereof. For example, a complex of immunogen (antigen such as the protein of the present invention) and a carrier protein is prepared, and a mammal is immunized with the complex in a manner similar to the method described above for the manufacture of monoclonal antibodies. The product containing the antibody to the receptor protein of the present invention is collected from the immunized animal followed by separation and purification of the antibody.

In the complex of an immunogen and a carrier protein used to immunize a mammal, the type of carrier protein and the mixing ratio of a carrier to hapten may be any type and in any ratio, as long as the antibody is efficiently produced to the hapten immunized by crosslinking to the carrier. For example, bovine serum albumin, bovine thyroglobulins, keyhole limpet hemocyanin, etc. is coupled to hapten in a carrier-to-hapten weight ratio of approximately 0.1 to 20, preferably about 1 to about 5.

A variety of condensing agents can be used for the coupling of a carrier to hapten. Glutaraldehyde, carbodiimide, maleimide activated ester, activated ester reagents containing thiol group or dithiopyridyl group, etc. are used for the coupling.

The condensation product is administered to warm-blooded animals either solely or together with carriers or diluents to the site in which the antibody can be produce by the administration. In order to potentiate the antibody productivity upon the administration, complete Freund's adjuvant or incomplete Freund's adjuvant may be administered. The administration is usually made once approximately in every 2 to 6 weeks and about 3 to about 10 times in total.

The polyclonal antibody can be collected from the blood, ascites, etc., preferably from the blood of mammals immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as applied to the separation and purification of monoclonal antibodies described hereinabove.

The receptor protein of the present invention, its salts, its partial peptides, or salts thereof, and the DNA encoding the receptor protein or the partial peptide can be used for: (1) determination of ligands (agonists) to the G protein-coupled receptor protein of the present invention, (2) prophylactic and/or therapeutic agents for diseases associated with dysfunction of the G protein-coupled receptor protein of the present invention, (3) agents for gene diagnosis, (4) methods of screening compounds that alter the expression level of the receptor protein of the present invention or its partial peptides, (5) prophylactic and/or therapeutic agents for various diseases comprising a compound that alters the expression level of the receptor protein of the present invention or its partial peptides, (6) methods of quantification of ligands to the G protein-coupled receptor protein of the present invention, (7) methods of screening compounds (agonists, antagonists, etc.) that alter the binding property between the G protein-coupled receptor protein of the present invention and ligands, (8) prophylactic and/or therapeutic agents for various diseases comprising a compound (an agonist or an antagonist) that alters the binding property between the G protein-coupled receptor protein of the present invention and ligands, (9) quantification of the receptor protein of the present invention, its partial peptides or salts thereof, (10) methods of screening compounds that alter the amount of the receptor protein of the present invention or its partial peptides in cell membranes, (11) prophylactic and/or therapeutic agents for various diseases comprising a compound that alters the amount of the receptor protein of the present invention or its partial peptides in cell membranes, (12) neutralization by antibodies to the receptor protein of the present invention, its partial peptides, or salts thereof, and (13) preparation of non-human animals that possess the DNA encoding the G protein-coupled receptor protein of the present invention.

In particular, by the use of the receptor binding assay system using the expression system of the recombinant G protein-coupled receptor protein of the present invention, compounds (e.g., agonists, antagonists, etc.) that alter the binding property of human- and mammal-specific ligands for the G protein-coupled receptor protein can be screened, and the agonists or antagonists can be used as prophylactic and therapeutic agents for various diseases.

Hereinafter, the receptor protein of the present invention, its partial peptides, or salts thereof (hereinafter sometimes referred to as the receptor protein of the present invention), the DNA encoding the receptor protein of the present invention or its partial peptides (hereinafter sometimes referred to as the DNA of the present invention) and the antibodies to the receptor protein of the present invention (hereinafter sometimes referred to as the antibodies of the present invention) are specifically described for the use or applications.

(1) Determination of a Ligand (Agonist) to the G Protein-Coupled Receptor Protein of the Present Invention The receptor protein of the present invention or its salts, or the partial peptide or its salts of the present invention are useful as reagents for searching and determining ligands (agonists) to the receptor protein of the present invention or its salts.

That is, the present invention provides a method for determining a ligand to the receptor protein of the present invention, which comprises bringing the receptor protein of the present invention or its salts, or the partial peptide of the present invention or its salts, in contact with a test compound.

Examples of the test compound include publicly known ligands (e.g., angiotensin, bombesin, canavinoid, cholecystokinin, glutamine, serotonin, melatonin, neuropeptide Y, opioid, purines, vasopressin, oxytocin, PACAP (e.g., PACAP27, PACAP38), secretin, glucagon, calcitonin, adrenomedulin, somatostatin, GHRH, CRF, ACTH, GRP, PTH, VIP (vasoactive intestinal and related polypeptide), somatostatin, dopamine, motilin, amylin, bradykinin, CGRP (calcitonin gene-related peptide), leukotrienes, pancreastatin, prostaglandins, thromboxane, adenosine, adrenaline, a chemokine superfamily (e.g., IL-8, GROα, GROβ, GROγ, NAP-2, ENA-78, GCP-2, PF4, IP10, Mig, CXC chemokine subfamily such as PBSF/SDF-1, etc.; CC chemokine subfamily such as MCAF/MCP-1, MCP-2, MCP-3, MCP-4, eotaxin, RANTES, MIP1-α, MIP-1β, HCC-1, MIP-3α/LARC, MIP-3β/ELC, 1-309, TARC, MIPF-1, MIPF-2/eotaxin-2, MDC, DC-CK1/PARC, SLC, etc.; C chemokine subfamily such as lymphotactin; CX3C chemokine subfamily such as fractalkine, etc., etc.), endothelin, enterogastrin, histamine, neurotensin, TRH, pancreatic polypeptide, galanin, lysophosphatidic acid (LPA) or sphingosine 1-phosphate, etc.) as well as other substances, for example, tissue extracts and cell culture supernatants from human and mammals (e.g., mice, rats, swine, bovine, sheep, monkeys, etc.). In addition, a polypeptide containing an amino acid sequence represented by SEQ ID NO: 33, SEQ ID NO: 34, SEQ ID NO: 35, SEQ ID NO: 36, SEQ ID NO: 62, SEQ ID NO: 25, SEQ ID NO: 26, SEQ ID NO: 27, SEQ ID NO: 49, SEQ ID NO: 42, SEQ ID NO: 43, SEQ ID NO: 44 or SEQ ID NO: 45 can be used. For example, the tissue extract or cell culture supernatant is added to the receptor protein of the present invention and fractionated while assaying the cell stimulating activities, etc. to finally give a single ligand.

In more detail, the method for determining ligands of the present invention comprises determining compounds (e.g., peptides, proteins, non-peptide compounds, synthetic compounds, fermentation products, etc.) or salts thereof that bind to the receptor protein of the present invention to provide cell stimulating activities (e.g., the activities that accelerate or suppress arachidonic acid release, acetylcholine release, intracellular $Ca^{2+}$ release, intracellular cAMP production, intracellular cAMP suppression, intracellular cGMP production, inositol phosphate production, change in cell membrane potential, phosphorylation of intracellular proteins, activation of c-fos, pH reduction, etc.), using the receptor of the present invention, its partial peptides or salts thereof, or by the receptor binding assay using the constructed recombinant receptor protein expression system.

The method for determining ligands of the present invention is characterized, for example, by measurement of the amount of the test compound bound to the receptor protein or the partial peptide, or by assaying the cell-stimulating activities, etc., when the test compound is brought in contact with the receptor protein of the present invention or its partial peptides.

More specifically, the present invention provides the following features:

(1) A method for determining a ligand to the receptor protein of the present invention or its salt, which comprises bringing a labeled test compound in contact with the receptor protein of the present invention or its salt or the partial peptide of the present invention or its salt and measuring the amount of the labeled test compound bound to the receptor protein or its salt or to the partial peptide or its salt;

(2) A method for determining ligands to the receptor protein of the present invention or its salt, which comprises bringing a labeled test compound in contact with cells or cell membrane fraction containing the receptor protein of the present invention, and measuring the amount of the labeled test compound bound to the cells or the membrane fraction;

(3) A method for determining ligands to the receptor protein of the present invention, which comprises culturing a transformant containing the DNA encoding the receptor protein of the present invention, bringing a labeled test compound in contact with the receptor protein expressed on the cell membrane by said culturing, and measuring the amount of the labeled test compound bound to the receptor protein or its salt;

(4) A method for determining ligands to the receptor protein of the present invention or its salt, which comprises bringing a test compound in contact with cells containing the receptor protein of the present invention and measuring the receptor protein-mediated cell stimulating activities (e.g., the activities that promote or suppress arachidonic acid release, acetylcholine release, intracellular $Ca^{2+}$ release, intracellular cAMP production, intracellular cAMP suppression, intracellular cGMP production, inositol phosphate production, change in cell membrane potential, phosphorylation of intracellular proteins, activation of c-fos, pH reduction, etc.); and (5) A method for determining ligands to the receptor protein of the present invention or its salt, which comprises culturing a transformant containing DNA encoding the receptor protein of the present invention, bringing a labeled test compound in contact with the receptor protein expressed on the cell membrane by said culturing, and measuring the receptor protein-mediated cell stimulating activities (e.g., the activities that promote or suppress arachidonic acid release, acetylcholine release, intracellular $Ca^{2+}$ release, intracellular cAMP production, intracellular cAMP suppression, intracellular cGMP production, inositol phosphate production, change in cell membrane potential, phosphorylation of intracellular proteins, activation of c-fos, pH reduction, etc.).

It is particularly preferred to perform the tests (1) to (3) described above, thereby to confirm that the test compound can bind to the receptor protein of the present invention, followed by the tests (4) and (5) described above.

Any protein exemplified to be usable as the receptor protein for determining ligands, so long as it contains the receptor protein of the present invention or the partial peptide of the present invention. However, the receptor protein that is abundantly expressed using animal cells is appropriate.

The receptor protein of the present invention can be manufactured by the method for expression described above, preferably by expressing DNA encoding the receptor protein in mammalian or insect cells. As DNA fragments encoding the desired portion of the protein, complementary DNA is generally used but not necessarily limited thereto. For example, gene fragments or synthetic DNA may also be used. For introducing a DNA fragment encoding the receptor protein of the present invention into host animal cells and efficiently expressing the same, it is preferred to insert the DNA fragment downstream a polyhedrin promoter of nuclear polyhedrosis virus (NPV), which is a baculovirus having insect hosts, an SV40-derived promoter, a retrovirus promoter, a metallothionein promoter, a human heat shock promoter, a cytomegalovirus promoter, an SRα promoter or the like. The amount and quality of the receptor expressed can be determined by a publicly known method. For example, this determination can be made by the method described in the literature (Nambi, P., et al., J. Biol. Chem., 267, 19555-19559 (1992)).

Accordingly, the subject containing the receptor protein of the present invention, its partial peptides or salts thereof in the method for determining the ligand according to the present invention may be the receptor protein, its partial peptides or salts thereof purified by publicly known methods, cells containing the receptor protein, or membrane fractions of such cells.

Where cells containing the receptor protein of the present invention are used in the method of the present invention for determination of ligands, the cells may be fixed using glutaraldehyde, formalin, etc. The fixation can be made by a publicly known method.

The cells containing the receptor protein of the present invention are host cells that have expressed the receptor protein of the present invention, which host cells include *Escherichia coli, Bacillus subtilis*, yeast, insect cells, animal cells, and the like.

The cell membrane fraction refers to a fraction abundant in cell membrane obtained by cell disruption and subsequent fractionation by a publicly known method. Useful cell disruption methods include cell squashing using a Potter-Elvehjem homogenizer, disruption using a Waring blender or Polytron (manufactured by Kinematica Inc.), disruption by ultrasonication, and disruption by cell spraying through thin nozzles under an increased pressure using a French press or the like. Cell membrane fractionation is effected mainly by fractionation using a centrifugal force, such as centrifugation for fractionation and density gradient centrifugation. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in the receptor protein expressed and membrane components such as cell-derived phospholipids and membrane proteins.

The amount of the receptor protein in the cells containing the receptor protein and in the membrane fraction is preferably $10^3$ to $10^8$ molecules per cell, more preferably $10^5$ to $10^7$ molecules per cell. As the amount of expression increases, the ligand binding activity per unit of membrane fraction (specific activity) increases so that not only the highly sensitive screening system can be constructed but also large quantities of samples can be assayed with the same lot.

To perform the methods (1) through (3) supra for determination of a ligand to the receptor protein of the present invention or its salt, an appropriate receptor fraction and a labeled test compound are required.

The receptor protein fraction is preferably a fraction of naturally occurring receptor protein or a recombinant receptor fraction having an activity equivalent to that of the natural protein. Herein, the term "equivalent activity" is intended to mean a ligand binding activity, a signal transduction activity or the like that is equivalent to that possessed by naturally occurring receptor proteins.

Preferred examples of labeled test compounds include angiotensin, bombesin, canavinoid, cholecystokinin, glutamine, serotonin, melatonin, neuropeptide Y, opioid, purines, vasopressin, oxytocin, PACAP (e.g., PACAP27, PACAP38), secretin, glucagon, calcitonin, adrenomedulin, somatostatin, GHRH, CRF, ACTH, GRP, PTH, VIP (vasoactive intestinal polypeptide), somatostatin, dopamine, motilin, amylin, bradykinin, CGRP (calcitonin gene-related peptide), leukotrienes, pancreastatin, prostaglandins, thromboxane, adenosine, adrenaline, a chemokine superfamily (e.g., IL-8, GROα, GROβ, GROγ, NAP-2, ENA-78, GCP-2, PF4, IP10, Mig, CXC chemokine subfamily such as PBSF/SDF-1, etc.; CC chemokine subfamily such as MCAF/MCP-1, MCP-2, MCP-3, MCP-4, eotaxin, RANTES, MIP1-α, MIP-1β, HCC-1, MIP-3α/LARC, MIP-3β/ELC, I-309, TARC, MIPF-1, MIPF-2/eotaxin-2, MDC, DC-CK1/PARC, SLC, etc.; C chemokine subfamily such as lymphotactin; CX3C chemokine subfamily such as fractalkine, etc., etc.), endothelin, enterogastrin, histamin, neurotensin, TRH, pancreatic polypeptide, galanin, lysophosphatidic acid (LPA) or sphingosine 1-phosphate, etc.), or a polypeptide containing an amino acid sequence represented by SEQ ID NO: 33, SEQ ID NO: 34, SEQ ID NO: 35, SEQ ID NO: 36, SEQ ID NO: 62, SEQ ID NO: 25, SEQ ID NO: 26, SEQ ID NO: 27, SEQ ID NO: 49, SEQ ID NO: 42, SEQ ID NO: 43, SEQ ID NO: 44 or SEQ ID NO: 45, which are labeled with [$^3$H], [$^{125}$I], [$^{14}$C], [$^{35}$S], etc.

More specifically, the ligand to the receptor protein of the present invention or its salt is determined by the following procedures. First, a standard receptor preparation is prepared by suspending cells containing the receptor protein of the present invention or the membrane fraction thereof in a buffer appropriate for use in the determination method. Any buffer can be used so long as it does not inhibit the ligand-receptor binding, such buffers including a phosphate buffer or a Tris-HCl buffer having pH of 4 to 10 (preferably pH of 6 to 8). For the purpose of minimizing non-specific binding, a surfactant such as CHAPS, Tween-80™ (manufactured by Kao-Atlas Inc.), digitonin or deoxycholate, and various proteins such as bovine serum albumin or gelatin, may optionally be added to the buffer. Further for the purpose of suppressing the degradation of the receptors or ligands by proteases, a protease inhibitor such as PMSF, leupeptin, E-64 (manufactured by Peptide Institute, Inc.) and pepstatin may also be added. A given amount (5,000 to 500,000 cpm) of the test compound labeled with [$^3$H], [$^{125}$I], [$^{14}$C], [$^{35}$S] or the like is added to 0.01 ml to 10 ml of the receptor solution. To determine the amount of non-specific binding (NSB), a reaction tube containing an unlabeled test compound in a large excess is also prepared. The reaction is carried out at approximately 0 to 50° C., preferably about 4 to 37° C. for about 20 minutes to about 24 hours, preferably about 30 minutes to about 3 hours. After completion of the reaction, the reaction mixture is filtrated through glass fiber filter paper, etc. and washed with an appropriate volume of the same buffer. The residual radioactivity on the glass fiber filter paper is then measured by means of a liquid scintillation counter or γ-counter. A test compound exceeding 0 cpm in count obtained by subtracting nonspecific binding (NSB) from the total binding (B) (B minus NSB) may be selected as a ligand (agonist) to the receptor protein of the present invention or its salt.

The method (4) or (5) above for determination of a ligand to the receptor protein of the present invention or its salt can be performed as follows. The receptor protein-mediated cell-stimulating activities (e.g., the activities that promote or suppress arachidonic acid release, acetylcholine release, intracellular $Ca^{2+}$ release, intracellular cAMP production, intracellular cAMP suppression, intracellular cGMP production, inositol phosphate production, change in cell membrane potential, phosphorylation of intracellular proteins, activation of c-fos, pH reduction, etc.) may be determined by a publicly known method, or using an assay kit commercially available. Specifically, cells containing the receptor protein are first cultured on a multi-well plate, etc. Prior to the ligand determination, the medium is replaced with fresh medium or with an appropriate non-cytotoxic buffer, followed by incubation for a given period of time in the presence of a test compound, etc. Subsequently, the cells are extracted or the supernatant is recovered and the resulting product is quantified by appropriate procedures. Where it is difficult to detect the production of the index substance (e.g., arachidonic acid) for the cell-stimulating activity due to a degrading enzyme contained in the cells, an inhibitor against such a degrading enzyme may be added prior to the assay. For detecting activities such as the cAMP production suppression activity, the baseline production in the cells is increased by forskolin or the like and the suppressing effect on the increased baseline production may then be detected.

The kit of the present invention for determination of the ligand that binds to the receptor protein of the present invention or its salt comprises the receptor protein of the present invention or its salt, the partial peptide of the present invention or its salt, cells containing the receptor protein of the present invention, or the membrane fraction of the cells containing the receptor protein of the present invention.

Examples of the ligand determination kit of the present invention are given below.

1. Reagents for Determining Ligands (1) Buffers for Assay and Washing

Hanks' Balanced Salt Solution (manufactured by Gibco Co.) supplemented with 0.05% bovine serum albumin (Sigma Co.).

The solution is sterilized by filtration through a 0.45 μm filter and stored at 4° C. Alternatively, the solution may be prepared at use.

(2) Standard G Protein-Coupled Receptor Protein

CHO cells on which the receptor protein of the present invention has been expressed are passaged in a 12-well plate in a density of $5\times10^5$ cells/well followed by culturing at 37° C. under 5% $CO_2$ and 95% air for 2 days.

(3) Labeled Test Compounds

Compounds labeled with [$^3$H], [$^{125}$I], [$^{14}$C], [$^{35}$S], etc., which are commercially available labels, or compounds labeled by appropriate methods.

An aqueous solution of the compound is stored at 4° C. or −20° C. The solution is diluted to 1 μM with an assay buffer at use. A sparingly water-soluble test compound is dissolved in dimethylformamide, DMSO, methanol, etc.

(4) Non-Labeled Compounds

A non-labeled form of the same compound as the labeled compound is prepared in a concentration 100 to 1,000-fold higher than that of the labeled compound.

2. Method for Assay (1) CHO cells expressing the receptor protein of the present invention are cultured in a 12-well culture plate. After washing twice with 1 ml of an assay buffer, 490 μl of the assay buffer is added to each well.

(2) After 5 μl of the labeled test compound is added, the resulting mixture is incubated at room temperature for an hour. To determine the non-specific binding, 5 μl of the non-labeled compound is added to the system.

(3) The reaction mixture is removed and the wells are washed 3 times with 1 ml of washing buffer. The labeled test compound bound to the cells is dissolved in 0.2N NaOH-1% SDS and then mixed with 4 ml of liquid scintillator A (manufactured by Wako Pure Chemical Industries, Ltd.).

(4) The radioactivity is measured using a liquid scintillation counter (manufactured by Beckman Co.).

The ligands that bind to the receptor protein of the present invention or its salt include substances specifically present in hypothalamus, cerebral cortex, colon cancer, lung cancer and the like. Examples of such ligands are angiotensin, bombesin, canavinoid, cholecystokinin, glutamine, serotonin, melatonin, neuropeptide Y, opioids, purines, vasopressin, oxytocin, PACAP (e.g., PACAP27, PACAP38), secretin, glucagon, calcitonin, adrenomedulin, somatostatin, GHRH, CRF, ACTH, GRP, PTH, VIP (vasoactive intestinal peptide), somatostatin, dopamine, motilin, amylin, bradykinin, CGRP (calcitonin gene-related peptide), leukotriens, pancreastatin, prostaglandins, thromboxane, adenosine, adrenaline, a chemokine superfamily (e.g., IL-8, GROα, GROβ, GROγ, NAP-2, ENA-78, GCP-2, PF4, IP10, Mig, CXC chemokine subfamily such as PBSF/SDF-1, etc.; CC chemokine subfamily such as MCAF/MCP-1, MCP-2, MCP-3, MCP-4, eotaxin, RANTES, MIP1-α, MIP-1β, HCC-1, MIP-3α/LARC, MIP-3β/ELC, I-309, TARC, MIPF-1, MIPF-2/eotaxin-2, MDC, DC-CK1/PARC, SLC, etc.; C chemokine subfamily such as lymphotactin; CX3C chemokine subfamily such as fractalkine, etc., etc.), endothelin, enterogastrin, histamine, neurotensin, TRH, pancreatic polypeptide, galanin, lysophosphatidic acid (LPA) or sphingosine 1-phosphate, or a polypeptide containing an amino acid sequence represented by SEQ ID NO: 33, SEQ ID NO: 34, SEQ ID NO: 35, SEQ ID NO: 36, SEQ ID NO: 62, SEQ ID NO: 25, SEQ ID NO: 26, SEQ ID NO: 27, SEQ ID NO: 49, SEQ ID NO: 42, SEQ ID NO: 43, SEQ ID NO: 44 or SEQ ID NO: 45, etc.

(2) Prophylactic and/or Therapeutic Agents for Diseases Associated with Dysfunction of the G Protein-Coupled Receptor Protein of the Present Invention When a compound is clarified to be a ligand of the receptor protein of the present invention by the methods described in (1), (i) the receptor protein of the present invention, or (ii) the DNA encoding the receptor protein can be used, depending on the activities possessed by the ligand, as a prophylactic and/or therapeutic agent for diseases associated with dysfunction of the receptor protein of the present invention.

For example, when the physiological activity of the ligand cannot be expected in a patient (deficiency of the receptor protein) due to a decrease in the receptor protein of the present invention, the activity of the ligand can be exhibited by: (i) administering the receptor protein of the present invention to the patient thereby to supplement the amount of the receptor protein; or (ii) by increasing the amount of the receptor protein in the patient through: i) administration of the DNA encoding the receptor protein of the present invention to express the same in the patient; or ii) insertion and expression of the DNA encoding the receptor protein of the present invention in the objective cells to transplant the cells to the patient, whereby the activity of the ligand can be sufficiently exhibited. That is, the DNA encoding the receptor protein of the present invention is useful as a safe and low toxic prophylactic and/or therapeutic agent for diseases associated with dysfunction of the receptor protein of the present invention.

The receptor protein of the present invention is a novel 7 transmembrane receptor protein that is recognized to have about 32-36% homology on an amino acid sequence level to vasotocin receptor, mesotocin receptor, isotocin receptor or oxytosin receptor, which are a G protein-coupled receptor protein.

The receptor protein or the DNA encoding the receptor protein of the present invention is useful for the prevention and/or treatment of central dysfunction (e.g., Alzheimer's disease, senile dementia, suppression of eating, etc.), endocrine-related diseases (e.g., hypertension, hypogonadism, hypothyroidism, hypopituitarism, etc.), metabolic disorders (e.g., diabetes mellitus, lipid metabolic disorders, hyperlipemia, etc.), cancer (e.g., non-small cell lung carcinoma, cancer of ovary, prostate cancer, stomach cancer, bladder cancer, breast cancer, uterocervical cancer, colon cancer, rectum cancer, etc.), etc.

When the receptor protein of the present invention is used as the prophylactic/therapeutic agents supra, the receptor protein can be prepared into a drug product in a conventional manner.

On the other hand, where the DNA encoding the receptor protein of the present invention (hereinafter sometimes referred to as the DNA of the present invention) is used as the prophylactic/therapeutic agents described above, the DNA itself is administered; alternatively, the DNA is inserted into an appropriate vector such as retrovirus vector, adenovirus vector, adenovirus-associated virus vector, etc. and then administered in a conventional manner. The DNA of the present invention may also be administered as naked DNA, or with adjuvants to assist its uptake by gene gun or through a catheter such as a catheter with a hydrogel.

For example, (i) the receptor protein of the present invention or (ii) the DNA encoding the receptor protein can be used orally, for example, in the form of tablets which may be sugar coated if necessary and desired, capsules, elixirs, microcapsules etc., or parenterally in the form of injectable preparations such as a sterile solution and a suspension in water or with other pharmaceutically acceptable liquid. These preparations can be manufactured by mixing (i) the receptor protein of the present invention or (ii) the DNA encoding the receptor protein with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The effective component in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, and a flavoring agent such as peppermint, akamono oil and cherry. When the unit dosage is in the form of capsules, liquid carriers such as oils and fats may further be used together with the additives described above. A sterile composition for injection may be formulated by conventional procedures used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition. Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol or the like), a polyalcohol (e.g., propylene glycol and polyethylene glycol), a nonionic surfactant (e.g., polysorbate 80™ and HCO-50), etc. Examples of the oily medium include sesame oil and soybean oil, which may also be used in combination with a dissolution aid such as benzyl benzoate and benzyl alcohol.

The prophylactic/therapeutic agent described above may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus-prepared liquid for injection is normally filled in an appropriate ampoule.

Since the thus obtained pharmaceutical preparation is safe and low toxic, the preparation can be administered to human and mammal (e.g., rats, mice, rabbits, sheep, swine, bovine, cats, dogs, monkeys, etc.).

The dose of the receptor protein of the present invention varies depending on subject to be administered, organs to be administered, conditions, routes for administration, etc.; in oral administration, e.g., for the patient with cancer, the dose is normally about 0.1 mg to about 100 mg, preferably about 1.0 to about 50 mg, and more preferably about 1.0 to about 20 mg per day (as 60 kg body weight). In parenteral administration, the single dose varies depending on subject to be administered, target organ, conditions, routes for administration, etc. but it is advantageous, e.g., for the patient with cancer, to administer the active ingredient intravenously in a daily dose of about 0.01 to about 30 mg, preferably about 0.1 to about 20 mg, and more preferably about 0.1 to about 10 mg (as 60 kg body weight). For other animal species, the corresponding dose as converted per 60 kg body weight can be administered.

The dose of the DNA of the present invention varies depending on subject to be administered, organs to be administered, conditions, routes for administration, etc.; in oral administration, e.g., for the patient with cancer, the dose is normally about 0.1 mg to about 100 mg, preferably about 1.0 to about 50 mg, and more preferably about 1.0 to about 20 mg per day (as 60 kg body weight). In parenteral administration, the single dose varies depending on subject to be administered, target organ, conditions, routes for administration, etc. but it is advantageous, e.g., for the patient with cancer, to administer the active ingredient intravenously in a daily dose of about 0.01 to about 30 mg, preferably about 0.1 to about 20 mg, and more preferably about 0.1 to about 10 mg (as 60 kg body weight). For other animal species, the corresponding dose as converted per 60 kg body weight can be administered.

(3) Gene Diagnostic Agent

By using the DNA of the present invention as a probe, an abnormality (gene abnormality) of the DNA or mRNA encoding the receptor protein of the present invention or its partial peptide in human and mammal (e.g., rats, mice, rabbits, sheep, swine, bovine, cats, dogs, monkeys, etc.) can be detected. Therefore, the DNA of the present invention is useful as a gene diagnostic agent for the damage against the DNA or mRNA, its mutation, or its decreased expression, or increased expression or overexpression of the DNA or mRNA.

The gene diagnosis described above using the DNA of the present invention can be performed by, for example, the publicly known Northern hybridization assay or the PCR-SSCP assay (Genomics, 5, 874-879 (1989); Proceedings of the National Academy of Sciences of the United States of America, 86, 2766-2770 (1989)).

(4) Methods of Screening Compounds that Alter the Expression Level of the Receptor Protein of the Present Invention or its Partial Peptide By using the DNA of the present invention as a probe, the DNA can be used for screening of compounds that alter the amount of the receptor protein of the present invention or its partial peptide.

That is, the present invention provides methods of screening compounds that alter the amount of the receptor protein or its partial peptide, which comprises measuring the amount of mRNA in the receptor protein of the present invention or its partial peptide contained in, for example, (i) (a) blood, (b) specific organs, (c) tissues or cells isolated from the organs of non-human mammals, or in (ii) transformants, etc.

The amount of mRNA in the receptor protein of the present invention or its partial peptide can be specifically measured as follows.

(i) Normal or disease models of non-human mammals (e.g., mice, rats, rabbits, sheep, swine, bovine, cats, dogs, monkeys, more specifically, rats with dementia, obese mice, rabbits with arteriosclerosis, tumor-bearing mice, etc.) receive administration of a drug (e.g., anti-dementia agents, hypotensive agents, anticancer agents, antiobestic agents, etc.) or physical stress (e.g., soaking stress, electric shock, light and darkness, low temperature, etc.), and the blood, specific organs (e.g., brain, lung, large intestine, etc.), or tissues or cells isolated from the organs are obtained after a specified period of time.

The mRNA of the receptor protein of the present invention or its partial peptide contained in the thus obtained cells is extracted from the cells, for example, in a conventional manner and quantified using, e.g., TaqManPCR, or may also be analyzed by northern blot technique by publicly known methods.

(ii) Transformants that express the receptor protein of the present invention or its partial peptide are prepared according to the methods described above, and the mRNA of the receptor protein of the present invention or its partial peptide can be quantified and analyzed, as described above.

Compounds that alter the expression level of the receptor protein of the present invention or its partial peptide can be screened by the following procedures.

(i) To normal or disease models of non-human mammals, a test compound is administered at a specified period of time before (30 minutes to 24 hours before, preferably 30 minutes to 12 hours before, more preferably 1 hour to 6 hours before), at a specified time after (30 minutes to 3 days after, preferably 1 hour to 2 days after, more preferably 1 hour to 24 hours after), or simultaneously with a drug or physical stress. At a specified time (30 minute to 3 days, preferably 1 hour to 2 days, more preferably 1 hour to 24 hours) after administration of the test compound, the amount of mRNA in the receptor protein of the present invention or its partial peptide contained in cells are quantified and analyzed.

(ii) Transformants are cultured in a conventional manner and a test compound is mixed in the culture medium. After a specified time (after 1 day to 7 days, preferably after 1 day to 3 days, more preferably after 2 to 3 days), the amount of mRNA in the receptor protein of the present invention or its partial peptide contained in the transformants can be quantified and analyzed.

The compounds or their salts, which are obtainable by the screening methods of the present invention, are compounds that alter the expression level of the receptor protein of the present invention or its partial peptide. Specifically, (a) compounds that potentiate the cell stimulating activities mediated by the G protein-coupled receptor (e.g., activities that promote or suppress arachidonic acid release, acetylcholine release, intracellular $Ca^{2+}$ release, intracellular cAMP production, intracellular cAMP suppression, intracellular cGMP production, inositol phosphate production, alters in cell membrane potential, phosphorylation of intracellular proteins, activation of c-fos, pH reduction, etc.) by increasing the expression level of the receptor protein of the present invention or its partial peptide; and (b) compounds that decrease the cell-stimulating activities by reducing the expression level of the receptor protein of the present invention or its partial peptide.

The compounds include peptides, proteins, non-peptide compounds, synthetic compounds, and fermentation products. They may be novel or known compounds.

The compounds that increase the cell-stimulating activities are useful as safe and low toxic drugs for potentiation of the physiological activity of the receptor protein of the present.

The compounds that decrease the cell-stimulating activities are useful as safe and low toxic drugs for reducing the physiological activity of the receptor protein or its other forms of the present invention.

When the compounds or their salt forms, which are obtainable by the screening methods of the present invention, are used as pharmaceutical compositions, the compounds can be formulated by the conventional methods. For example, as described for the drugs containing the receptor protein of the present invention, the compounds can be prepared into tablets, capsules, elixir, microcapsules, aseptic solution, or suspension.

The preparations obtained as described above are safe and low toxic, and can be administered to human and mammals (e.g., rats, mice, rabbits, sheep, swine, bovine, cats, dogs, monkeys, etc.).

The dose of the compounds or their salt forms varies depending on subject to be administered, target organs, conditions, routes for administration, etc.; in oral administration, e.g., for the patient with cancer, the dose is normally about 0.1 mg to about 100 mg, preferably about 1.0 to about 50 mg, and more preferably about 1.0 to about 20 mg per day (as 60 kg body weight). In parenteral administration, the single dose varies depending on subject to be administered, target organ, conditions, routes for administration, etc. but it is advantageous, e.g., for the patient with cancer, to administer the active ingredient intravenously in a daily dose of about 0.01 to about 30 mg, preferably about 0.1 to about 20 mg, and more preferably about 0.1 to about 10 mg (as 60 kg body weight). For other animal species, the corresponding dose as converted per 60 kg body weight can be administered.

(5) Prophylactic and/or Therapeutic Agents for Various Diseases Comprising the Compounds that Alter the Expression Level of the Receptor Protein of the Present Invention or its Partial Peptide As described above, the receptor protein of the present invention is considered to play some important role such as a role in the central function. Therefore, the compounds that alter the expression level of the receptor protein of the present invention or its partial peptide can be used as prophylactic and/or therapeutic agents for diseases associated with dysfunction of the receptor protein of the present invention.

Where these compounds are used as prophylactic and/or therapeutic agents for diseases associated with dysfunction of the receptor protein of the present invention, the preparations can be obtained by the conventional methods.

For example, the compounds can be administered orally as a sugar coated tablet, capsule, elixir, and microcapsule, or non-orally as injection such as aseptic solution or suspension in water or other pharmaceutically acceptable liquid. For example, preparations of the compounds can be manufactured by mixing with physiologically acceptable known carrier, flavor, filler, vehicle, antiseptic, stabilizer, and binder in a unit-dosage form required for generally approved drug preparation. The amount of the active ingredient is set to an appropriate volume within the specified range.

For the additive miscible with tablets and capsules, for example, binders such as gelatin, cornstarch, tragacanth, and acacia, fillers such as crystalline cellulose, imbibers such as cornstarch, gelatin, and alginic acid, lubricants such as magnesium stearate, sweeteners such as sucrose and saccharin, and flavors such as peppermint, akamono oil and cherry are used. When the dosage form is a capsule, liquid carrier such as fat and oil may be contained. Aseptic compositions for injection can be formulated following the usual preparation procedure such as dissolving or suspending the active substance in vehicle, e.g., water for injection, and natural plant oils e.g., sesame oil and coconut oil. For the aqueous solution for injection, for example, physiological saline and isotonic solutions (e.g., D-sorbitol, D-mannitol, sodium hydrochloride) containing glucose and other adjuvant are used. Appropriate dissolution-assisting agents, for example, alcohol (e.g., ethanol), polyalcohol (e.g., propylene glycol, polyethylene glycol), nonionic surfactant (e.g., polysorbate 80™, HCO-50) may be combined. For the oily solution, for example, sesame oil and soybean oil are used, and dissolution-assisting agents such as benzyl benzoate and benzyl alcohol may be combined.

The prophylactic/therapeutic agents described above may be combined with buffers (e.g., phosphate buffer, sodium acetate buffer), soothing agents (e.g., benzalkonium chloride, procaine hydrochloride), stabilizers (e.g., human serum albumin, polyethylene glycol), preservatives (e.g., benzyl alcohol, phenol), antioxidants, and the like. The preparation for injection is usually filled in appropriate ampoules.

The preparations obtained as described above are safe and low toxic, and can be administered to, for example, human and mammals (e.g., rats, mice, rabbits, sheep, swine, bovine, cats, dogs, monkeys, etc.).

The dose of the compounds or their salt forms varies depending on subject to be administered, target organs, conditions, routes for administration, etc.; in oral administration, e.g., for the patient with cancer, the dose is normally about 0.1 mg to about 100 mg, preferably about 1.0 to about 50 mg, and more preferably about 1.0 to about 20 mg per day (as 60 kg body weight). In parenteral administration, the single dose varies depending on subject to be administered, target organ, conditions, routes for administration, etc. but it is advantageous, e.g., for the patient with cancer, to administer the active ingredient intravenously in a daily dose of about 0.01 to about 30 mg, preferably about 0.1 to about 20 mg, and more preferably about 0.1 to about 10 mg (as 60 kg body weight). For other animal species, the corresponding dose as converted per 60 kg body weight can be administered.

(6) Methods of Quantifying Ligands for the G Protein-Coupled Protein of the Present Invention Since the receptor protein etc. of the present invention has binding affinity to ligands, the ligand concentration can be quantified in vivo with good sensitivity.

The quantification methods of the present invention can be used in combination with, for example, a competitive method. The ligand concentration in a test sample can be measured by contacting the test sample to the receptor protein etc. of the present invention. Specifically, the methods can be used by following, for example, the methods described in (i) and (ii) below or its modified methods.

(i) Hiroshi Irie, ed. "Radioimmunoassay," Kodansha, published in 1974

(ii) Hiroshi Irie, ed. "Sequel to the Radioimmunoassay," Kodansha, published in 1979

(7) Methods of Screening Compounds (Agonists, Antagonists, or the like) that Alter the Binding Property Between the G Protein-Coupled Receptor Protein of the Present Invention and Ligands Using the receptor protein etc. of the present invention, or using the receptor binding assay system of the expression system constructed using the recombinant receptor protein etc., compounds (e.g., peptides, proteins, non-peptide compounds, synthetic compounds, fermentation products, etc.) or salt forms thereof that alter the binding property between ligands and the receptor protein of the present invention can be efficiently screened.

Such compounds include (a) compounds that have the G protein-coupled receptor-mediated cell-stimulating activities (e.g., activities that promote or suppress arachidonic acid release, acetylcholine release, intracellular $Ca^{2+}$ release, intracellular cAMP production, intracellular cAMP suppression, intracellular cGMP production, inositol phosphate production, changes in cell membrane potential, phosphorylation of intracellular proteins, activation of c-fos, pH reduction, etc.) (so-called agonists to the receptor protein of the present invention); (b) compounds that do not have the cell-stimulating activity (so-called antagonists to the receptor protein of the present invention); (c) compounds that potentiate the binding affinity between ligands and the G protein-coupled receptor protein of the present invention; and (d) compounds that reduce the binding affinity between ligands and the G protein-coupled receptor protein of the present invention (it is preferred to screen the compounds described in (a) using the ligand determination methods described above).

That is, the present invention provides methods of screening compounds or their salt forms that alter the binding property between ligands and the receptor protein, its partial peptide or salts thereof, which comprises comparing (i) the case wherein the receptor protein of the present invention, its partial peptide or salts thereof are brought in contact with a ligand, with (ii) the case wherein the receptor protein of the present invention, its partial peptide or salts thereof are brought in contact with a ligand and a test compound.

The screening methods of the present invention are characterized by assaying, for example, the amount of ligand bound to the receptor protein etc., the cell-stimulating activity, etc., and comparing the property between (i) and (ii).

More specifically, the present invention provides the following screening methods:

(1) A method of screening a compound or its salt that alters the binding property between a ligand and the receptor protein etc. of the present invention, which comprises: measuring the amount of a labeled ligand bound to the receptor protein etc., when the labeled ligand is brought in contact with the receptor protein etc. of the present invention and when the labeled ligand and a test compound are brought in contact with the receptor protein etc. of the present invention, and comparing the binding property between them;

(2) A method of screening a compound or its salt that alters the binding property between a ligand and the receptor protein etc. of the present invention, which comprises: measuring the amount of a labeled ligand bound to cells or the membrane fraction of the cells, when the labeled ligand is brought in contact with the cells or cell membrane fraction containing the receptor protein etc. of the present invention and when the labeled ligand and a test compound are brought in contact with the cells or cell membrane fraction containing the receptor protein etc. of the present invention, and comparing the binding property between them;

(3) A method of screening a compound or its salt that alters the binding property between a ligand and the receptor protein etc. of the present invention, which comprises: measuring the amount of a labeled ligand to the receptor protein etc., when the labeled ligand is brought in contact with the receptor protein etc. expressed on the cell membrane induced by culturing a transformant containing the DNA of the present invention and when the labeled ligand and a test compound are brought in contact with the receptor protein etc. of the present invention expressed on the cell membrane induced by culturing a transformant containing the DNA of the present invention, and comparing the binding property between them;

(4) A method of screening a compound or its salt that alters the binding property between a ligand and the receptor protein etc. of the present invention, which comprises: measuring the receptor-mediated cell-stimulating activity (e.g., the activity that promotes or suppresses arachidonic acid release, acetylcholine release, intracellular $Ca^{2+}$ release, intracellular cAMP production, intracellular cAMP suppression, intracellular cGMP production, inositol phosphate production, changes in cell membrane potential, phosphorylation of intracellular proteins, activation of c-fos, pH reduction, etc.), when a compound (e.g., a ligand to the receptor protein etc. of the present invention) that activates the receptor protein etc. of the present invention is brought in contact with cells containing the receptor protein etc. of the present invention and when the compound that activates the receptor protein etc. of the present invention and a test compound are brought in contact with cells containing the receptor protein etc. of the present invention, and comparing the binding property between them; and, (5) A method of screening a compound or its salt that alters the binding property between a ligand and the receptor protein etc. of the present invention, which comprises: measuring the receptor-mediated cell-stimulating activity (e.g., the activity that promotes or suppresses arachidonic acid release, acetylcholine release, intracellular $Ca^{2+}$ release, intracellular cAMP production, intracellular cAMP suppression, intracellular cGMP production, inositol phosphate production, changes in cell membrane potential, phosphorylation of intracellular proteins, activation of c-fos, pH reduction, etc.), when a compound (e.g., a ligand for the receptor protein etc. of the present invention) that activates the receptor protein etc. of the present invention is brought in contact with the receptor protein etc. of the present invention expressed on the cell membrane induced by culturing a transformant containing the DNA of the present invention and when the compound that activates the receptor protein etc. of the present invention and a test compound are brought in contact with the receptor protein etc. of the present invention expressed on the cell membrane induced by culturing a transformant containing the DNA of the present invention, and comparing the binding property between them.

Before the receptor protein etc. of the present invention was obtained, it was required for screening G protein-coupled receptor agonists or antagonists to obtain candidate compounds first, using cells or tissues containing the G protein-coupled receptor protein or the cell membrane fraction from rats or other animals (primary screening), and then examine the candidate compounds whether the compounds actually inhibit the binding between human G protein-coupled receptor protein and ligands (secondary screening). When cells, tissues, or the cell membrane fractions were directly used, it was practically difficult to screen agonists or antagonists to the objective receptor protein, since other receptor proteins were present together.

However, using, for example, the human-derived receptor protein of the present invention, the primary screening becomes unnecessary, and compounds that inhibit the binding between ligands and the G protein-coupled receptor protein can be efficiently screened. Furthermore, it is easy to assess whether the obtained compound is an agonist or antagonist.

Hereinafter, the screening methods of the present invention are described more specifically.

First, for the receptor protein etc. of the present invention used for the screening methods of the present invention, any substance may be used so long as it contains the receptor protein etc. of the present invention described above. The cell membrane fraction from mammalian organs containing the receptor protein etc. of the present invention is preferred. However, it is very difficult to obtain human organs. It is thus preferable to use rat-derived receptor proteins or the like, produced by large-scale expression using recombinants.

To manufacture the receptor protein etc. of the present invention, the methods described above are used, and it is preferred to express the DNA of the present invention in mammalian and insect cells. For the DNA fragment encoding the objective protein region, the complementary DNA, but not necessarily limited thereto, is employed. For example, the gene fragments and synthetic DNA may also be used. To introduce a DNA fragment encoding the receptor protein of the present invention into host animal cells and efficiently express the DNA there, it is preferred to insert the DNA fragment downstream of a polyhedorin promoter of nuclear polyhedrosis virus (NPV) belonging to baculovirus hosted by insects, SV40-derived promoter, retrovirus promoter, metallothionein promoter, human heat shock promoter, cytomegalovirus promoter, or SRα promoter. The amount and quality of the expressed receptor are examined by publicly known methods, for example, the method described in the literature [Nambi, P. et al., The Journal of Biological Chemistry (J. Biol. Chem.), 267, 19555-19559, 1992].

Therefore, in the screening methods of the present invention, the material that contains the receptor protein etc. of the present invention may be the receptor protein etc. purified by publicly known methods, cells containing the receptor protein etc., or the cell membrane fraction containing the receptor protein or the like.

In the screening methods of the present invention, when cells containing the receptor protein etc. of the present invention are used, the cells may be fixed with glutaraldehyde, formalin, etc. The cells can be fixed by publicly known methods.

The cells containing the receptor protein etc. of the present invention are host cells that express the receptor protein or the like. For the host cells, *Escherichia coli, Bacillus subtilis*, yeast, insect cells, animal cells and the like are preferred.

The cell membrane fraction refers to a fraction abundant in cell membrane obtained by cell disruption and subsequent fractionation by a publicly known method. Useful cell disruption methods include cell squashing using a Potter-Elvehjem homogenizer, disruption using a Waring blender or Polytron (manufactured by Kinematica Inc.), disruption by ultrasonication, and disruption by cell spraying through thin nozzles under an increased pressure using a French press or the like. Cell membrane fractionation is effected mainly by fractionation using a centrifugal force, such as centrifugation for fractionation and density gradient centrifugation. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in the receptor protein etc. expressed and membrane components such as cell-derived phospholipids and membrane proteins.

The amount of the receptor protein in the cells containing the receptor protein etc. and in the membrane fraction is preferably $10^3$ to $10^8$ molecules per cell, more preferably $10^5$ to $10^7$ molecules per cell. As the amount of expression increases, the ligand binding activity per unit of membrane fraction (specific activity) increases so that not only the highly sensitive screening system can be constructed but also large quantities of samples can be assayed with the same lot.

To screen the compounds that alter the binding property between ligands and the receptor protein etc. of the present invention described in (1) to (3), for example, an appropriate receptor protein fraction and a labeled ligand are necessary.

The receptor protein fraction is preferably a fraction of naturally occurring receptor protein or a recombinant receptor fraction having an activity equivalent to that of the natural protein. Herein, the equivalent activity is intended to mean a ligand binding activity, a signal transduction activity or the like that is equivalent to that possessed by naturally occurring receptor proteins.

For the labeled ligand, a labeled ligand and a labeled ligand analogue are used. For example, ligands labeled with [$^3$H], [$^{125}$I], [$^{14}$C], [$^{35}$S], etc. are used.

Specifically, to screen the compounds that alter the binding property between ligands and the receptor protein etc. of the present invention, first, the receptor protein standard is prepared by suspending cells or cell membrane fraction containing the receptor protein etc. of the present invention in a buffer appropriate for the screening. For the buffer, any buffer that does not interfere with the binding of ligands to the receptor protein is usable and examples of such a buffer are phosphate buffer, Tris-hydrochloride buffer, etc., having pH of 4 to 10 (preferably pH of 6 to 8). To minimize a non-specific binding, a surfactant such as CHAPS, Tween-80™ (Kao-Atlas Co.), digitonin, deoxycholate, etc. may be added to the buffer. To inhibit degradation of the receptor and ligands by proteases, protease inhibitors such as PMSF, leupeptin, E-64 (manufactured by Peptide Research Laboratory, Co.), and pepstatin may be added. To 0.01 to 10 ml of the receptor solution, a given amount (5,000 to 500,000 cpm) of labeled ligand is added, and $10^4$ M-$10^{-10}$ M of a test compound is simultaneously added to be co-present. To examine non-specific binding (NSB), a reaction tube containing an unlabeled test compound in a large excess is also prepared. The reaction is carried out at approximately 0 to 50° C., preferably about 4 to 37° C. for about 20 minutes to about 24 hours, preferably about 30 minutes to about 3 hours. After completion of the reaction, the reaction mixture is filtrated through glass fiber filter paper, etc. and washed with an appropriate volume of the same buffer. The residual radioactivity on the glass fiber filter paper is then measured by means of a liquid scintillation counter or γ-counter. Regarding the count obtained by subtracting the amount of non-specific binding (NSB) from the count obtained in the absence of any competitive substance ($B_0$) as 100%, when the amount of specific binding (B-NSB) is, for example, 50% or less, the test compound can be selected as a candidate substance having a potential of competitive inhibition.

To perform the methods (4) and (5) supra of screening the compounds that alter the binding property between ligands and the receptor protein etc. of the present invention, the receptor protein-mediated cell-stimulating activity (e.g., activity that promotes or inhibits arachidonic acid release, acetylcholine release, intracellular Ca release, intracellular cAMP production, intracellular cAMP suppression, intracellular cGMP production, inositol phosphate production, changes in cell membrane potential, phosphorylation of intracellular proteins, activation of c-fos, pH reduction, etc.) can be measured using publicly known methods or commercially available kits.

Specifically, the cells containing the receptor protein etc. of the present invention are first cultured on a multi-well plate, etc. Prior to screening, the medium is replaced with fresh medium or with an appropriate non-cytotoxic buffer, followed by incubation for a given period of time in the presence of a test compound, etc. Subsequently, the cells are extracted or the supernatant is recovered and the resulting product is quantified by appropriate procedures. Where it is difficult to detect the production of the index substance (e.g., arachidonic acid) for the cell-stimulating activity due to a degrading enzyme contained in the cells, an inhibitor against such a degrading enzyme may be added prior to the assay. For detecting activities such as the cAMP production suppression activity, the baseline production in the cells is increased by forskolin or the like and the suppressing effect on the increased baseline production may then be detected.

Screening by assaying the cell-stimulating activity requires cells that have expressed an appropriate receptor protein. For the cells that have expressed the receptor protein etc. of the present invention, the cell line possessing the native receptor protein etc. of the present invention, the cell line expressing the recombinant receptor protein described above and the like are desirable.

For the test compound, for example, peptides, proteins, non-peptide compounds, synthetic compounds, fermentation products, cell extracts, plant extracts, and animal tissue extracts are used. These compounds may be novel or known compounds.

The kits for screening the compounds or their salts that alter the binding property between ligands and the receptor protein etc. of the present invention comprise the receptor protein etc. of the present invention, cells containing the receptor protein etc. of the present invention, or the membrane fraction of cells containing the receptor protein etc. of the present invention.

Examples of the screening kits of the present invention are as follow.

1. Reagents for Screening (1) Buffer for Measurement and Washing

Hanks' balanced salt solution (manufactured by Gibco Co.) supplemented with 0.05% bovine serum albumin (manufactured by Sigma Co.).

The solution is sterilized by filtration through a 0.45 μm filter, and stored at 4° C. or may be prepared at use.

(2) Standard G Protein-Coupled Receptor

CHO cells expressing the receptor protein of the present invention are passaged in a 12-well plate at a density of $5\times10^5$ cells/well followed by culturing at 37° C. under 5% $CO_2$ and 95% air for 2 days.

(3) Labeled Ligands

Aqueous solutions of ligands labeled with commercially available [$^3$H], [$^{125}$I], [$^{14}$C], [$^{35}$S], etc. are stored at 4° C. or −20° C., and diluted to 1 μM with the measurement buffer.

(4) Standard Ligand Solution

The ligand is dissolved in and adjusted to 1 mM with PBS containing 0.1% bovine serum albumin (manufactured by Sigma Co.) and stored at −20° C.

2. Measurement Method (1) CHO cells expressing the receptor protein of the present invention are cultured in a 12-well culture plate and washed twice with 1 ml of the measurement buffer, and 490 μl of the measurement buffer is added to each well.

(2) After adding 5 μl of $10^{-3}$-$10^{-10}$ M test compound solution, 5 μl of a labeled ligand is added to the mixture, and the cells are incubated at room temperature for an hour. To determine the amount of the non-specific binding, 5 μl of the non-labeled ligand is added in place of the test compound.

(3) The reaction solution is removed, and the wells are washed 3 times with the washing buffer. The labeled ligand bound to the cells is dissolved in 0.2N NaOH-1% SDS, and mixed with 4 ml of liquid scintillator A (manufactured by Wako Pure Chemical Industries, Ltd.)

(4) The radioactivity is measured using a liquid scintillation counter (manufactured by Beckman Co.), and the percent maximum binding (PMB) is calculated by the equation below.

$$PMB=[(B-NSB)/(B_0-NSB)]\times100$$

PMB: Percent maximum binding

B: Value obtained in the presence of a test compound

NSB: Non-specific binding $B_0$: Maximum binding

The compounds or their salts, which are obtainable using the screening methods or the screening kits of the present invention, are the compounds that alter the binding property between ligands and the receptor protein etc. of the present invention. Specifically, these compounds are: (a) compounds that have the G protein-coupled receptor-mediated cell-stimulating activity (e.g., activity that promotes or inhibits arachidonic acid release, acetylcholine release, intracellular $Ca^{2+}$ release, intracellular cAMP production, intracellular cAMP suppression, intracellular cGMP production, inositol phosphate production, changes in cell membrane potential, phosphorylation of intracellular proteins, activation of c-fos, pH reduction, etc.) (so-called agonists to the receptor protein of the present invention); (b) compounds having no cell stimulating-activity (so-called antagonists to the receptor protein of the present invention); (c) compounds that increase the binding affinity between ligands and the G protein-coupled receptor protein of the present invention; and (d) compounds that reduce the binding affinity between ligands and the G protein-coupled receptor protein of the present invention.

The compounds may be peptides, proteins, non-peptide compounds, synthetic compounds, fermentation products, and may be novel or known compounds.

Since agonists to the receptor protein etc. of the present invention have the same physiological activities as those of the ligands for the receptor protein etc. of the present invention, the agonists are useful as safe and low toxic drugs, correspondingly to the ligand activities.

Since antagonists to the receptor protein etc. of the present invention can suppress the physiological activities of ligands for the receptor protein etc. of the present invention, the antagonists are useful as safe and low toxic drugs that inhibit the ligand activities.

The compounds that increase the binding affinity between ligands and the G protein-coupled receptor protein of the present invention are useful as safe and low toxic drugs to potentiate the physiological activities that the ligands for the receptor protein etc. of the present invention possess.

The compounds that reduce the binding affinity between ligands and the G protein-coupled receptor protein of the present invention are useful as safe and low toxic drugs that decrease the physiological activities of ligands for the receptor protein etc. of the present invention.

When compounds or their salt forms, which are obtainable by the screening methods or using the screening kits of the present invention, are employed as pharmaceutical compositions described above, the compounds can be formulated in the drugs in a conventional manner. For example, the compounds can be prepared into tablets, capsules, elixir, microcapsules, aseptic solution, suspension, etc., as described for drugs containing the receptor protein of the present invention.

The drug products thus obtained are safe and low toxic, and can be administered to, for example, human and mammals (e.g., rats, mice, rabbits, sheep, swine, bovine, cats, dogs, monkeys, etc.).

The dose of the compounds or their salt forms varies depending on subject to be administered, target organs, conditions, routes for administration, etc.; in oral administration, e.g., for the patient with cancer, the dose is normally about 0.1 mg to about 100 mg, preferably about 1.0 to about 50 mg, and more preferably about 1.0 to about 20 mg per day (as 60 kg body weight). In parenteral administration, the single dose varies depending on subject to be administered, target organ, conditions, routes for administration, etc. but it is advantageous, e.g., for the patient with cancer, to administer the active ingredient intravenously in a daily dose of about 0.01 to about 30 mg, preferably about 0.1 to about 20 mg, and more preferably about 0.1 to about 10 mg (as 60 kg body weight). For other animal species, the corresponding dose as converted per 60 kg body weight can be administered.

(8) Prophylactic and/or Therapeutic Agents for Various Diseases Comprising the Compounds (Agonists or Antagonists) that Alter the Binding Property Between the G Protein-Coupled Receptor Protein of the Present Invention and Ligands As described above, the receptor protein of the present invention may play some important role in the body such as a role in the central function, circulatory function and alimentary function. Therefore, the compounds (agonists or antagonists) that alter the binding property between the G protein-coupled receptor protein of the present invention and ligands to the receptor protein of the present invention can be used as prophylactic and/or therapeutic agents for diseases associated with dysfunction of the receptor protein of the present invention.

When the compounds and the ligand are used as the prophylactic and/or therapeutic agents for diseases associated with dysfunction of the receptor protein of the present invention, the pharmaceutical preparations can be obtained in a conventional manner.

For example, the compounds and the ligand can be administered orally as sugar coated tablet, capsule, elixir, and microcapsule, or non-orally as injection such as aseptic solution or suspension in water or other pharmaceutically acceptable liquid. For example, preparations of the compounds can be manufactured by mixing with physiologically acceptable known carrier, flavor, filler, vehicle, antiseptic, stabilizer, and binder in a unit-dosage form required for generally approved drug preparation. The amount of the active ingredient is set to an appropriate volume within the specified range.

For the additive miscible with tablets, capsules, etc., for example, binders such as gelatin, cornstarch, tragacanth, and acacia, fillers such as crystalline cellulose, imbibers such as cornstarch, gelatin, and alginic acid, lubricants such as magnesium stearate, sweeteners such as sucrose and saccharin, and flavors such as peppermint, akamono oil and cherry are used. When the dosage form is a capsule, liquid carrier such as fat and oil may be contained. Aseptic compositions for injection can be formulated following the usual preparation such as dissolving or suspending the active substance in vehicle, e.g., water for injection, and natural plant oils e.g., sesame oil and coconut oil. For the aqueous solution for injection, for example, physiological saline and isotonic solutions (e.g., D-sorbitol, D-mannitol, sodium hydrochloride) containing glucose and other adjuvant are used. Appropriate dissolution-assisting agents, for example, alcohol (e.g., ethanol), polyalcohol (e.g., propylene glycol, polyethylene glycol), nonionic surfactant (e.g., polysorbate 80™, HCO-50) may be combined. For the oily solution, for example, sesame oil and soybean oil are used, and dissolution-assisting agents such as benzyl benzoate and benzyl alcohol may be combined.

The prophylactic/therapeutic agents described above may be combined, for example, with buffers (e.g., phosphate buffer, sodium acetate buffer), soothing agents (e.g., benzalkonium chloride, procaine hydrochloride), stabilizers (e.g., human serum albumin, polyethylene glycol), preservatives (e.g., benzyl alcohol, phenol), and antioxidants. The preparation for injection is usually filled in appropriate ampoules.

In addition, the prophylactic/therapeutic agent described above can be used in combination with an appropriate pharmaceutical, as, for example, DDS formulation preparation, to which organs or tissues that highly express the receptor protein of the present invention are specifically targeted.

The preparations obtained as described above are safe and low toxic, and can be administered to, for example, human and mammals (e.g., rats, mice, rabbits, sheep, swine, bovine, cats, dogs, monkeys, etc.).

The dose of the compounds or their salt forms varies depending on subject to be administered, target organs, conditions, routes for administration, etc.; in oral administration, e.g., for the patient with cancer, the dose is normally about 0.1 mg to about 100 mg, preferably about 1.0 to about 50 mg, and more preferably about 1.0 to about 20 mg per day (as 60 kg body weight). In parenteral administration, the single dose varies depending on subject to be administered, target organ, conditions, routes for administration, etc. but it is advantageous, e.g., for the patient with cancer, to administer the active ingredient intravenously in a daily dose of about 0.01 to about 30 mg, preferably about 0.1 to about 20 mg, and more preferably about 0.1 to about 10 mg (as 60 kg body weight). For other animal species, the corresponding dose as converted per 60 kg body weight can be administered.

(9) Quantification of the Receptor Protein of the Present Invention, Its Partial Peptide, or its Salt Form The antibodies of the present invention are capable of specifically recognizing the receptor protein etc. of the present invention. Therefore, the antibodies can be used to quantify the receptor protein etc. of the present invention in a test fluid, especially for quantification by the sandwich immunoassay. That is, the present invention provides, for example, the following quantification methods:

(i) A method of quantifying the receptor protein etc. of the present invention in a test fluid, which comprises competitively reacting the antibody of the present invention with the test fluid and a labeled form of the receptor protein etc. of the present invention, and measuring the ratio of the labeled receptor protein etc. bound to the antibody; and, (ii) A method of quantifying the receptor protein etc. of the present invention in a test fluid, which comprises reacting the test fluid with the antibody of the present invention immobilized on a carrier and a labeled form of the antibody of the present invention simultaneously or sequentially, and measuring the activity of the label on the immobilized carrier.

In (ii) described above, it is preferred that one antibody recognizes the N-terminal region of the receptor protein etc. of the present invention, and another antibody reacts with the C-terminal region of the receptor protein etc. of the present invention.

Using monoclonal antibodies to the receptor protein etc. of the present invention (hereinafter sometimes referred to as the monoclonal antibodies of the present invention), the receptor protein etc. of the present invention can be assayed and also detected by tissue staining or the like. For this purpose, an antibody molecule itself may be used, or $F(ab')_2$, Fab' or Fab fractions of the antibody molecule may also be used. Assay methods using antibodies to the receptor protein etc. of the present invention are not particularly limited. Any assay method can be used, so long as the amount of antibody, antigen, or antibody-antigen complex corresponding to the amount of antigen (e.g., the amount of the receptor protein) in the test fluid can be detected by chemical or physical means and the amount of the antigen can be calculated from a standard curve prepared from standard solutions containing known amounts of the antigen. For example, nephrometry, competitive methods, immunometric method, and sandwich method are appropriately used, with the sandwich method described below being most preferable in terms of sensitivity and specificity.

As the labeling agent for the methods using labeled substances, there are employed, for example, radioisotopes, enzymes, fluorescent substances, luminescent substances, etc. For the radioisotope, for example, [$^{125}$I], [$^{131}$I], [$^{3}$H] and [$^{14}$C] are used. As the enzyme described above, stable enzymes with high specific activity are preferred; for example, β-galactosidase, β-glucosidase, alkaline phosphatase, peroxidase, malate dehydrogenase and the like are used. Example of the fluorescent substance used are fluorescamine and fluorescein isothiocyanate are used. For the luminescent substance, for example, luminol, luminol derivatives, luciferin, and lucigenin. Furthermore, the biotin-avidin system may be used for binding antibody or antigen to the label.

For immobilization of antigen or antibody, physical adsorption may be used. Chemical binding methods conventionally used for insolubilization or immobilization of proteins or enzymes may also be used. For the carrier, for example, insoluble polysaccharides such as agarose, dextran, cellulose, etc.; synthetic resin such as polystyrene, polyacrylamide, silicon, etc., and glass or the like are used.

In the sandwich method, the immobilized monoclonal antibody of the present invention is reacted with a test fluid (primary reaction), then with the labeled monoclonal antibody of the present invention (secondary reaction), and the activity of the label on the immobilizing carrier is measured, whereby the amount of the receptor protein of the present invention in the test fluid can be quantified. The order of the primary and secondary reactions may be reversed, and the reactions may be performed simultaneously or with an interval. The methods of labeling and immobilization can be performed by the methods described above. In the immunoassay by the sandwich method, the antibody used for immobilized or labeled antibodies is not necessarily one species, but a mixture of two or more species of antibody may be used to increase the measurement sensitivity.

In the methods of assaying the receptor protein etc. of the present invention by the sandwich method, antibodies that bind to different sites of the receptor protein etc. are preferably used as the monoclonal antibodies of the present invention for the primary and secondary reactions. That is, in the antibodies used for the primary and secondary reactions are, for example, when the antibody used in the secondary reaction recognizes the C-terminal region of the receptor protein, it is preferable to use the antibody recognizing the region other than the C-terminal region for the primary reaction, e.g., the antibody recognizing the N-terminal region.

The monoclonal antibodies of the present invention can be used for the assay systems other than the sandwich method, for example, competitive method, immunometric method, nephrometry, etc. In the competitive method, antigen in a test fluid and the labeled antigen are competitively reacted with antibody, and the unreacted labeled antigen (F) and the labeled antigen bound to the antibody (B) are separated (B/F separation). The amount of the label in B or F is measured, and the amount of the antigen in the test fluid is quantified. This reaction method includes a liquid phase method using a soluble antibody as an antibody, polyethylene glycol for B/F separation and a secondary antibody to the soluble antibody, and an immobilized method either using an immobilized antibody as the primary antibody, or using a soluble antibody as the primary antibody and immobilized antibody as the secondary antibody.

In the immunometric method, antigen in a test fluid and immobilized antigen are competitively reacted with a definite amount of labeled antibody, the immobilized phase is separated from the liquid phase, or antigen in a test fluid and an excess amount of labeled antibody are reacted, immobilized antigen is then added to bind the unreacted labeled antibody to the immobilized phase, and the immobilized phase is separated from the liquid phase. Then, the amount of the label in either phase is measured to quantify the antigen in the test fluid.

In the nephrometry, insoluble precipitate produced after the antigen-antibody reaction in gel or solution is quantified. When the amount of antigen in the test fluid is small and only a small amount of precipitate is obtained, laser nephrometry using scattering of laser is advantageously employed.

For applying these immunological methods to the measurement methods of the present invention, any particular conditions or procedures are not required. Systems for measuring the receptor protein of the present invention or its salts are constructed by adding the usual technical consideration in the art to the conventional conditions and procedures. For the details of these general technical means, reference can be made to the following reviews and texts. [For example, Hiroshi Irie, ed. "Radioimmunoassay" (Kodansha, published in 1974), Hiroshi Irie, ed. "Sequel to the Radioimmunoassay" (Kodansha, published in 1979), Eiji Ishikawa, et al. ed. "Enzyme immonoassay" (Igakushoin, published in 1978), Eiji Ishikawa, et al. ed. "Immunoenzyme assay" (2nd ed.) (Igakushoin, published in 1982), Eiji Ishikawa, et al. ed. "Immunoenzyme assay" (3rd ed.) (Igakushoin, published in 1987), Methods in ENZYMOLOGY, Vol. 70 (Immunochemical Techniques (Part A)), ibid., Vol. 73 (Immunochemical Techniques (Part B)), ibid., Vol. 74 (Immunochemical Techniques (Part C)), ibid., Vol. 84 (Immunochemical Techniques (Part D: Selected Immunoassays)), ibid., Vol. 92 (Immunochemical Techniques (Part E:

Monoclonal Antibodies and General Immunoassay Methods)), ibid., Vol. 121 (Immunochemical Techniques (Part I: Hybridoma Technology and Monoclonal Antibodies))(all published by Academic Press Publishing).

As described above, the receptor protein of the present invention or its salts can be quantified with high sensitivity, using the antibodies of the present invention.

By quantifying the receptor protein of the present invention or its salts in vivo using the antibodies of the present invention, diagnosis can be made on various diseases associated with dysfunction of the receptor protein of the present invention.

The antibodies of the present invention can also be used for specifically detecting the receptor protein etc. of the present invention present in test samples such as body fluids or tissues. The antibodies may also be used for preparation of antibody columns for purification of the receptor protein etc. of the present invention, for detection of the receptor protein etc. of the present invention in each fraction upon purification, and for analysis of the behavior of the receptor protein of the present invention in the test cells.

(10) Methods of Screening Compounds that Alter the Amount of the Receptor Protein of the Present Invention or its Partial Peptide in Cell Membranes Since the antibodies of the present invention specifically recognize the receptor protein, its partial peptide, or its salt of the present invention, the antibodies can be used for screening of the compounds that alter the amount of the receptor protein of the present invention or its partial peptide in cell membranes.

That is, the present invention provides, for example, the following methods:

(i) A method of screening compounds that alter the amount of the receptor protein of the present invention or its partial peptides in cell membranes, which comprises disrupting (a) blood, (b) specific organs, (c) tissues or cells isolated from the organs of non-human mammals, isolating the cell membrane fraction and then quantifying the receptor protein of the present invention or its partial peptide contained in the cell membrane fraction;

(ii) A method of screening compounds that alter the amount of the receptor protein of the present invention or its partial peptides in cell membranes, which comprises disrupting transformants, etc. expressing the receptor protein of the present invention or its partial peptides, isolating the cell membrane fraction, and then quantifying the receptor protein of the present invention or its partial peptides contained in the cell membrane fraction;

(iii) A method of screening compounds that alter the amount of the receptor protein of the present invention or its partial peptides in cell membranes, which comprises sectioning (a) blood, (b) specific organs, (c) tissues or cells isolated from the organs of non-human mammals, immunostaining, and then quantifying the staining intensity of the receptor protein in the cell surface layer to confirm the protein on the cell membrane; and, (iv) A method of screening compounds that alter the amount of the receptor protein of the present invention or its partial peptides in cell membranes, which comprises sectioning transformants, etc. expressing the receptor protein of the present invention or its partial peptides, immunostaining, and then quantifying the staining intensity of the receptor protein in the cell surface layer to confirm the protein on the cell membrane.

Specifically, the receptor protein and its partial peptides of the present invention contained in cell membrane fractions are quantified as follows.

(i) Normal or non-human mammals of disease models (e.g., mice, rats, rabbits, sheep, swine, bovine, cats, dogs, monkeys, more specifically, rats with dementia, obese mice, rabbits with arteriosclerosis, tumor-bearing mice, etc.) are administered with a drug (e.g., anti-dementia agents, hypotensive agents, anticancer agents, antiobestic agents) or physical stress (e.g., soaking stress, electric shock, light and darkness, low temperature, etc.), and the blood, specific organs (e.g., brainlung, large intestine, etc.), or tissue or cells isolated from the organs are obtained after a specified period of time. The obtained organs, tissues or cells are suspended in, for example, an appropriate buffer (e.g., Tris hydrochloride buffer, phosphate buffer, Hepes buffer), and the organs, tissues, or cells are disrupted, and the cell membrane fraction is obtained using surfactants (e.g., Triton-X100™, Tween 20™) and further using techniques such as centrifugal separation, filtration, and column fractionation.

The cell membrane fraction refers to a fraction abundant in cell membrane obtained by cell disruption and subsequent fractionation by a publicly known method. Useful cell disruption methods include cell squashing using a Potter-Elvehjem homogenizer, disruption using a Waring blender or Polytron (manufactured by Kinematica Inc.), disruption by ultrasonication, and disruption by cell spraying through thin nozzles under an increased pressure using a French press or the like. Cell membrane fractionation is effected mainly by fractionation using a centrifugal force, such as centrifugation for fractionation and density gradient centrifugation. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in the receptor protein etc. expressed and membrane components such as cell-derived phospholipids and membrane proteins.

The receptor protein of the present invention or its partial peptides contained in the cell membrane fraction can be quantified by, for example, the sandwich immunoassay and western blot analysis using the antibodies of the present invention.

The sandwich immunoassay can be performed as described above, and the western blot can be performed by publicly known methods.

(ii) Transformants expressing the receptor protein of the present invention or its partial peptides are prepared following the method described above, and the receptor protein of the present invention or its partial peptides contained in the cell membrane fraction can be quantified.

The compounds that alter the amount of the receptor protein of the present invention or its partial peptides in cell membranes can be screened as follows.

(i) To normal or disease models of non-human mammals, a test compound is administered at a specified period of time before (30 minutes to 24 hours before, preferably 30 minutes to 12 hours before, more preferably 1 hour to 6 hours before), at a specified time after (30 minutes to 3 days after, preferably 1 hour to 2 days after, more preferably 1 hour to 24 hours after), or simultaneously with a drug or physical stress. At a specified time (30 minute to 3 days, preferably 1 hour to 2 days, more preferably 1 hour to 24 hours) after administration of the test compound, the amount of the receptor protein of the present invention or its partial peptides contained in cell membranes are quantified.

(ii) Transformants are cultured in a conventional manner and a test compound is mixed in the culture medium. After a specified time (after 1 day to 7 days, preferably after 1 day to 3 days, more preferably after 2 to 3 days), the amount of the receptor protein of the present invention or its partial peptides contained in the cell membranes can be quantified.

Specifically, the receptor protein of the present invention or its partial peptides contained in cell membrane fractions are confirmed as follows.

(iii) Normal or non-human mammals of disease models (e.g., mice, rats, rabbits, sheep, swine, bovine, cats, dogs, monkeys, more specifically, rats with dementia, obese mice, rabbits with arteriosclerosis, tumor-bearing mice, etc.) are administered with a drug (e.g., anti-dementia agents, hypotensive agents, anticancer agents, antiobestic agents) or physical stress (e.g., soaking stress, electric shock, light and darkness, low temperature, etc.), and the blood, specific organs (e.g., brain, lung, large intestine, etc.), or tissue or cells isolated from the organs are obtained after a specified period of time. Tissue sections are prepared from the thus obtained organs, tissues or cells in a conventional manner followed by immunostaining with the antibody of the present invention. The staining intensity of the receptor protein in the cell surface layer is quantified to confirm the protein on the cell membrane, the amount of the receptor protein of the present invention or its partial peptides in the cell membrane can be quantitatively or qualitatively confirmed.

(iv) The confirmation can also be made by the similar method, using transformants expressing the receptor protein of the present invention or its partial peptides.

The compounds or its salts, which is obtainable by the screening methods of the present invention, are the compounds that alter the amount of the receptor protein or its peptide fragments of the present invention. Specifically, these compounds are; (a) compounds that potentiate the G protein-coupled receptor-mediated cell-stimulating activity (e.g., activity that promotes or inhibits arachidonic acid release, acetylcholine release, intracellular $Ca^{2+}$ release, intracellular cAMP production, intracellular cAMP suppression, intracellular cGMP production, inositol phosphate production, changes in cell membrane potential, phosphorylation of intracellular proteins, activation of c-fos, pH reduction, etc.) (so-called agonists to the receptor protein of the present invention), by increasing the amount of the receptor protein of the present invention or its partial peptides; and (b) compounds that lower the cell stimulating-activity by decreasing the amount of the receptor protein of the present invention.

The compounds may be peptides, proteins, non-peptide compounds, synthetic compounds, fermentation products, and may be novel or known compounds.

The compounds that increase the cell-stimulating activity are useful as safe and low toxic drugs for potentiation of the physiological activity of the receptor protein etc. of the present invention.

The compounds that decrease the cell-stimulating activity are useful as safe and low toxic drugs for reduction of the physiological activity of the receptor protein etc. of the present invention.

When compounds or their salt forms, which are obtainable by the screening methods of the present invention, are used as for pharmaceutical compositions, preparations can be prepared following the conventional methods. For example, as described above for preparation of the pharmaceuticals containing the receptor protein of the present invention, the compounds can be prepared into tablets, capsules, elixir, microcapsules, aseptic solution, suspension, etc.

Since the preparations thus obtained are safe and low toxic, the preparations can be administered to human and mammals (e.g., rats, mice, rabbits, sheep, swine, bovine, cats, dogs, monkeys, etc.).

The dose of the compounds or their salt forms varies depending on subject to be administered, target organs, conditions, routes for administration, etc.; in oral administration, e.g., for the patient with cancer, the dose is normally about 0.1 mg to about 100 mg, preferably about 1.0 to about 50 mg, and more preferably about 1.0 to about 20 mg per day (as 60 kg body weight). In parenteral administration, the single dose varies depending on subject to be administered, target organ, conditions, routes for administration, etc. but it is advantageous, e.g., for the patient with cancer, to administer the active ingredient intravenously in a daily dose of about 0.01 to about 30 mg, preferably about 0.1 to about 20 mg, and more preferably about 0.1 to about 10 mg (as 60 kg body weight). For other animal species, the corresponding dose as converted per 60 kg body weight can be administered.

(11) Prophylactic and/or Therapeutic Agents for Various Diseases Comprising Compounds That Alter the Amount of the Receptor Protein of the Present Invention or Its Partial Peptides in Cell Membrane As described above, the receptor protein of the present invention is considered to play some important role in vivo, such as a role in the central function. Therefore, the compounds that alter the amount of the receptor protein of the present invention or its partial peptide in cell membrane can be used as prophylactic and/or therapeutic agents for diseases associated with dysfunction of the receptor protein of the present invention.

When the compounds are used as prophylactic and/or therapeutic agents for diseases associated with dysfunction of the receptor protein of the present invention, the preparations can be obtained in a conventional manner.

For example, the compounds can be administered orally as a sugar coated tablet, capsule, elixir, and microcapsule, or parenterally as injection such as aseptic solution and suspension in water or other pharmaceutically acceptable liquid. For example, preparations of the compounds can be manufactured by mixing with physiologically acceptable known carrier, flavor, filler, vehicle, antiseptic, stabilizer, and binder in a unit-dosage form required for generally approved drug preparation. The amount of the active ingredient is set to an appropriate volume within the specified range.

For the additive miscible with tablets and capsules, for example, binders such as gelatin, cornstarch, tragacanth, and acacia, fillers such as crystalline cellulose, imbibers such as cornstarch, gelatin, and alginic acid, lubricants such as magnesium stearate, sweeteners such as sucrose and saccharin, and flavors such as peppermint, akamono oil and cherry are used. When the dosage form is a capsule, liquid carrier such as fat and oil may be contained. Aseptic compositions for injection can be formulated following the usual preparation such as dissolving or suspending the active substance in vehicle, e.g., water for injection, and natural plant oils e.g., sesame oil and coconut oil. For the aqueous solution for injection, for example, physiological saline and isotonic solutions (e.g., D-sorbitol, D-mannitol, sodium hydrochloride) containing glucose and other adjuvant are used. Appropriate dissolution-assisting agents, for example, alcohol (e.g., ethanol), polyalcohol (e.g., propylene glycol, polyethylene glycol), nonionic surfactant (e.g., polysorbate 80™, HCO-50) may be combined. For the oily solution, for example, sesame oil and soybean oil are used, and dissolution-assisting agents such as benzyl benzoate and benzyl alcohol may be combined.

The prophylactic/therapeutic agents described above may be combined with buffers (e.g., phosphate buffer, sodium acetate buffer), soothing agents (e.g., benzalkonium chloride, procaine hydrochloride), stabilizers (e.g., human serum albumin, polyethylene glycol), preservatives (e.g., benzyl alcohol, phenol), and antioxidants. The preparation for injection is usually filled in appropriate ampoules.

Since the preparations thus obtained are safe and low toxic, the preparation can be administered to, for example, human and mammals (e.g., rats, mice, rabbits, sheep, swine, bovine, cats, dogs, monkeys, etc.).

The dose of the compounds or their salt forms varies depending on subject to be administered, target organs, conditions, routes for administration, etc.; in oral administration, e.g., for the patient with cancer, the dose is normally about 0.1 mg to about 100 mg, preferably about 1.0 to about 50 mg, and more preferably about 1.0 to about 20 mg per day (as 60 kg body weight). In parenteral administration, the single dose varies depending on subject to be administered, target organ, conditions, routes for administration, etc. but it is advantageous, e.g., for the patient with cancer, to administer the active ingredient intravenously in a daily dose of about 0.01 to about 30 mg, preferably about 0.1 to about 20 mg, and more preferably about 0.1 to about 10 mg (as 60 kg body weight). For other animal species, the corresponding dose as converted per 60 kg body weight can be administered.

(12) Neutralization by Antibodies to the Receptor Protein, Its Partial Peptides, or their Salts of the Present Invention The neutralizing activity of antibodies to the receptor protein of the present invention, its partial peptides, or its salts refer to an activity of inactivating the signal transduction function involving the receptor protein. Therefore, when the antibody has the neutralizing activity, the antibody can inactivate the signal transduction in which the receptor protein participates, for example, inactivate the receptor protein-mediated cell-stimulating activity (e.g., activity that promotes or inhibits arachidonic acid release, acetylcholine release, intracellular $Ca^{2+}$ release, intracellular cAMP production, intracellular cAMP suppression, intracellular cGMP production, inositol phosphate production, changes in cell membrane potential, phosphorylation of intracellular proteins, activation of c-fos, pH reduction, etc.). Therefore, the antibody can be used for the prevention and/or treatment of diseases caused by overexpression of the receptor protein.

(13) Preparation of Animals Carrying the DNA Encoding the G Protein-Coupled Receptor Protein of the Present Invention Using the DNA of the present invention, transgenic animals expressing the receptor protein etc. of the present invention can be prepared. Examples of the animals include mammals (e.g., rats, mice, rabbits, sheep, swine, bovine, cats, dogs, monkeys, etc.) (hereinafter merely referred to as animals) can be used, with mice and rabbits being particularly appropriate.

To introduce the DNA of the present invention to target animals, it is generally advantageous to use the DNA in a gene construct ligated downstream of a promoter that can express the DNA in animal cells. For example, when the DNA of the present invention derived from rabbit is transferred, e.g., the gene construct, in which the DNA is ligated downstream of a promoter that can expresses the DNA of the present invention derived from animals containing the DNA of the present invention highly homologous to the rabbit-derived DNA, is microinjected to rabbit fertilized ova; thus, the DNA-introduced animal, which is capable of producing a high level of the receptor protein etc. of the present invention, can be produced. Examples of the promoters that are usable include virus-derived promoters and ubiquitous expression promoters such as metallothionein promoter, but promoters of NGF gene and enolase that are specifically expressed in the brain are preferably used.

The introduction of the DNA of the present invention at the fertilized egg cell stage secures the presence of the DNA in all germ and somatic cells in the produced animal. The presence of the receptor protein etc. of the present invention in the germ cells in the DNA-introduced animal means that all germ and somatic cells contain the receptor protein etc. of the present invention in all progenies of the animal. The progenies of the animal that took over the gene contain the receptor protein etc. of the present invention in all germ and somatic cells.

The DNA-introduced animals of the present invention can be maintained and bled in the conventional environment as animals carrying the DNA after confirming the stable retention of the gene in the animals through mating. Furthermore, mating male and female animals containing the objective DNA results in acquiring homozygous animals having the introduced gene on both homologous chromosomes. By mating the male and female homozygotes, bleeding can be performed so that all progenies contain the DNA.

Since the receptor protein etc. of the present invention is highly expressed in the animals in which the DNA of the present invention has been introduced, the animals are useful for screening of agonists or antagonists to the receptor protein etc. of the present invention.

The animals in which the DNA of the present invention has been introduced can also be used as cell sources for tissue culture. The receptor protein of the present invention can be analyzed by, for example, directly analyzing the DNA or RNA in tissues from the mouse in which the DNA of the present invention has been introduced, or by analyzing tissues containing the receptor protein etc. expressed from the gene. Cells from tissues containing the receptor protein etc. of the present invention are cultured by the standard tissue culture technique. Using these cells, for example, the function of tissue cells such as cells derived from the brain or peripheral tissues, which are generally difficult to culture, can be studied. Using these cells, for example, it is possible to select pharmaceuticals that increase various tissue functions. When a highly expressing cell line is available, the receptor protein etc. of the present invention can be isolated and purified from the cell line.

(14) Knockout Animal

The present invention provides a non-human mammal embryonic stem cell bearing the DNA of the present invention inactivated and a non-human mammal deficient in expressing the DNA of the present invention.

Thus, the present invention provides:

(1) A non-human mammal embryonic stem cell in which the DNA of the present invention is inactivated;

(2) The embryonic stem cell according to (1), wherein the DNA is inactivated by introducing a reporter gene (e.g., β-galactosidase gene derived from *Escherichia coli*);

(3) The embryonic stem cell according to (1), which is resistant to neomycin;

(4) The embryonic stem cell according to (1), wherein the non-human mammal is a rodent;

(5) An embryonic stem cell according to (4), wherein the rodent is mouse;

(6) A non-human mammal deficient in expressing the DNA of the present invention, wherein the DNA of the present invention is inactivated;

(7) The non-human mammal according to (6), wherein the DNA is inactivated by inserting a reporter gene (e.g., β-galactosidase derived from *Escherichia coli*) therein and the reporter gene is capable of being expressed under control of a promoter for the DNA of the present invention;

(8) The non-human mammal according to (6), which is a rodent;

(9) The non-human mammal according to (8), wherein the rodent is mouse; and,

(10) A method for screening a compound or its salt that promotes or inhibits the promoter activity for the DNA of the present invention, which comprises administering a test compound to the mammal of (7) and detecting expression of the reporter gene.

The non-human mammalian embryonic stem cell, in which the DNA of the present invention is inactivated, refers to a non-human mammalian embryonic stem cell that suppresses the ability of the non-human mammalian to express the DNA by artificially mutating the DNA of the present invention possessed in the non-human mammal, or the DNA has no substantial ability to express the polypeptide of the present invention (hereinafter sometimes referred to as the knockout DNA of the present invention) by substantially inactivating the activities of the polypeptide of the present invention encoded by the DNA (hereinafter merely referred to as ES cell).

As the non-human mammalian, the same examples as described above apply.

Techniques for artificially mutating the DNA of the present invention include deletion of a part or all of the DNA sequence and insertion of or substitution with other DNA, e.g., by genetic engineering. By these variations, the knockout DNA of the present invention may be prepared, for example, by shifting the reading frame of a codon or by disrupting the function of a promoter or exon.

Specifically, the non-human mammalian embryonic stem cell, in which the DNA of the present invention is inactivated (hereinafter merely referred to as the ES cell with the DNA of the present invention inactivated or the knockout ES cell of the present invention), can be obtained by, for example, isolating the DNA of the present invention possessed by the target non-human mammal, inserting a DNA strand (hereinafter simply referred to as targeting vector) having a DNA sequence constructed so as to eventually destroy the gene by inserting into its exon site a chemical resistant gene such as a neomycin resistant gene or a hygromycin resistant gene, or a reporter gene such as lacZ (β-galactosidase gene) or cat (chloramphenicol acetyltransferase gene), etc. thereby to destroy the functions of exon, or by inserting into the intron site between exons a DNA sequence which terminates gene transcription (e.g., polyA-added signal, etc.) thereby to disable the synthesis of complete messenger RNA, into a chromosome of the animal cells by, e.g., homologous recombination. The thus-obtained ES cells are analyzed by the Southern hybridization using as a probe a DNA sequence on or near the DNA of the present invention, or by PCR using as primers a DNA sequence on the targeting vector and another DNA sequence near the DNA of the present invention which is not included in the targeting vector, and the knockout ES cell of the present invention is selected.

The parent ES cells to inactivate the DNA of the present invention by homologous recombination, etc. may be of a strain already established as described above, or may be originally established in accordance with a modification of the known method by Evans and Kaufman supra. For example, in the case of mouse ES cells, currently it is common practice to use ES cells of the 129 strain. However, since their immunological background is obscure, the C57BL/6 mouse or the $BDF_1$ mouse ($F_1$ hybrid between C57BL/6 and DBA/2), wherein the low ovum collection per C57BL/6 mouse or C57BL/6 has been improved by crossing with DBA/2, may be preferably used, instead of obtaining a pure line of ES cells with the clear immunological genetic background. The $BDF_1$ mouse is advantageous in that, when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocytes of 3.5 days after fertilization are commonly used. A large number of early stage embryos may be acquired more efficiently, by collecting the embryos of the 8-cell stage and using the same after culturing until the blastocyte stage.

Although the ES cells used may be of either sex, male ES cells are generally more convenient for generation of a germ cell line chimera and are therefore preferred. It is desirable to identify sexes as soon as possible also in order to save painstaking culture time.

As an example of the method for sex identification of the ES cell, mention may be made of a method in which a gene in the sex-determining region on the Y-chromosome is amplified by PCR and detected. When this method is used, ES cells (about 50 cells) corresponding to almost 1 colony are sufficient, whereas karyotype analysis hitherto required about $10^6$ cells; therefore, the first selection of ES cells at the early stage of culture can be based on sex identification, and male cells can be selected early, which saves a significant amount of time at the early stage of culture.

Second selection can be achieved by, for example, number of chromosome confirmation by the G-banding method. It is usually desirable that the chromosome number of the obtained ES cells be 100% of the normal number. However, when it is difficult to obtain the cells having the normal number of chromosomes due to physical operation etc. in cell establishment, it is desirable that the ES cell be again cloned to a normal cell (e.g., in mouse cells having the number of chromosomes being 2n=40) after the gene of the ES cells is rendered knockout.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably about 5% carbon dioxide and about 95% air, or about 5% oxygen, about 5% carbon dioxide and about 90% air) in the presence of LIF (1-10000 U/ml) on appropriate feeder cells such as STO fibroblasts, treated with a trypsin/EDTA solution (normally about 0.001 to about 0.5% trypsin/about 0.1 to 5 mM EDTA, preferably about 0.1% trypsin/about 1 mM EDTA) at the time of passage to obtain separate single cells, which are then seeded on freshly prepared feeder cells. This passage is normally conducted every 1 to 3 days; it is desirable that cells be observed at passage and cells found to be morphologically abnormal in culture, if any, be abandoned.

By allowing ES cells to reach a high density in monolayers or to form cell aggregates in suspension under appropriate conditions, it is possible to differentiate them to various cell types, for example, parietal and visceral muscles, cardiac muscle or the like [M. J. Evans and M. H. Kaufman, Nature, 292, 154, 1981; G. R. Martin, Proc. Natl. Acad. Sci. U.S.A., 78, 7634, 1981; T. C. Doetschman et al., Journal of Embryology Experimental Morphology, 87, 27, 1985]. The cells deficient in expression of the DNA of the present invention, which are obtainable from the differentiated ES cells of the present invention, are useful for studying the functions of the polypeptide of the present invention in vitro cytologically or molecular biologically.

The non-human mammal deficient in expression of the DNA of the present invention can be identified from a normal animal by measuring the amount of mRNA in the subject animal by a publicly known method, and indirectly comparing the levels of expression.

As the non-human mammal, the same examples supra apply.

With respect to the non-human mammal deficient in expression of the DNA of the present invention, the DNA of the present invention can be made knockout by transfecting a targeting vector, prepared as described above, to mouse embryonic stem cells or mouse oocytes thereof, and conducting homologous recombination in which a targeting vector DNA sequence, wherein the DNA of the present invention is inactivated by the transfection, is replaced with the DNA of the present invention on a chromosome of a mouse embryonic stem cell or mouse oocyte.

The cells, in which the DNA of the present invention is rendered knockout, can be identified by the Southern hybridization analysis using as a probe a DNA sequence on or near the DNA of the present invention, or by PCR analysis using as primers a DNA sequence on the targeting vector and another DNA sequence which is not included in the DNA of the present invention derived from mouse, which is used as the targeting vector. When non-human mammalian embryonic stem cells are used, the cell line wherein the DNA of the present invention is inactivated is cloned by homologous recombination; the resulting cloned cell line is injected to, e.g., a non-human mammalian embryo or blastocyte, at an appropriate stage such as the 8-cell stage. The resulting chimeric embryos are transplanted to the uterus of the pseudo-pregnant non-human mammal. The resulting animal is a chimeric animal composed of both cells having the normal locus of the DNA of the present invention and those having an artificially mutated locus of the DNA of the present invention.

When some germ cells of the chimeric animal have a mutated locus of the DNA of the present invention, an individual, in which all tissues are composed of cells having an artificially mutated locus of the DNA of the present invention, can be selected from a series of offspring obtained by crossing between such a chimeric animal and a normal animal, e.g., by coat color identification, etc. The individuals thus obtained are normally deficient in heterozygous expression of the polypeptide of the present invention. The individuals deficient in homozygous expression of the polypeptide of the present invention can be obtained from offspring of the intercross between the heterozygotes.

When an oocyte is used, a DNA solution may be injected, e.g., to the prenucleus by microinjection thereby to obtain a transgenic non-human mammal having a targeting vector introduced into its chromosome. From such transgenic non-human mammals, those having a mutation at the locus of the DNA of the present invention can be obtained by selection based on homologous recombination.

As described above, individuals wherein the DNA of the present invention is rendered knockout permit passage rearing under ordinary rearing conditions, after it is confirmed that in the animal individuals obtained by their crossing, the DNA has been knockout.

Furthermore, the genital system may be obtained and maintained by conventional methods. That is, by crossing male and female animals each having the inactivated DNA, homozygote animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammalian embryonic stem cell, in which the DNA of the present invention is inactivated, is very useful for preparing a non-human mammal deficient in expression of the DNA of the present invention.

Since the non-human mammal, in which the DNA of the present invention fails to express, lacks various biological activities induced by the polypeptide of the present invention, such an animal can be a disease model suspected of inactivated biological activities of the polypeptide of the present invention and thus, offers an effective study to investigate causes for and therapy for these diseases.

(14a) Method for Screening of Compounds Having Therapeutic/Prophylactic Effects for Diseases Caused by Deficiency, Damages, etc. of the DNA of the Present Invention The non-human mammal deficient in expression of the DNA of the present invention can be used to screen the compounds having therapeutic/prophylactic effects for diseases caused by deficiency, damages, and the like of the DNA of the present invention.

That is, the present invention provides a method for screening of a compound or its salt having therapeutic/prophylactic effects for diseases caused by deficiency, damages, etc. of the DNA of the present invention, which comprises administering a test compound to the non-human mammal deficient in expression of the DNA of the present invention, and observing and measuring a change occurred in the animal.

As the non-human mammal deficient in expression of the DNA of the present invention used for the screening method, the same examples as given hereinabove apply.

Examples of the test compounds include peptides, proteins, non-peptide compounds, synthetic compounds, fermentation products, cell extracts, vegetable extracts, animal tissue extracts, blood plasma, etc. and these compounds may be novel compounds or publicly known compounds.

Specifically, the non-human mammal deficient in the expression of the DNA of the present invention is treated with a test compound, comparison is made with an intact animal for control and a change in each organ, tissue, disease conditions, etc. of the animal is used as an indicator to assess the therapeutic/prophylactic effects of the test compound.

For treating an animal to be tested with a test compound, for example, oral administration, intravenous injection, etc. are applied and the treatment is appropriately selected depending upon conditions of the test animal, properties of the test compound, etc. Furthermore, the amount of a test compound administered can be appropriately selected depending on administration route, nature of the test compound, or the like.

For example, in the case of screening a compound having a therapeutic/prophylactic effect for central dysfunction (e.g., Alzheimer's disease, senile dementia, suppression of eating, etc.), endocrine-related diseases (e.g., hypertension, hypogonadism, hypothyroidism, hypopituitarism, etc.), metabolic disorders (e.g., diabetes mellitus, lipid metabolic disorders, hyperlipemia, etc.), cancer (e.g., non-small cell lung carcinoma, cancer of ovary, prostate cancer, stomach cancer, bladder cancer, breast cancer, uterocervical cancer, colon cancer, rectum cancer, etc.), the non-human mammal deficient in expression of the DNA of the present invention is subjected to a sugar loading treatment, a test compound is administered before or after the sugar loading treatment and, blood sugar level, body weight change, etc. of the animal is measured with passage of time.

In the screening method, where the test compound was administered to a test animal, the test compound can be selected as a compound having the prophylactic and/or therapeutic effect against the above-mentioned diseases when metastasis of cancer reduced more than about 10%, preferably more than about 30%, more preferably more than about 50%.

The compound obtained using the screening methods is a compound selected from the test compounds described above and exhibits a therapeutic/prophylactic effect for the diseases caused by deficiencies, damages, etc. of the polypeptide of the present invention. Therefore, the compound can be used as a safe and low toxic drug for the treatment/prevention, etc. for these diseases. Furthermore, compounds derived from such a compound obtained by the screening supra can be used as well.

The compound obtained by the screening above may be in the form of salts. As the salts of the compound, there may be used salts with physiologically acceptable acids (e.g., inorganic acids or organic acids) or bases (e.g., alkali metal salts), preferably physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

A drug containing the compound or salts thereof obtained by the screening methods may be manufactured in a manner similar to the method for preparing the drug containing the polypeptide of the present invention described hereinabove.

Since the pharmaceutical composition thus obtained is safe and low toxic, it can be administered to human and mammal (e.g., rat, mouse, guinea pig, rabbit, sheep, swine, bovine, horse, cat, dog, monkey, etc.).

The dose of the compound or its salt may vary depending on target disease, subject to be administered, route for administration, etc. When the compound is orally administered, the compound is administered to adult patient with cancer (as 60 kg body weight) generally in a daily dose of approximately 0.1 to 100 mg, preferably approximately 1.0 to 50 mg, more preferably approximately 1.0 to 200 mg, and most preferably approximately 1.0 to 20 mg. In parenteral administration, a single dose of the compound may vary depending on subject to be administered, target disease, etc. When the compound is administered to adult patient with cancer (as 60 kg) in the form of injection, it is desired to intravenously administer the compound in the form of injection, generally in a daily dose of approximately 0.01 to 30 mg, preferably approximately 0.1 to 20 mg, and more preferably approximately 0.1 to 10 mg. For other animal species, the corresponding dose as converted per 60 kg weight can be administered.

(14b) Method of Screening a Compound that Promotes or Inhibits the Activities of a Promoter to the DNA of the Present Invention The present invention provides a method of screening a compound or its salt that promotes or inhibits the activities of a promoter to the DNA of the present invention, which comprises administering a test compound to a non-human mammal deficient in expression of the DNA of the present invention and detecting expression of the reporter gene.

In the screening method described above, the non-human mammal deficient in expression of the DNA of the present invention is selected from the aforesaid non-human mammal deficient in expression of the DNA of the present invention for an animal, in which the DNA of the present invention is inactivated by introducing a reporter gene and the reporter gene can be expressed under control of a promoter to the DNA of the present invention.

The same examples given above for the test compound apply to the test compound.

As the reporter gene, the same specific examples given above apply to the reporter gene, with β-galactosidase (lacZ), soluble alkaline phosphatase gene, luciferase gene, etc. being preferred.

In the non-human mammal deficient in expression of the DNA of the present invention wherein the DNA of the present invention is substituted with a reporter gene, the reporter gene is present under control of a promoter to the DNA of the present invention. Thus, the activity of the promoter can be detected by tracing the expression of a substance encoded by the reporter gene.

For example, when a part of the DNA region encoding the polypeptide of the present invention is substituted with, e.g., β-galactosidase gene (lacZ) derived from *Escherichia coli*, β-galactosidase is expressed in a tissue where the polypeptide of the present invention should originally be expressed, in place of the polypeptide of the present invention. Thus, the expression state of the polypeptide of the present invention can be readily observed in vivo of an animal, by staining with a reagent, e.g., 5-bromo-4-chloro-3-indolyl-β-D-galactopyranoside (X-gal), which is a substrate for β-galactosidase. Specifically, a mouse deficient in the polypeptide of the present invention, or its tissue section is fixed with glutaraldehyde, etc. After washing with phosphate buffered saline (PBS), the system is reacted with a staining solution containing X-gal at room temperature or about 37° C. for approximately 30 minutes to an hour. After the β-galactosidase reaction is terminated by washing the tissue preparation with 1 mM EDTA/PBS solution, the color formed is observed. Alternatively, mRNA encoding lacZ may be detected in a conventional manner.

The compound or salts thereof obtained using the screening methods supra are compounds selected from the test compounds described above, which promote or inhibit the promoter activity for the DNA of the present invention.

The compound obtained by the screening methods may be in the form of salts. The salts of the compound used are salts with physiologically acceptable acids (e.g., inorganic acids) or bases (e.g., organic acids), and physiologically acceptable acid addition salts are preferred. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

Since the compounds or salts thereof that promote the promoter activity to the DNA of the present invention can promote the expression of the polypeptide of the present invention, or can promote the functions of the polypeptide, they are useful as drugs for central dysfunction (e.g., Alzheimer's disease, senile dementia, suppression of eating, etc.), endocrine-related diseases (e.g., hypertension, hypogonadism, hypothyroidism, hypopituitarism, etc.), metabolic disorders (e.g., diabetes mellitus, lipid metabolic disorders, hyperlipemia, etc.), cancer (e.g., non-small cell lung carcinoma, cancer of ovary, prostate cancer, stomach cancer, bladder cancer, breast cancer, uterocervical cancer, colon cancer, rectum cancer, etc.).

Since the compounds or salts thereof that inhibit the promoter activity to the DNA of the present invention can inhibit the expression of the polypeptide of the present invention, or can inhibit the functions of the polypeptide, they are useful as drugs such as prophylactic and/or therapeutic agents for central dysfunction (e.g., Alzheimer's disease, senile dementia, suppression of eating, etc.), endocrine-related diseases (e.g., hypertension, hypogonadism, hypothyroidism, hypopituitarism, etc.), metabolic disorders (e.g., diabetes mellitus, lipid metabolic disorders, hyperlipemia, etc.), cancer (e.g., non-small cell lung carcinoma, cancer of ovary, prostate cancer, stomach cancer, bladder cancer, breast cancer, uterocervical cancer, colon cancer, rectum cancer, etc.).

In addition, compound derived from the compounds obtained by the screening above may be employed as well.

A drug containing the compounds or salts thereof obtained by the screening methods supra may be prepared in a manner similar to the method for preparing the drug containing the polypeptide of the present invention or its salts described above.

Since the pharmaceutical preparation thus obtained is safe and low toxic, it can be administered to human and mammal (e.g., rat, mouse, guinea pig, rabbit, sheep, swine, bovine, horse, cat, dog, monkey, etc.).

The dose of the compound or salts thereof varies depending on target disease, subject to be administered, route for administration, etc.; for example, when the compound that promotes the promoter activity to the DNA of the present invention is orally administered, they may be administered to adult patient with cancer (as 60 kg body weight) normally in a daily dose of about 0.1 to about 100 mg, preferably about 1.0 to about 50 mg, more preferably about 1.0 to about 20 mg. In parenteral administration, a single dose of the compound may vary depending upon subject to be administered, target disease, etc.; when the compound that promotes the promoter activity to the DNA of the present invention is administered in the form of injectable preparation, it is advantageous to administer the compound intravenously to adult patient with cancer (as 60 kg) in a daily dose of about 0.01 to about 30 mg, preferably about 0.1 to about 20 mg, more preferably about 0.1 to about 10 mg. For other animal species, the corresponding dose as converted per 60 kg can be administered.

On the other hand, for example, when the compound that inhibits the promoter activity to the DNA of the present invention is orally administered, the compound is administered to adult patient with cancer (as 60 kg body weight) in a daily dose of approximately 0.1 to 100 mg, preferably approximately 1.0 to 50 mg, more preferably approximately 1.0 to 20 mg. In parenteral administration, a single dose of the compound may vary depending on subject to be administered, target disease, etc.; when the compound that inhibits the promoter activity to the DNA of the present invention is administered to adult patient with cancer (as 60 kg) in the form of injectable preparation, it is advantageous to administer the compound intravenously in a daily dose of approximately 0.01 to 30 mg, preferably approximately 0.1 to 20 mg, more preferably approximately 0.1 to 10 mg. For other animal species, the corresponding dose as converted per 60 kg weight can be administered.

As described above, the non-human mammal deficient in expression of the DNA of the present invention is extremely useful for screening a compound that promotes or inhibits the promoter activity of DNA of the present invention, or a salt thereof. Therefore, it can greatly contribute for searching causes of, or developing prophylactic and/or therapeutic agents for various diseases caused by deficiency in expression of the DNA of the present invention.

Further, where so-called transgenic animal (gene-introduced animal) is prepared by using DNA, which contains a promoter region for the polypeptide of the present invention, ligating genes encoding a variety of proteins to downstream thereof and injecting this DNA to animal's egg cell, the peptide can be synthesized specifically, so that it will allow to investigate its intravital function. Furthermore, where the cell line expressing an appropriate reporter gene, which binds to the above-mentioned promoter region, leads to establish, it can be used as a screening system of low molecular weight compound having a function that specifically promotes or inhibits intravital producing ability of the polypeptide of the present invention per se.

In the specification and drawings, the codes of bases and amino acids are denoted in accordance with the IUPAC-IUB Commission on Biochemical Nomenclature or by the common codes in the art, examples of which are shown below. For amino acids that may have the optical isomer, L form is presented unless otherwise indicated.

| | |
|---|---|
| DNA: | deoxyribonucleic acid |
| cDNA: | complementary deoxyribonucleic acid |
| A: | adenine |
| T: | thymine |
| G: | guanine |
| C: | cytosine |
| RNA: | ribonucleic acid |
| mRNA: | messenger ribonucleic acid |
| dATP: | deoxyadenosine triphosphate |
| dTTP: | deoxythymidine triphosphate |
| dGTP: | deoxyguanosine triphosphate |
| dCTP: | deoxycytidine triphosphate |
| ATP: | adenosine triphosphate |
| EDTA: | ethylenediaminetetraacetic acid |
| SDS: | sodium dodecyl sulfate |
| Gly: | glycine |
| Ala: | alanine |
| Val: | valine |
| Leu: | leucine |
| Ile: | isoleucine |
| Ser: | serine |
| Thr: | threonine |
| Cys: | cysteine |
| Met: | methionine |
| Glu: | glutamic acid |
| Asp: | aspartic acid |
| Lys: | lysine |
| Arg: | arginine |
| His: | histidine |
| Phe: | phenylalanine |
| Tyr: | tyrosine |
| Trp: | tryptophan |
| Pro: | proline |
| Asn: | asparagine |
| Gln: | glutamine |
| pGlu: | pyroglutamic acid |
| *: | corresponding stop codon |
| Me: | methyl |
| Et: | ethyl |

-continued

| | |
|---|---|
| Bu: | butyl |
| Ph: | phenyl |
| TC: | thiazolidine-4(R)-carboxamide |

The substituents, protective groups and reagents, which are frequently used throughout the specification, are shown by the following abbreviations.

| | |
|---|---|
| Tos: | p-toluenesulfonyl |
| CHO: | formyl |
| Bzl: | benzyl |
| $Cl_2Bl$: | 2,6-dichlorobenzyl |
| Bom: | benzyloxymethyl |
| Z: | benzyloxycarbonyl |
| Cl-Z: | 2-chlorobenzyloxycarbonyl |
| Br-Z: | 2-bromobenzyloxycarbonyl |
| Boc: | t-butoxycarbonyl |
| DNP: | dinitrophenol |
| Trt: | trityl |
| Bum: | t-butoxymethyl |
| Fmoc: | N-9-fluorenylmethoxycarbonyl |
| HOBt: | 1-hydroxybenztriazole |
| HOOBt: | 3,4-dihydro-3-hydroxy-4-oxo-1,2,3-benzotriazine |
| HONB: | 1-hydroxy-5-norbornene-2,3-dicarboximide |
| DCC: | N,N'-dicyclohexylcarbodiimide |
| BSA: | Bovine serum albumin |
| CHAPS: | (3-[(3-Cholamidopropyl)dimethylammonio]-1-propanesulfonate |
| PAM: | Phenylacetamidemethyl |
| DIPCI: | N,N'-diisopropylcarbodiimide |

The sequence identification numbers in the sequence listing of the specification indicates the following sequence, respectively.

[SEQ ID NO: 1]

This shows the amino acid sequence of TGR23-1, the human-derived novel G protein-coupled receptor protein (sometimes referred to as human TGR23-1) of the present invention.

[SEQ ID NO: 2]

This shows the base sequence of cDNA encoding TGR23-1, the human-derived novel G protein-coupled receptor protein of the present invention.

[SEQ ID NO: 3]

This shows the amino acid sequence of TGR23-2, the human-derived novel G protein-coupled receptor protein (sometimes referred to as human TGR23-2) of the present invention.

[SEQ ID NO: 4]

This shows the base sequence of cDNA encoding TGR23-2, the human-derived novel G protein-coupled receptor protein of the present invention.

[SEQ ID NO: 5]

This shows the base sequence of primer 1 used in the PCR reaction of Example 1 described below.

[SEQ ID NO: 6]

This shows the base sequence of primer 2 used in the PCR reaction of Example 1 described below.

[SEQ ID NO: 7]

This shows the base sequence of primer 3 used in the PCR reaction of Example 2 described below.

[SEQ ID NO: 8]

This shows the base sequence of primer 4 used in the PCR reaction of Example 2 described below.

[SEQ ID NO: 9]

This shows the base sequence of probe 1 used in the PCR reaction of Example 2, Example 3 and Example 4 described below. [5'-terminus was labeled with FAM (6-carboxy-fluorescein) as a reporter dye, 3'-terminus with TAMRA (6-carboxy-tetramethyl-rhodamine) as a quencher.]

[SEQ ID NO: 10]

This shows the amino acid sequence of TGR23-A, the mouse-derived novel G protein-coupled receptor protein (sometimes referred to as mouse TGR23-A) of the present invention.

[SEQ ID NO: 11]

This shows the base sequence of cDNA encoding TGR23-A, the mouse-derived novel G protein-coupled receptor protein of the present invention.

[SEQ ID NO: 12]

This shows the base sequence of primer 5 used in the PCR reaction of Example 5 described below.

[SEQ ID NO: 13]

This shows the base sequence of primer 6 used in the PCR reaction of Example 5 described below.

[SEQ ID NO: 14]

This shows the amino acid sequence of TGR23-B, the mouse-derived novel G protein-coupled receptor protein (sometimes referred to as mouse TGR23-B) of the present invention.

[SEQ ID NO: 15]

This shows the base sequence of cDNA encoding TGR23-B, the mouse-derived novel G protein-coupled receptor protein of the present invention.

[SEQ ID NO: 16]

This shows the amino acid sequence of the human-derived novel G protein-coupled receptor protein.

[SEQ ID NO: 17]

This shows the base sequence encoding the amino acid sequence represented by SEQ ID NO: 16.

[SEQ ID NO: 18]

This shows the amino acid sequence of the human-derived novel G protein-coupled receptor protein.

[SEQ ID NO: 19]

This shows the base sequence encoding the amino acid sequence represented by SEQ ID NO: 18.

[SEQ ID NO: 20]

This shows the base sequence of primer 1 used in the PCR reaction of Reference Example 1 and Reference Example 15 described below.

[SEQ ID NO: 21]

This shows the base sequence of primer 2 used in the PCR reaction of Reference Example 1 and Reference Example 15 described below.

[SEQ ID NO: 22]

This shows the base sequence of primer used for measurement of the expression level of TGR23-2 gene in TGR23-2 expressing CHO cells in Reference Example 2 described below and TGR23-1 gene in TGR23-1 expressing CHO cells in Reference Example 16 described below.

[SEQ ID NO: 23]

This shows the base sequence of primer used for measurement of the expression level of TGR23-2 gene in TGR23-2 expressing CHO cells in Reference Example 2 described below and TGR23-1 gene in TGR23-1 expressing CHO cells in Reference Example 16 described below.

[SEQ ID NO: 24]

This shows the base sequence of probe used for measurement of the expression level of TGR23-2 gene in TGR23-2 expressing CHO cells in Reference Example 2 described below and TGR23-1 gene in TGR23-1 expressing CHO cells in Reference Example 16 described below.

[SEQ ID NO: 25]

This shows the amino acid sequence of rat TGR23-2 ligand (1-18).

[SEQ ID NO: 26]

This shows the amino acid sequence of rat TGR23-2 ligand (1-15).

[SEQ ID NO: 27]

This shows the amino acid sequence of rat TGR23-2 ligand (1-14).

[SEQ ID NO: 28]

This shows the base sequence of primer used in the PCR reaction of Reference Example 11 described below.

[SEQ ID NO: 29]

This shows the base sequence of primer used in the PCR reaction of Reference Example 11 described below.

[SEQ ID NO: 30]

This shows the base sequence of primer used in the PCR reaction of Reference Example 11 described below.

[SEQ ID NO: 31]

This shows the base sequence of cDNA encoding the human TGR23-2 ligand precursor.

[SEQ ID NO: 32]

This shows the amino acid sequence of the human TGR23-2 ligand precursor.

[SEQ ID NO: 33]

This shows the amino acid sequence of the human TGR23-2 ligand (1-18).

[SEQ ID NO: 34]

This shows the amino acid sequence of the human TGR23-2 ligand (1-15).

[SEQ ID NO: 35]

This shows the amino acid sequence of the human TGR23-2 ligand (1-14).

[SEQ ID NO: 36]

This shows the amino acid sequence of the human TGR23-2 ligand (1-20).

[SEQ ID NO: 37]

This shows the base sequence of primer used in the PCR reaction of Reference Example 12 described below.

[SEQ ID NO: 38]

This shows the base sequence of primer used in the PCR reaction of Reference Example 12 described below.

[SEQ ID NO: 39]

This shows the base sequence of primer used in the PCR reaction of Reference Example 12 described below.

[SEQ ID NO: 40]

This shows the base sequence of cDNA encoding the mouse TGR23-2 ligand precursor.

[SEQ ID NO: 41]

This shows the amino acid sequence of the mouse TGR23-2 ligand precursor.

[SEQ ID NO: 42]

This shows the amino acid sequence of the mouse TGR23-2 ligand (1-18).

[SEQ ID NO: 43]

This shows the amino acid sequence of the mouse TGR23-2 ligand (1-15).

[SEQ ID NO: 44]

This shows the amino acid sequence of the mouse TGR23-2 ligand (1-14).

[SEQ ID NO: 45]

This shows the amino acid sequence of the mouse TGR23-2 ligand (1-20).

[SEQ ID NO: 46]

This shows the base sequence of primer used in the PCR reaction of Reference Example 13 described below.

[SEQ ID NO: 47]

This shows the base sequence of cDNA encoding a part of the rat TGR23-2 ligand precursor.

[SEQ ID NO: 48]

This shows the amino acid sequence of a part of the rat TGR23-2 ligand precursor.

[SEQ ID NO: 49]

This shows the amino acid sequence of the rat TGR23-2 ligand (1-20).

[SEQ ID NO: 50]

This shows the base sequence encoding the amino acid sequence represented by SEQ ID NO: 25.

[SEQ ID NO: 51]

This shows the base sequence encoding the amino acid sequence represented by SEQ ID NO: 26.

[SEQ ID NO: 52]

This shows the base sequence encoding the amino acid sequence represented by SEQ ID NO: 27.

[SEQ ID NO: 53]

This shows the base sequence encoding the amino acid sequence represented by SEQ ID NO: 49.

[SEQ ID NO: 54]

This shows the base sequence encoding the amino acid sequence represented by SEQ ID NO: 33.

[SEQ ID NO: 55]

This shows the base sequence encoding the amino acid sequence represented by SEQ ID NO: 34.

[SEQ ID NO: 56]

This shows the base sequence encoding the amino acid sequence represented by SEQ ID NO: 35.

[SEQ ID NO: 57]

This shows the base sequence encoding the amino acid sequence represented by SEQ ID NO: 36.

[SEQ ID NO: 58]

This shows the base sequence encoding the amino acid sequence represented by SEQ ID NO: 42.

[SEQ ID NO: 59]

This shows the base sequence encoding the amino acid sequence represented by SEQ ID NO: 43.

[SEQ ID NO: 60]

This shows the base sequence encoding the amino acid sequence represented by SEQ ID NO: 44.

[SEQ ID NO: 61]

This shows the base sequence encoding the amino acid sequence represented by SEQ ID NO: 45.

[SEQ ID NO: 62]

This shows the amino acid sequence of the human TGR23-2 ligand (1-16).

[SEQ ID NO: 63]

This shows the base sequence encoding the amino acid sequence represented by SEQ ID NO: 62.

[SEQ ID NO: 64]

This shows the amino acid sequence of TGR23, the rat-derived novel G protein-coupled receptor protein of the present invention.

[SEQ ID NO: 65]

This shows the base sequence of cDNA encoding TGR23, the rat-derived novel G protein-coupled receptor protein of the present invention.

[SEQ ID NO: 66]

This shows the base sequence of primer 7 used in the PCR reaction of Example 6 described below.

[SEQ ID NO: 67]

This shows the base sequence of primer 8 used in the PCR reaction of Example 6 described below.

[SEQ ID NO: 68]

This shows the base sequence of primer used in the PCR reaction of Reference Example 14 described below.

[SEQ ID NO: 69]

This shows the base sequence of primer used in the PCR reaction of Reference Example 14 described below.

[SEQ ID NO: 70]

This shows the base sequence of primer used in the PCR reaction of Reference Example 14 described below.

[SEQ ID NO: 71]

This shows the base sequence of cDNA encoding the rat TGR23-2 ligand precursor.

[SEQ ID NO: 72]

This shows the amino acid sequence of the rat TGR23-2 ligand precursor.

The transformant *Escherichia coli* TOP10/pTB2173 obtained in Example 1 described below was on deposit with Institute for Fermentation (IFO), located at 2-17-85 Juso-honmachi, Yodogawa-ku, Osaka-shi, Osaka, Japan, as the Accession Number IFO 16483 on Oct. 24, 2000, and with International Patent Organisms Depository, National Institute of Advanced Industrial Science and Technology (formerly, National Institute of Bioscience and Human-Technology (NIBH), Ministry of International Trade and Industry), located at Central 6, 1-1-1 Higashi, Tsukuba, Ibaraki, 305-8566, Japan, as the Accession Number FERM BP-7346 on Nov. 1, 2000.

The transformant *Escherichia coli* TOP10/pTB2174 obtained in Example 1 described below was on deposit with Institute for Fermentation (IFO), located at 2-17-85 Juso-honmachi, Yodogawa-ku, Osaka-shi, Osaka, Japan, as the Accession Number IFO 16484 on Oct. 24, 2000, and with International Patent Organisms Depository, National Institute of Advanced Industrial Science and Technology (formerly, National Institute of Bioscience and Human-Technology (NIBH), Ministry of International Trade and Industry), located at Central 6, 1-1-1 Higashi, Tsukuba, Ibaraki, 305-8566, Japan, as the Accession Number FERM BP-7347 on Nov. 1, 2000.

The transformant *Escherichia coli* TOP10/pTB2237 obtained in Example 5 described below was on deposit with Institute for Fermentation (IFO), located at 2-17-85 Juso-honmachi, Yodogawa-ku, Osaka-shi, Osaka, Japan, as the Accession Number IFO 16705 on Sep. 13, 2001, and with International Patent Organisms Depository, National Institute of Advanced Industrial Science and Technology, located at Central 6, 1-1-1 Higashi, Tsukuba, Ibaraki, 305-8566, Japan, as the Accession Number FERM BP-7754 on Sep. 25, 2001.

EXAMPLES

The present invention is described in detail below with reference to EXAMPLES, but is not deemed to limit the scope of the present invention thereto. The gene manipulation procedures using *Escherichia coli* were performed according to the methods described in the Molecular Cloning.

Example 1

Cloning of the cDNA Encoding the Novel Human Colon Cancer-Derived G Protein-Coupled Receptor Protein and Determination of the Base Sequence Using human colon cancer-derived (CX-1) cDNA (CLONTECH) as a template and two primers, namely, primer 1 (SEQ ID NO: 5) and primer 2 (SEQ ID NO: 6), PCR was carried out. The reaction solution in the above reaction comprised of 5 μl of the cDNA as a template, 2.5 U of Pfu Turbo DNA Polymerase (STRATAGENE), 1.0 μM each of primer 1 (SEQ ID NO: 5) and primer 2 (SEQ ID NO: 6), 200 μM of dNTPs, and 25 μl of 2×GC Buffer I (Takara) attached to the enzyme to make the total volume 50 μl. The PCR reaction was carried out by reaction of 95° C. for 1 minute, then a cycle set to include 95° C. for 1 minute followed by 60° C. for 1 minute and 72° C. for 1.5 minutes, which was repeated 38 times, and finally, extension reaction at 72° C. for 10 minutes. The PCR product was subcloned into plasmid vector pCR-BluntII-TOPO (Invitrogen) following the instructions attached to the Zero Blunt TOPO PCR Cloning Kit (Invitrogen). The plasmid was then introduced into *Escherichia coli* TOP10, and the clones containing the cDNA were selected on LB agar plates containing kanamycin. As a result of analysis for sequence of each clone, the base sequences of cDNA encoding the novel G protein-coupled receptor protein were obtained (SEQ ID NO: 2 and SEQ ID NO: 4). The plasmid having a DNA fragment having the base sequence represented by SEQ ID NO: 2 and the plasmid having a DNA fragment having the base sequence represented by SEQ ID NO: 4 were designated pTB2173 and pTB2174, respectively. The novel G protein-coupled receptor proteins containing the amino acid sequences (SEQ ID NO: 1 and SEQ ID NO: 3) encoded by the base sequences of these DNA (SEQ ID NO: 2 and SEQ ID NO: 4) were designated TGR23-1 and TGR23-2, respectively. In addition, the transformants, to which the plasmids pTB2173 and pTB2174 were introduced, were designated *Escherichia coli* TOP10/pTB2173 and *Escherichia coli* TOP10/pTB2174, respectively.

In the amino acid sequence of TGR23-2, Asn, which is located at the $107^{th}$ amino acid in the amino acid sequence of TGR23-1, is substituted to lie, and Gin at the $344^{th}$ amino acid is substituted to Arg. In addition, in the base sequence of DNA encoding TGR23-2, A, which is located at the $320^{th}$ base in the base sequence of DNA encoding TGR23-1, is substituted to T, C at the $648^{th}$ base is substituted to T, A at the $1031^{st}$ base is substituted to G, and T at the $1071^{st}$ base is substituted to C.

Figure 2:
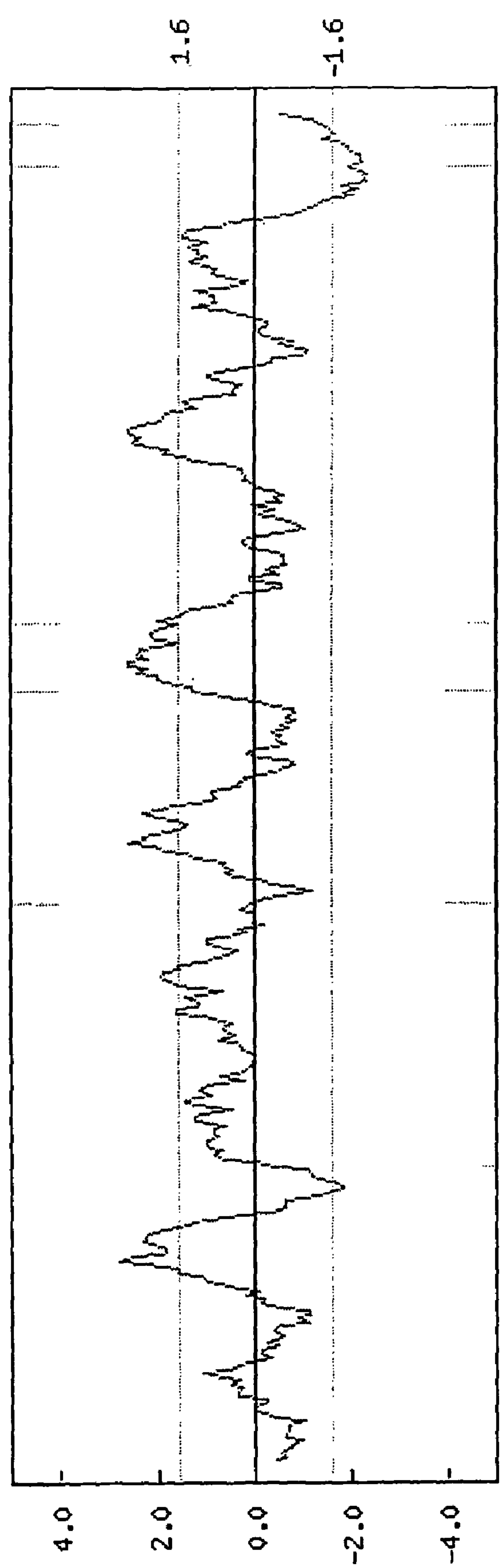
FIG. 2 shows a hydrophobicity plot of TGR23-2.

The hydrophobicity plots of TGR23-1 and TGR23-2 are indicated in FIG. 1 and FIG. 2, respectively.

Example 2

Analysis of the Tissues, in which Human TGR23-1 and TGR23-2 were Expressed

Using human MTC panel Human I, Human II and Human Tumor (CLONTECH) as a template and two primers, namely, primer 3 (SEQ ID NO: 7) and primer 4 (SEQ ID NO: 8), and probe 1 (SEQ ID NO: 9 (FAM-acctggtttg acctggtttg ccgagtggtc cgctqattt-TAMRA)), PCR was carried out. The reaction solution in the above reaction comprised of 1 μl of the cDNA described above as a template, 0.5 μM each of primer 3 (SEQ ID NO: 7) and primer 4 (SEQ ID NO: 8), 0.1 μM of probe 1 (SEQ ID NO: 9), and 25 μl of TaqMan Universal PCR Master Mix (Applied Biosystems) to make the total volume 50 μl. The PCR reaction was carried out by reaction of 50° C. for 2 minutes and 95° C. for 10 minutes, then a cycle set to include 95° C. for 15 seconds followed by 60° C. for 1 minute, which was repeated 40 times with ABI7700 (Applied Biosystems). After concentration of the plasmid pTB2174 was calculated by measuring absorbance at 260 nm and accurate copy numbers were calculated, 1 to $1\times10^6$ copies of standard cDNA solution were prepared by diluting with 10 mM Tris-HCl (pH8.0) containing 1 mM EDTA. The expression level was calculated by ABI PRISM 7700 SDS Software. Cycle numbers at the moment when fluorescent intensity of reporter comes to preset values indicated as a vertical axis, and logarithm of an initial concentration of the standard cDNA as a horizontal axis. Subsequently, a standard curve was prepared to estimate an expression level in 1 μl of MTC panel. As a result, it was confirmed that in 1 μl of MTC panel, 2.1 copies in heart cDNA, 13 copies in brain cDNA, 3.3 copies in placenta cDNA, 4.9 copies in lung cDNA, 5.6 copies in liver cDNA, 0.91 copies in skeletal muscle cDNA, 1.0 copy in kidney cDNA, 1.7 copies in pancreas cDNA, 2.3 copies in spleen cDNA, 2.6 copies in thymus cDNA, 0.9 copies in prostate cDNA, 1.8 copies in testis cDNA, 4.0 copies in ovary cDNA, 1.3 copies in small intestine cDNA, 5.5 copies in large intestine cDNA, 1.5 copies in leukocyte cDNA, 0.55 copies in breast cancer cell line (GI-101) cDNA, 730 copies in colon cancer cell line (CX-1) cDNA, 1.8 copies in colon cancer cell line (GI-112) cDNA, 64 copies in lung cancer cell line (LX-1) cDNA, 0.95 copies in lung cancer cell line (GI-117) cDNA, 2.1 copies in ovarian cancer cell line (GI-102) cDNA, and 2.4 copies in prostate cancer cell line (PC3) cDNA have been expressed. The above-mentioned values are a mean value that is obtained from two experiments in the same manner.

From these results, it is found that the extremely high expression of human TGR23-1 and TGR23-2 was observed in colon cancer cell line (CX-1) and lung cancer cell line (LX-1).

Figure 5:
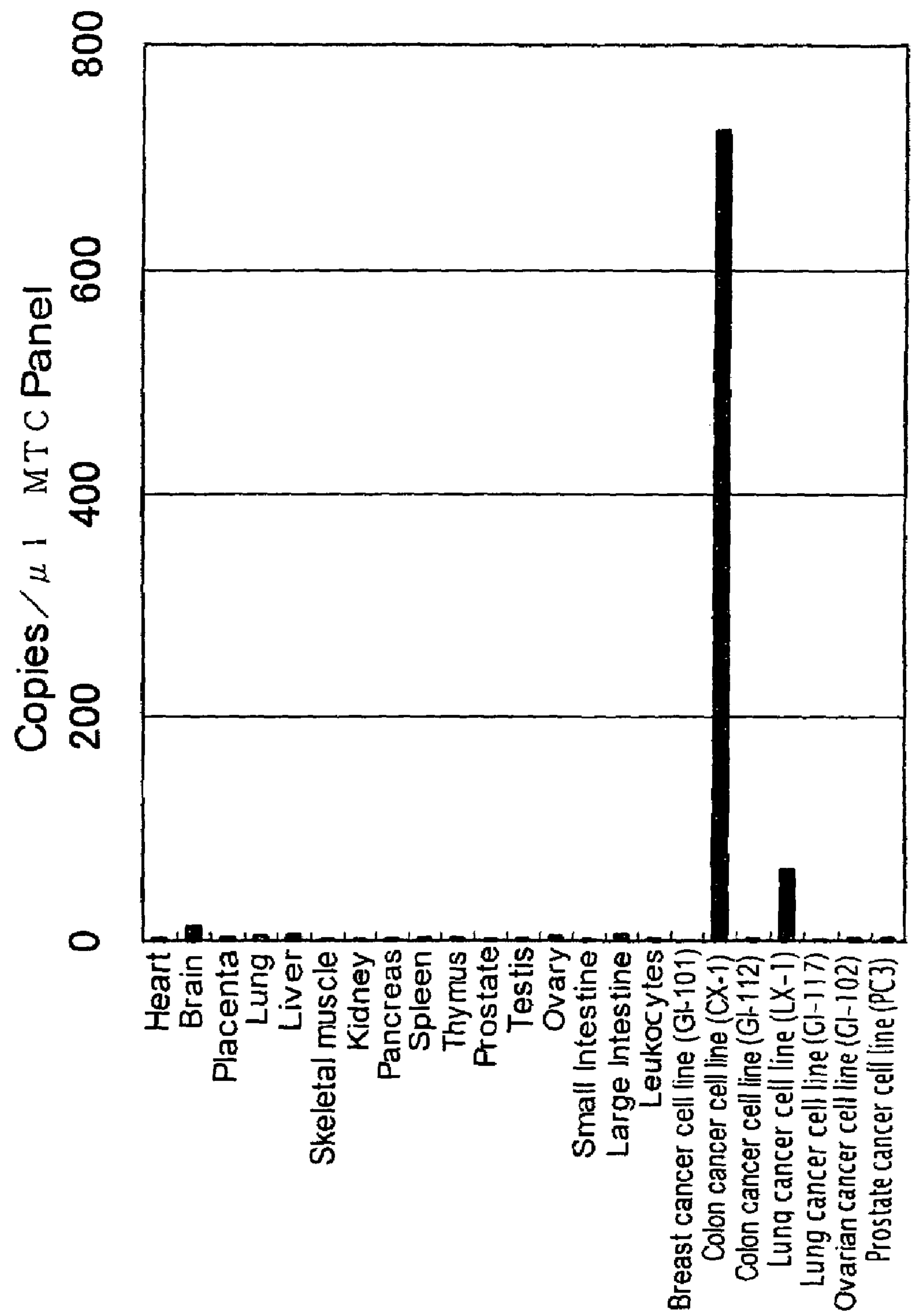
FIG. 5 shows a graph of expression level of human TGR23-1 and TGR23-2 in MTC panel.

The graph of expression level of MTC Panel for human TGR23-1 and TGR23-2 is indicated in FIG. 5.

Example 3

Analysis of Expression of Human TGR23-1 and Human TGR23-2 in both Normal Tissues and Cancer Tissues Using human Matched pair cDNA (CLONTECH) as a template and two primers, namely, primer 3 (SEQ ID NO: 7) and primer 4 (SEQ ID NO: 8), and probe 1 (SEQ ID NO: 9), PCR was carried out. The reaction solution in the above reaction comprised of 1 μl of the cDNA described above as a template, 0.5 μM each of primer 3 (SEQ ID NO: 7) and primer 4 (SEQ ID NO: 8), 0.1 μM of probe 1 (SEQ ID NO: 9), and 25 μl of TaqMan Universal PCR Master Mix (Applied Biosystems) to make the total volume 50 μl. The PCR reaction was carried out by reaction of 50° C. for 2 minutes and 95° C. for 10 minutes, then a cycle set to include 95° C. for 15 seconds followed by 60° C. for 1 minute, which was repeated 40 times with ABI7700 (Applied Biosystems). As a result of the same analysis as that of EXAMPLE 2, it was confirmed that in 1 μl of Matched pair cDNA, 0.0 copy in normal tissue of Breast 1, 0.0 copy in cancer tissue of Breast 1, 0.0 copy in normal tissue of Breast 2, 0.78 copies in cancer tissue of Breast 2, 0.0 copies in normal tissue of Breast 3, 0.0 copies in cancer tissue of Breast 3, 0.0 copy in normal tissue of Breast 4, 0.0 copy in cancer tissue of Breast 4, 2.4 copies in normal tissue of Lung 4, 0.77 copies in cancer tissue of Lung 4, 2.8 copies in normal tissue of Lung 5, 0.31 copies in cancer tissue of Lung 5, 0.0 copy in normal tissue of Lung 6, 2.0 copies in cancer tissue of Lung 6, 0.69 copies in normal tissue of Colon 1, 52 copies in cancer tissue of Colon 1, 1.5 copies in normal tissue of Colon 2, 150 copies in cancer tissue of Colon 2, 3.5 copies in normal tissue of Colon 3, 0.0 copy in cancer tissue of Colon 3, 5.1 copies in normal tissue of Colon 4, 21 copies in cancer tissue of Colon 4, 34 copies in normal tissue of Colon 5, 890 copies in cancer tissue of Colon 5, 1.9 copies in normal tissue of Colon 6, 14 copies in cancer tissue of Colon 6, 7.7 copies in normal tissue of Colon 7, 3.2 copies in cancer tissue of Colon 7, 0.77 copies in normal tissue of Rectum 1, 12 copies in cancer tissue of Rectum 1, 1.7 copies in normal tissue of Rectum 2, 0 copy in cancer tissue of Rectum 2, 10 copies in normal tissue of Rectum 3, 6.2 copies in cancer tissue of Rectum 3, 13 copies in normal tissue of Ovary 1, 1.5 copies in cancer tissue of Ovary 1, 24 copies in normal tissue of Ovary 2, 0.0 copy in cancer tissue of Ovary 2, 0.77 copies in normal tissue of Ovary 3, 0.0 copy in cancer tissue of Ovary 3, 1.9 copies in normal tissue of Ovary 4, 1.6 copies in cancer tissue of Ovary 4, 0.81 copies in normal tissue of Ovary 5, 0.0 copy in cancer tissue of Ovary 5, 0.0 copy in normal tissue of Prostate 1, 0.0 copy in cancer tissue of Prostate 1, 1.35 copies in normal tissue of Prostate 3, and 0.0 copy in cancer tissue of Prostate 3 have been expressed.

From this result, it is found that the expression of human TGR23-1 and human TGR23-2 have been increased in cDNA of colon cancer tissues at high frequency, which is 3 of 7 examples (Colon 1, Colon 3 and Colon 5), in comparison with that of normal tissues.

Figure 6:
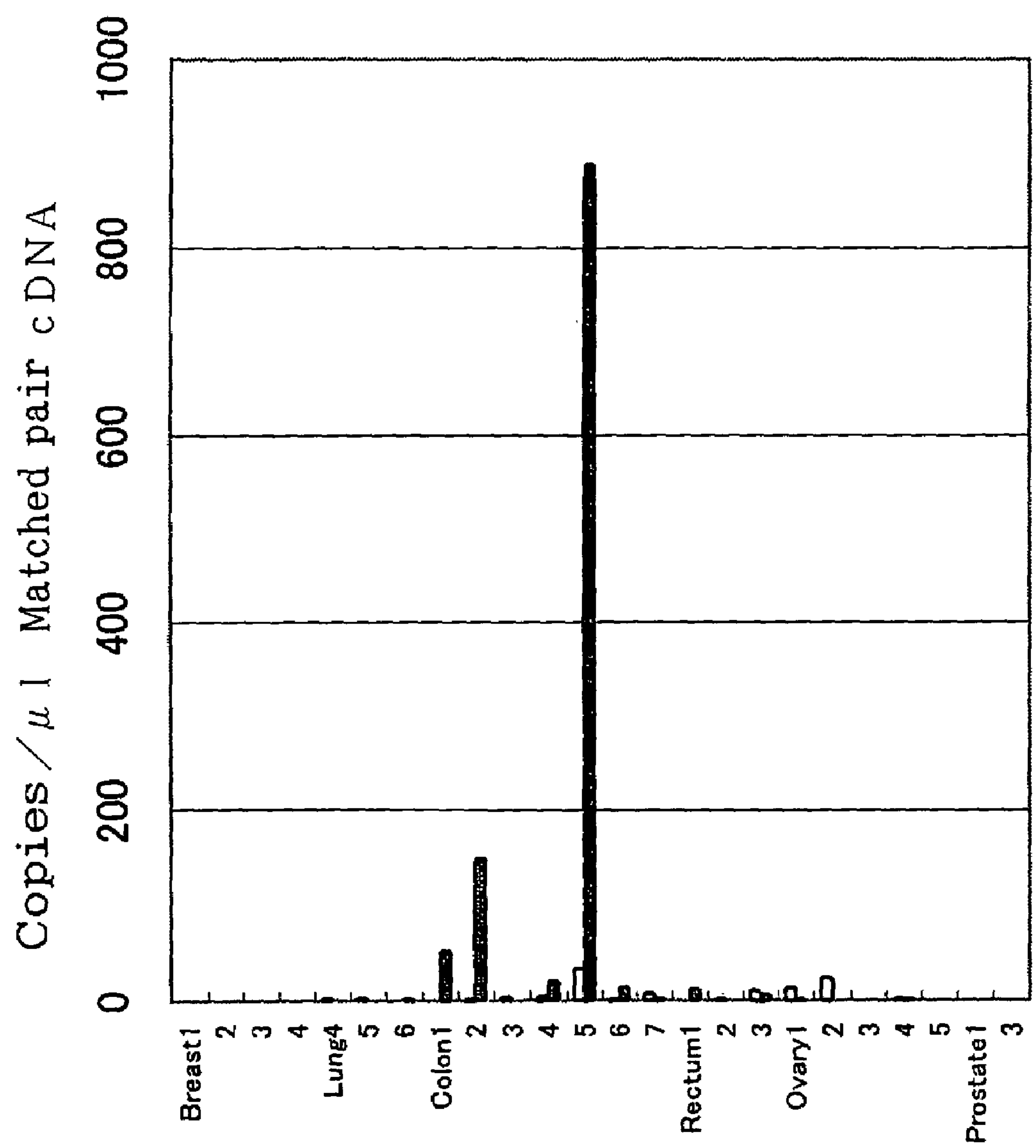
FIG. 6 shows a graph of expression level of human TGR23-1 and TGR23-2 in Matched pair cDNA. White bars represent a result of normal tissues, and black bars represent a result of cancer tissues.

The graph indicating the expression level of human TGR23-1 and human TGR23-2 in Matched pair cDNA is shown in FIG. 6.

Example 4

Analysis of Expression of Human TGR23-1 and Human TGR23-2 in Cancer Cell Lines The expression level of human TGR23-1 and TGR23-2 was investigated using cancer cell lines SW620 (human colon cancer derived), LS123 (human colon cancer derived), COL0205 (human colon cancer derived), DU145 (human prostate cancer derived), ZR75-1 (human breast cancer derived), NCI-H358 (human bronchovesicular adenocarcinoma derived), wherein each cell line was available from ATCC. SW620 was cultivated with Leibovitz's L15 medium (SIGMA, Cat No. L5520), LS123 with EMEM medium (GIBCO, Cat No. 11090-081), COL0205, ZR75-1 and NCI-H358 with RPMI 1640 medium containing 10 mM HEPES (GIBCO) and 1 mM Sodium Pyruvate (GIBCO), DU145 with EMEM medium (GIBCO, Cat No. 11095-080) containing 1 mM MEM non-essential amino acid solution and 1 mM Sodium Pyruvate (GIBCO), wherein each medium was supplemented with 10% fetal bovine serum (GIBCO) and 0.1 g/L of kanamycin (GIBCO). Cell culture was performed in 10 cm dish. RNA was prepared using Rneasy Mini Kit (Qiagen). Concentration of RNA obtained was calculated by measurement of absorbance at 260 nm. Reverse transcription was performed using 5 ng of each RNA with TaqMan Reverse Transcription Reagents (Applied Biosystems). Using a given amount of the obtained reverse transcripts equivalent to 1 ng or 1 ng of RNA, to which the reverse transcription was not done, as a template, two primers, namely primer 3 (SEQ ID NO: 7) and primer 4 (SEQ ID NO: 8), and probe 1 (SEQ ID NO: 9), PCR reaction was performed. The reaction solution in the above reaction comprised of a given amount of the obtained reverse transcripts equivalent to 1 ng or 1 ng of RNA as a template, 0.5 μM each of primer 3 (SEQ ID NO: 7) and primer 4 (SEQ ID NO: 8), 0.1 μM of probe 1 (SEQ ID NO: 9), and 12.5 μl of TaqMan Universal PCR Master Mix (Applied Biosystems) to make the total volume 25 μl. The PCR reaction was carried out by reaction of 50° C. for 2 minutes and 95° C. for 10 minutes, then a cycle set to include 95° C. for 15 seconds followed by 60° C. for 1 minute, which was repeated 40 times with ABI7700 (Applied Biosystems). Similarly, using a given amount of the obtained reverse transcripts equivalent to 0.25 ng or 0.25 ng of RNA, to which the reverse transcription was not done, as a template, and TaqMan β-actin Control Reagents (Applied Biosystems), PCR reaction was performed. The reaction solution in the above reaction comprised of a given amount of the obtained reverse transcripts equivalent to 0.25 ng or 0.25 ng of RNA, to which the reverse transcription was not done, as a template, 0.4 μM each of β-actin Forward Primer and β-actin Reverse Primer, 0.5 μM of β-actin Probe, and 12.5 μl of TaqMan Universal PCR Master Mix (Applied Biosystems) to make the total volume 25 μl. The PCR reaction was carried out by reaction of 50° C. for 2 minutes and 95° C. for 10 minutes, then a cycle set to include 95° C. for 15 seconds followed by 62° C. for 1 minute, which was repeated 40 times with ABI7700 (Applied Biosystems). Analysis was performed in the same manner as EXAMPLE 2, and the expression level was determined by subtracting the value obtained from the reaction without reverse transcription from the value obtained from analysis of the reverse transcripts. In addition, the expression level of human TGR23-1 and TGR23-2 was calculated as a value against that of β-actin. Where the value showed less than zero, the value was replaced with zero. The expression level of human TGR23-1 and TGR23-2 against β-actin was 0.0021% in SW620, 0.0% in LS123, 2.1% in COL0205, 0.0029% in DU145, 0.0012% in ZR75-1 and 0.0% in NCI-H358.

From this result, it is found that the expression of human TGR23-1 and human TGR23-2 was greatly enhanced in COL0205.

Figure 7:
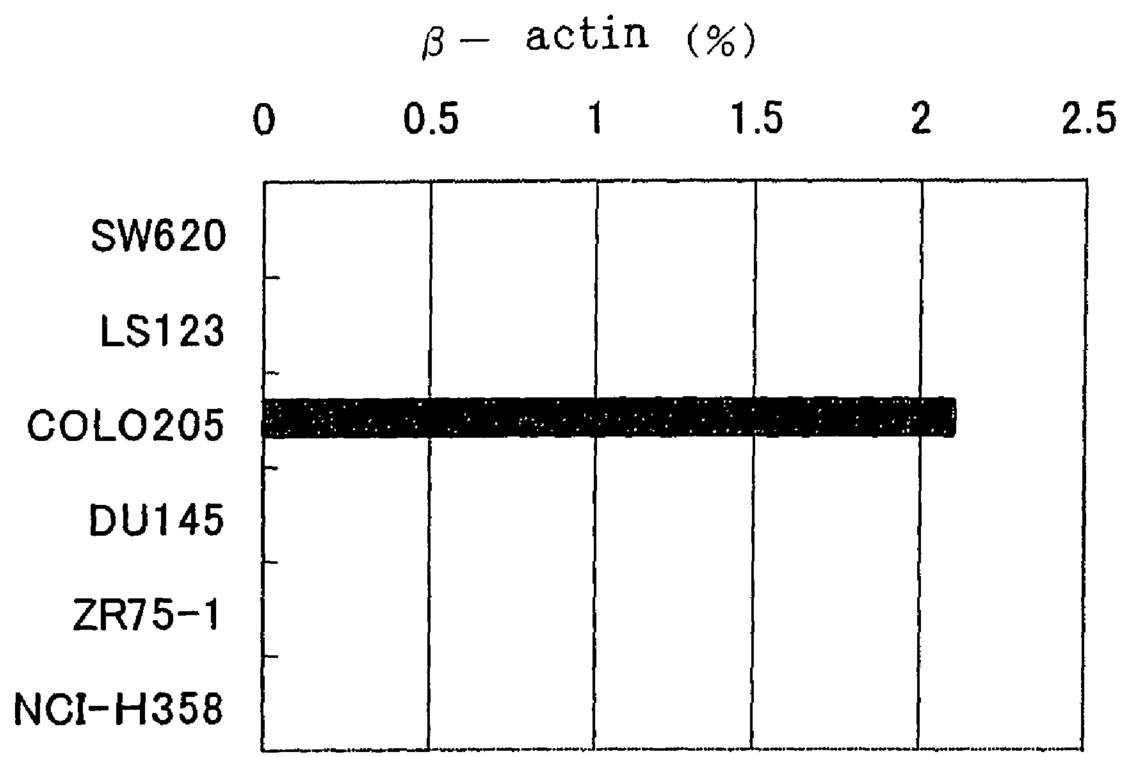
FIG. 7 shows a graph of expression level of human TGR23-1 and TGR23-2 in cancer cells.

The graph indicating the expression level of human TGR23-1 and human TGR23-2 in cancer cell lines is shown in FIG. 7.

Example 5

Cloning of the cDNA Encoding the Mouse Brain-Derived G Protein-Coupled Receptor Protein and Determination of the Base Sequence Using mouse Marathon Ready cDNA (CLONTECH) as a template and two primers, namely, primer 5 (SEQ ID NO: 12) and primer 6 (SEQ ID NO: 13), PCR was carried out. The reaction solution in the above reaction comprised of 1 μl of the above cDNA as a template, 2.5 U of Pfu Turbo DNA Polymerase (STRATAGENE), 1.0 μM each of primer 5 (SEQ ID NO: 12) and primer 6 (SEQ ID NO: 13), 200 μM of dNTPs, and 25 μl of 2×GC Buffer I (Takara) attached to the enzyme to make the total volume 50 μl. The PCR reaction was carried out by reaction of 95° C. for 1 minute, then a cycle set to include 95° C. for 1 minute followed by 60° C. for 1 minute and 72° C. for 1.5 minutes, which was repeated 38 times, and finally, extension reaction at 72° C. for 10 minutes. Subsequently, agarose gel electrophoresis was done, and the PCR product was purified using Gel Extraction Kit (QIAGEN). This purified product was subcloned to plasmid vector pCR-Blunt II-TOPO (Invitrogen) according to the instructions attached with the Zero Blunt TOPO PCR Cloning Kit (Invitrogen). This plasmid was introduced into *Escherichia coli* TOP10, and the clones harboring the cDNA were selected on LB agar medium containing kanamycin. A sequence of each clone was analyzed, and the base sequence (SEQ ID NO: 11) of cDNA encoding a novel G protein-coupled receptor protein was obtained. The novel G protein-coupled receptor protein containing the amino acid sequence (SEQ ID NO: 10), which is encoded by the base sequence (SEQ ID NO: 11) of the DNA, was designated mouse TGR23-A.

The plasmid harboring the DNA fragment having the base sequence represented by SEQ ID NO: 11 was designated pTB2237, and the transformant trandformed with plasmid pTB2237 was designated *Escherichia coli* TOP10/pTB2237.

Figure 8:
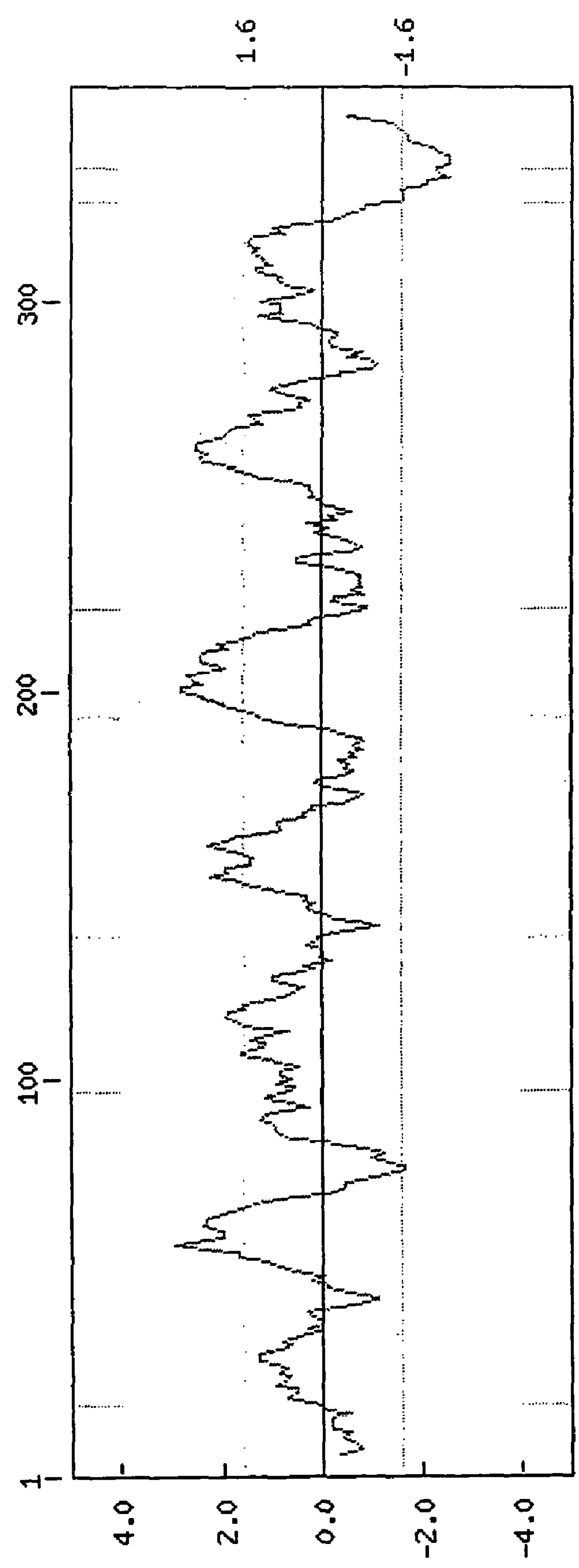
FIG. 8 shows a hydrophobicity plot of mouse TGR23-A.
Figure 10:
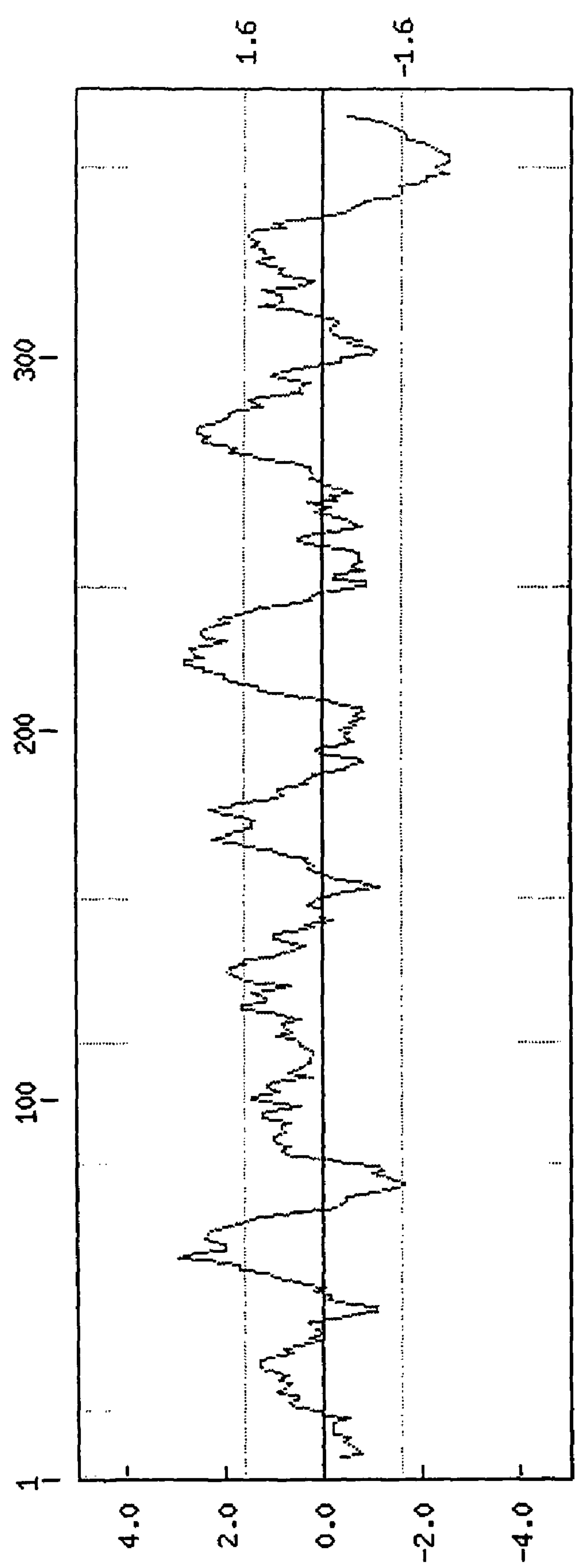
FIG. 10 shows a hydrophobicity plot of mouse TGR23-B.

The hydrophobicity plot of mouse TGR23-A is shown in FIG. 8.

Example 6

Cloning of the cDNA Encoding the Rat Brain-Derived G Protein-Coupled Receptor Protein and Determination of the Base Sequence Using rat Marathon Ready cDNA (CLONTECH) as a template and two primers, namely, primer 7 (SEQ ID NO: 66) and primer 8 (SEQ ID NO: 67), PCR was carried out. The reaction solution in the above reaction comprised of 2.5 μl of the above cDNA as a template, 1 μl of Advantage 2 Polymerase Mix (CLONTECH), 0.2 μM each of primer 7 (SEQ ID NO: 66) and primer 8 (SEQ ID NO: 67), 800 μM of dNTPs, and 2 μl of DMSO to make the total volume 50 μl. The PCR reaction was carried out by reaction of 95° C. for 1 minute, then a cycle set to include 95° C. for 30 seconds followed by 72° C. for 4 minutes, which was repeated 5 times, 95° C. for 30 seconds followed by 70° C. for 4 minutes, which was repeated 5 times, 95° C. for 30 seconds followed by 68° C. for 4 minutes, which was repeated 30 times, and finally, extension reaction at 68° C. for 3 minutes. Subsequently, agarose gel electrophoresis was done, and the PCR product was purified using GENECLEAN SPIN Kit (BIO101). This purified product was subcloned to plasmid vector pCR2.1-TOPO (Invitrogen) according to the instructions attached with the TOPO TA Cloning Kit (Invitrogen). This plasmid was introduced into *Escherichia coli* DH5α, and the clones harboring the cDNA were selected on LB agar medium containing ampicillin. A sequence of each clone was analyzed, and the base sequence (SEQ ID NO: 65) of cDNA encoding a novel G protein-coupled receptor protein was obtained. The novel G protein-coupled receptor protein containing the amino acid sequence (SEQ ID NO: 64), which is encoded by the base sequence (SEQ ID NO: 65) of the DNA, was designated rat TGR23.

The plasmid harboring the DNA fragment having the base sequence represented by SEQ ID NO: 65 was designated pCR2.1-rTGR23, and the transformant trandformed with plasmid pCR2.1-rTGR23 was designated *Escherichia coli* DH5α/pCR2.1-rTGR23.

Figure 12:
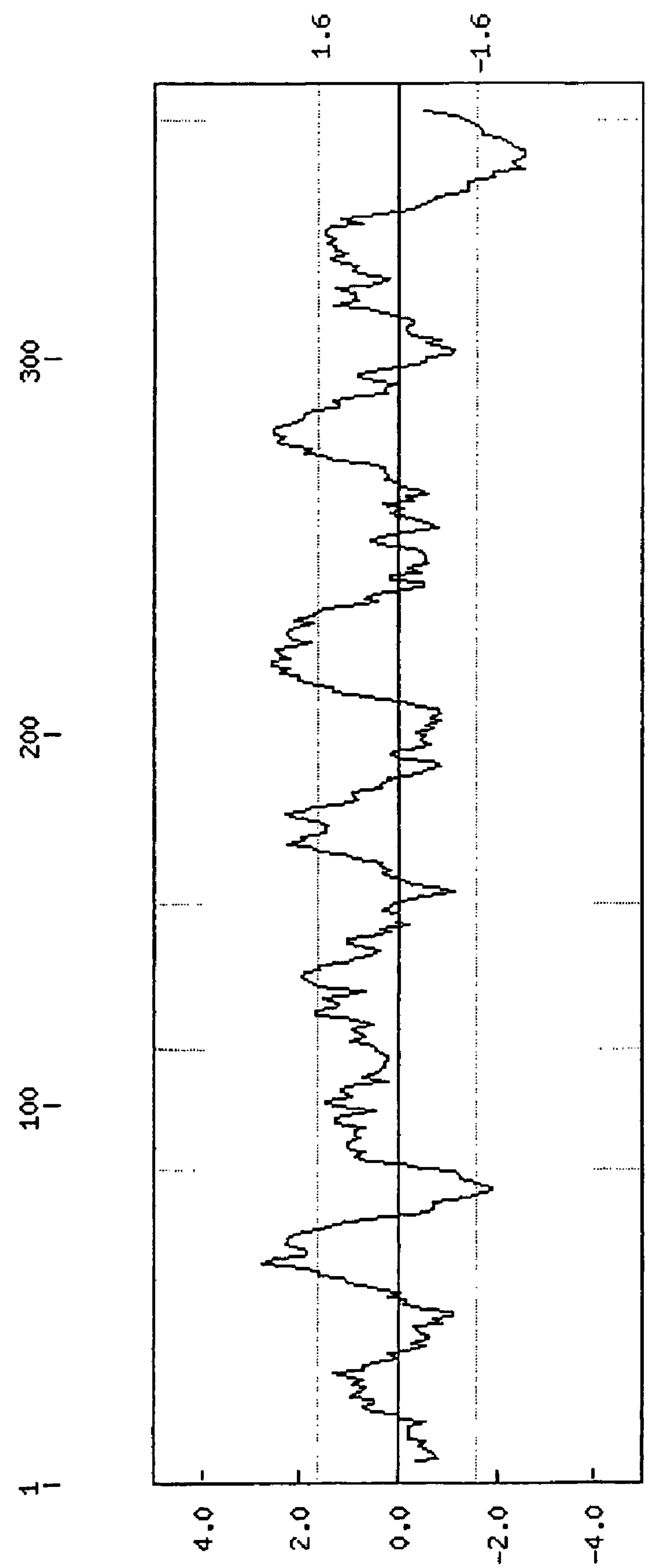
FIG. 12 shows a hydrophobicity plot of rat TGR23.

The hydrophobicity plot of rat TGR23 is shown in FIG. 12.

Reference Example 1

Preparation of TGR23-2 (Hereinafter, Sometimes Human TGR23-2 is Merely Referred to as TGR23-2) Expressing CHO Cells Using the plasmid pTB2174 obtained in EXAMPLE 1 as a template and two primers, namely, primer 1 attached to Sal I recognition sequence (SEQ ID NO: 20) and primer 2 attached to Spe I recognition sequence (SEQ ID NO: 21), PCR was carried out. The reaction solution in the above reaction comprised of 10 ng of the plasmid as a template, 2.5

U of Pfu Turbo DNA Polymerase (STRATAGENE), 1.0 μM each of primer 1 (SEQ ID NO: 20) and primer 2 (SEQ ID NO: 21), 200 μM of dNTPs, and 25 μl of 2×GC Buffer I (Takara) to make the total volume 50 μl. The PCR reaction was carried out by reaction of 95° C. for 1 minute, then a cycle set to include 95° C. for 60 seconds followed by 95° C. for 60 seconds, 55° C. for 60 seconds and 72° C. for 70 seconds, which was repeated 25 times, and finally, extension reaction at 72° C. for 10 minutes. The PCR product was subcloned into plasmid vector pCR-Blunt II-TOPO (Invitrogen) following the instructions attached to the Zero Blunt TOPO PCR Cloning Kit (Invitrogen). The plasmid was then introduced into *Escherichia coli* TOP10 (Invitrogen), and the clones having the cDNA of TGR23-2, which is contained in pTB2174, were selected on LB agar plates containing kanamycin. From *E. coli* clones transformed by the plasmid thus obtained, in which the TGR23-2 was introduced, the plasmid was prepared using Plasmid Miniprep Kit (BIO RAD) and digested with the restriction enzymes Sal I and Spe I to excise the insert, wherein TGR23-2 was attached to Sal I recognition sequence at 5' end and Spe I recognition sequence at 3' end. The insert DNA was electrophoresed to excise from agarose gel and recovered using the Gel Extraction Kit (Qiagen). This insert DNA was added to the expression vector plasmid for animal cells, pAKKO-111H (the same vector plasmid as pAKKO1.11H described in Biochim. Biophys. Acta, Vol. 1219, pp. 251-259 (1994) by Hinuma, S. et al.), which has been cleaved with Sal I and Spe I, and both DNAs were ligated by the DNA Ligation Kit Ver. 2 (Takara Shuzo). Thus, the plasmid pAKKO-TGR23-2 for protein expression was constructed. After cultivating *E. coli* TOP10 transformed with this pAKKO-TGR23-2, plasmid DNA of pAKKO-TGR23-2 was prepared using Plasmid Miniprep Kit (BIO RAD). $1\times10^5$ cells of hamster CHO/dhfr$^-$ cell were seeded in Falcon dish (3.5 cm diameter) with α-MEM medium (with ribonucleosides and deoxyribonucleosides, GIBCO, Cat No. 12571) containing 10% Fetal Bovine Serum, and cultivated at 37° C. for overnight in 5% $CO_2$ incubater. Two μg of the above-mentioned expression plasmid, pAKKO-TGR23-2 was transfected using Transfection Reagent FuGENE 6 (Roche) in accordance with the procedures described in the attached instruction. After 18 hours of cultivation, the medium was exchanged to a fresh medium for growth. Further cultivation for 10 hours, the transfected cells were harvested by treatment with Trypsin-EDTA, and seeded to 10 of 96-well flat bottomed plates with a selection medium (α-MEM medium (without ribonucleosides and deoxyribonucleosides, GIBCO, Cat No. 0.12561) containing 10% dialyzed Fetal Bovine Serum). Cultivation was continued while the selection medium was exchanged every 3 or 4 days, and 79 clones of DHFR$^+$ cell, which grew as a colony, were acquired after 2 or 3 weeks.

Reference Example 2

Quantification of TGR23-2 Expression Level in TGR23-2 Expressing CHO Cell Lines Using TaqMan PCR Method The 79 clones of TGR23-2 expressing CHO cells obtained in REFERENCE EXAMPLE 1 were cultured in the 96-well plate, and total RNA was prepared using RNeasy 96 Kit (Qiagen). Using 50 to 200 ng of total RNA obtained and TaqMan Gold RT-PCR Kit (PE Biosystems), a reverse transcription reaction was performed. Using 25 μl of the reaction mixture containing a reverse transcript corresponding to 5 to 20 ng of the total RNA obtained or a standard cDNA prepared as described below, 1× Universal PCR Master Mix (PE Biosystems), 500 nM each of primers represented by SEQ ID NO: 22 and SEQ ID NO: 23, and 100 nM TaqMan probe represented by SEQ ID NO: 24 (Fam-acctggtttg ccgagtggtc cgctattt-Tamra; in the sequence, Fam and Tamra represent 6-carboxy-fluorescein and 6-carboxy-tetramethyl-rhodamine, respectively), PCR was performed with ABI PRISM 7700 Sequence Detector (PE Biosystems). The PCR was carried out by reaction of 50° C. for 2 minutes and 95° C. for 10 minute, then a cycle set to include 95° C. for 15 seconds followed by 60° C. for 60 seconds, which was repeated 40 times.

After concentration of the plasmid pTB2174 obtained in EXAMPLE 1 was calculated by measuring absorbance at 260 nm and accurate copy numbers were calculated, 2 to $2\times10^6$ copies of standard cDNA solution were prepared by diluting with 10 mM Tris-HCl (pH8.0) containing 1 mM EDTA. In addition, probe and primers for TaqMan PCR were designed by Primer Express Version 1.0 (PE Biosystems).

The expression level was calculated by ABI PRISM 7700 SDS Software. Cycle numbers at the moment when fluorescent intensity of reporter comes to preset values indicated as a vertical axis, and logarithm of an initial concentration of the standard cDNA as a horizontal axis. From this standard curve, the expression level of TGR23-2 gene per total RNA of each clone was found by calculating an initial concentration of each reverse transcript. As a result, 21 clones of CHO cell lines, in which the expression of TGR23-2 was high, were selected and cultured in 24-well plate. For these cells, the expression level of TGR23-2 was re-examined. After preparation of total RNA with Rneasy Mini Kits (Qiagen), the RNA was treated with DNase by RNase-free DNase Set (Qiagen). From total RNA obtained, the reverse transcription reaction was carried out in the same manner as described above, and the expression level of TGR23-2 gene per total RNA of each clone was found by the TaqMan PCR method. From this, it was revealed that the clones No. 53 and No. 58 of CHO cell lines expressing TGR23-2 were highly expressed.

In REFERENCE EXAMPLES described below, these two clones of the TGR23-2 expressing cells were used.

Reference Example 3

Assay for Promoting/Inhibiting Activities of Intracellular cAMP Production Using TGR23-2 Expressing CHO Cells The CHO/TGR23-2 cells prepared in REFERENCE EXAMPLE 1 and selected in REFERENCE EXAMPLE 2 were plated on 24-well plate at $7\times10^4$ cells/well and cultured for 48 hours. The cells were washed with αMEM medium (pH7.5) containing 0.2 mM 3-isobutyl-methylxanthine, 0.05% BSA and 20 mM HEPES (hereafter, αMEM medium (pH7.5) containing 0.2 mM 3-isobutyl-methylxanthine, 0.05% BSA and 20 mM HEPES may be referred to as a reaction buffer). Subsequently, 0.5 ml of the reaction buffer was added, and the solution was incubated for 30 minutes in the incubator. The reaction buffer was removed and 0.25 ml of the reaction buffer was freshly added to the cells. Then, the cells were admixed with a sample and 0.25 ml of the reaction buffer containing 2 μM forskoline, and incubated at 37° C. for 30 minutes. Intracellular cAMP was extracted by removing the reaction solution and adding 0.5 ml of the solution for cell lysis attached with cAMP EIA Kit (Applied Biosystems). The cAMP level in the extract was quantified with the same kit. Based on this measured value, a calculation was made using the following formula, and the promoting/inhibiting activity for cAMP production was represented by % of control. The activity of the sample-adding group was calculated using a control value configured in each plate.

% of control=$(X-C)/(T-C)\times100$

X: The cAMP level in the sample-adding group

T: The means of the cAMP level in 3 wells of positive control (no sample, with stimulus of forskoline)

C: The means of the cAMP level in 3 wells of negative control (no sample, without stimulus of forskoline)

Reference Example 4

Assay for Promoting Activity of Arachidonic Acid Metabolite Release Using TGR23-2 Expressing CHO Cells The CHO/TGR23-2 cells prepared in REFERENCE EXAMPLE 1 and selected in REFERENCE EXAMPLE 2 were plated on 24-well plate at $5\times10^4$ cells/well and cultured for 24 hours. After removing the medium, αMEM medium (pH7.4) supplemented with 0.5 μCi/ml [$^3$H] arachidonic acid, 100% dialyzed FBS, 20 mM HEPES and 0.5% BSA was added to the cells at 500 μl/well. Subsequently, the cells were incubated for 16 hours in the incubator. After the culture containing [$^3$H] arachidonic acid was discarded, 500 μl/well of αMEM medium (pH7.4) supplemented with 20 mM HEPES and 0.5% BSA were added, and the cells were incubated for 4 hours in the incubator. The culture medium was removed, and the cells were washed twice with 750 μl/well of Hanks' solution (pH7.4) supplemented with 0.05% BSA and 20 mM HEPES (hereafter, Hanks' solution (pH7.4) supplemented with 0.05% BSA and 20 mM HEPES was referred to as a reaction buffer). After washing, the cells were admixed with 750 μl/well of the reaction buffer and incubated for 40 minutes in the incubator. The reaction buffer was removed and 250 μl of the reaction buffer was freshly added. Then, a sample and 250 μl of the reaction buffer were added to the cells, and the cells were incubated at 37° C. for 40 minutes. After reaction, 350 μl of the supernatant were fractionated. Three milliliters of liquid scintilator were added to the supernatant described above to measure the radioactivity. Based on this measured value, a calculation was made using the following formula, and the promoting activity of arachidonic acid metabolite release was represented by % of control. The activity of the sample-adding group was calculated using a control value configured in each plate.

% of control=$(X-C)\times100$

X: The radioactivity in the sample-adding group

C: The means of the radioactivity in 4 wells of control (no sample)

Reference Example 5

Assay for Promoting Activity of Intracellular $Ca^{2+}$ Release Using TGR23-2 Expressing CHO Cells A promoting activity of intracellular $Ca^{2+}$ release was assayed using FLIPR (Molecular Devices, Inc.). The CHO/TGR23-2 cells prepared in REFERENCE EXAMPLE 1 and selected in REFERENCE EXAMPLE 2 were plated on 96-well plate at $3\times10^4$ cells/well and cultured for 24 hours. A loading buffer was prepared by adding 1 vial of Fluo 3-AM to 10 ml of Hanks' solution (pH7.4) containing 2.5 mM Probenecid and 20 mM HEPES (hereafter, Hanks' solution (pH7.4) containing 2.5 mM Probenecid and 20 mM HEPES may be referred to as a washing buffer). The culture medium was discarded from the culture plate and 100 μl/well of the loading buffer were added to the cells. Then the cells were incubated for 60 minutes in the incubator. After the loading buffer was removed from the culture plate and the cells were washed with the washing buffer, the plate was put in place of FLIPR. A sample was prepared by adding a sample buffer, which 2 mg/ml BSA and 1 mg/ml CHAPS were added to the washing buffer, to lyophilized product, stirring and treating by ultrasonication for 30 minutes, and transferred to 96-well sample plate. This sample plate was also put in place for assay. The promoting activity of intracellular $Ca^{2+}$ release was measured as an increase of fluorescent intensity, which is raised by addition of the sample.

Reference Example 6

Purification of an active substance, which specifically exhibits a promoting activity of cAMP production on TGR23-2 expressing CHO cells, from rat whole brain extracts A substance, which exhibits a ligand activity specific to TGR23-2 was purified from rat whole brain using a promoting activity of cAMP production on TGR23-2 expressing CHO cells as an index.

High Performance Liquid Chromatography (HPLC) fraction from rat whole brain extracts was prepared by the method described below. Four hundreds grams of a whole brain of 8 weeks old male Wistar rat (corresponding to 200 rats) available from Charles River Japan, Inc., were sequentially extirpated and boiled for 10 minutes in boiling distilled water (300 ml) in increments of 25 rats. After boiling, the samples were immediately chilled in ice and all of 200 samples were put together (2.4 L). One hundred and eighty milliliter of acetic acid was added to the samples to make the final concentration 1.0 M. Then the sample was homogenized with polytron (10,000 rpm, 2 minutes) under low temperature. The homogenized solution was centrifuged at 8,000 rpm for 30 minutes to get supernatant. To precipitate, 2.4 L of 1.0 M acetic acid was added, and homogenization was carried out again with polytron. After stirring for overnight, supernatant was acquired by centrifugation (8,000 rpm, 30 minutes). Two volumes of cold acetone (4.8 L) were dropped at 4° C. to each supernatant obtained from centrifugation. The supernatant obtained from the 1 st centrifugation was stirred for overnight and the 2nd supernatant was stirred for 4 hours. The extract, to which acetone was added, was centrifuged at 8,000 rpm for 30 minutes to discard precipitate. Acetone was removed from the supernatant obtained with evaporator under vacuum pressure. Equal volumes of diethylether were added to the extract after removal of acetone. Then the aqeous phase was recovered by isolating the ether phase containing lipids using separatory funnel. The extract, which was defatted with ether, was concentrated with evaporator under vacuum pressure, and ether was completely removed. After the concentrate was filtered through glass fiber filter paper (Advantech, DP70 (90 mmϕ)), the filtrate was applied to ODS column (Daiso, Daisogel IR-120-ODS-A 63/210 μm), which was filled in glass column (30ϕ×240 mm). The column was washed with 400 ml of 1.0 M acetic acid and eluted with 500 ml of 60% acetonitrile containing 0.1% trifluoracetic acid. The eluate was concentrated under vacuum prssure to remove solvent. Subsequently, the concentrate was lyophilized. The obtained white powder, 1.2 g, was dissolved in 30 ml of 10% acetonitrile containing 0.1% trifluoracetic acid. The solution obtained as described above, 12.5 ml each was applied to fractionated HPLC using ODS column (Toso, TSKgel ODS-80Ts (21.5ϕ×300 mm)) by elution with concentration gradient from 10% to 60% of acetonitrile containing 0.1% trifluoracetic acid. HPLC was carried out twice. The eluate was fractionated into 60 every 2 minutes, and the resultant was put together. Each fraction was concentrated and evaporated under vacuum pressure, and to the residual 0.4 ml of dimethylsulfoxide (DMSO) was added. Then the residual was completely dissolved using Vortex mixer and ultrasonicator.

Where the DMSO solution of HPLC fraction obtained as described above was administered to TGR23-2 expressing CHO cells according to the method shown in REFERENCE EXAMPLE 3, and a production level of intracellular cAMP was determined, a significant promoting activity for cAMP production was observed in the fraction numbers 18, 20 and 22 to 23. In addition, for the same sample, in accordance with the method shown in REFERENCE EXAMPLE 4, an arachidonic acid metabolite releasing activity was assayed. As the result, a siginificant activity was confirmed.

Since these activities were not observed in other receptor-expressing cells, it was shown that a ligand active substance specific to TGR23-2 is presented in rat whole brain extract. The 3 active fractions, which were obtained, were further purified by the following methods (a) to (c), respectively. Moreover, for each active fraction, the fraction observing a promoting activity for cAMP production, which was obtained in the purification process using the first cation exchange column, coincidentally possessed an intracellular calcium releasing activity specific to receptor, which was detected with FLIPR described in REFERENCE EXAMPLE 5. Thus, for confirmation of the activity in the subsequent purification processes, the intracellular calcium releasing activity with FLIPR was used as an index. The fact that the active fraction exhibits a promoting activity for cAMP production was appropriately confirmed.

(a) Fraction Number 18

The fraction number 18 was dissolved in 10 ml of 10 mM ammonium formate containing 100% acetonitrile, applied to cation exchange column (Toso, TSKgel SP-5PW (20 mmϕ× 150 mm) and eluted with concentration gradient from 10 mM to 1.0 M of ammonium formate containing 10% acetonitrile. The activity was recovered from around 0.4 M ammonium formate. After lyophilization, the active fraction was dissolved in 0.8 ml of 10% acetonitrile containing 0.1% trifluoracetic acid. Where the solution was applied to ODS column (Toso, TSKgel ODS-80Ts (4.6ϕ×250 mm)) and eluted with concentration gradient from 10% to 25% of acetonitrile containing 0.1% trifluoracetic acid, the activity was detected at around 13% acetonitrile. After lyophilization, the obtained active fraction was dissolved in 0.1 ml of DMSO. Further, 0.7 ml of 10% acetonitrile containing 0.1% heptafluor butyric acid was added to the above solution, and the solution thus obtained was applied to ODS column (Wako Pure Chemicals, Wakosil-II 3C18HG (2.0 mmϕ×150 mm)). The elution was carried out by concentration gradient of acetonitrile containing 0.1% heptafluor butyric acid from 10% to 37.5%, and each peak was manually fractionated. The activity was detected at around 26% acetonitrile. To the active fraction, 0.7 ml of 10% acetonitrile containing 0.1% trifluor acetic acid was added, and the fraction was applied to ODS column (Wako Pure Chemicals, Wakosil-II 3C18HG). The elution was carried out by concentration gradient of acetonitrile containing 0.1% trifluor acetic acid from 10% to 20%, and each peak was manually fractionated. The activity was recovered as a single peak at around 11% acetonitrile. Structure of an active substance, which is contained in this fraction, was determined as shown in REFERENCE EXAMPLE 10 described below.

(b) Fraction Number 20

The fraction number 20 was dissolved in 10 ml of 10 mM ammonium formate containing 10% acetonitrile, applied to cation exchange column (Toso, TSKgel SP-5PW (20 mmϕ× 150 mm) and eluted with concentration gradient from 10 mM to 1.0 M of ammonium formate containing 10% acetonitrile. The activity was recovered from around 0.6 M ammonium formate. After lyophilization, the active fraction was dissolved in 0.8 ml of 10% acetonitrile containing 0.1% trifluoracetic acid. Where the solution was applied to CN column (Nomura Chemicals, Develosil CN-UG-5 (4.6ϕ× 250 mm) and eluted with concentration gradient from 10% to 25% of acetonitrile containing 0.1% trifluoracetic acid, the activity was detected at around 12% acetonitrile. To the active fraction, 0.7 ml of 10% acetonitrile containing 0.1% trifluor acetic acid was added, and the fraction was applied to ODS column (Wako Pure Chemicals, Wakosil-II 3C18HG (2.0 mmϕ×150 mm)). The elution was carried out by concentration gradient of acetonitrile containing 0.1% trifluor acetic acid from 10% to 20%, and each peak of the eluate was manually fractionated. The activity was recovered as a single peak at around 15% acetonitrile. Structure of an active substance, which is contained in this fraction, was determined as shown in REFERENCE EXAMPLE 8 described below.

The fraction numbers 22 to 23 were dissolved in 10 ml of 10 mM ammonium formate containing 10% acetonitrile, applied to cation exchange column (Toso, TSKgel SP-5PW (20 mmϕ×150 mm) and eluted with concentration gradient from 10 mM to 1.0 M of ammonium formate containing 10% acetonitrile. The activity was recovered from around 0.4 M ammonium formate. After lyophilization, the active fraction was dissolved in 0.8 ml of 100% acetonitrile containing 0.1% trifluoracetic acid. Where the solution was applied to CN column (Nomura Chemicals, Develosil CN-UG-5 (4.6 mmϕ×250 mm) and eluted with concentration gradient from 10% to 25% of acetonitrile containing 0.1-% trifluoracetic acid, the activity was detected at around 13% acetonitrile. To the active fraction, 0.7 ml of 10% acetonitrile containing 0.1% trifluor acetic acid was added, and the fraction was applied to ODS column (Wako Pure Chemicals, Wakosil-II 3C18HG (2.0 mmϕ×150 mm)). The elution was carried out by concentration gradient of acetonitrile containing 0.1% trifluor acetic acid from 10% to 20%, and each peak was manually fractionated. The activity was recovered as a single peak at around 16% acetonitrile. To the active fraction, 0.7 ml of 10% acetonitrile containing 0.1% heptafluor butyric acid was added, and the solution thus obtained was applied to ODS column (Wako Pure Chemicals, Wakosil-II 3C18HG). The elution was carried out by concentration gradient of acetonitrile containing 0.1% heptafluor butyric acid from 10% to 37.5%, and each peak of the eluate was manually fractionated. The activity was obtained as a single peak at around 28% acetonitrile. Structure of an active substance, which is contained in this fraction, was determined as shown in REFERENCE EXAMPLE 9 described below.

Reference Example 7

Inactivation of an Active Substance in Rat Whole Brain Extracts, which Specifically Exhibits a Promoting Activity of cAMP Production on TGR23-2 Expressing CHO Cells, by Pronase The HPLC fractions 18, 20 and 22 to 23 exhibiting promoting activity for intracellular cAMP production on TGR23-2 expressing CHO cells in REFERENCE EXAMPLE 6 was treated with proteolytic enzyme, Pronase (Sigma, protease Type XIV (P5147)) in order to investigate whether the active substances may be protein, or not.

Four μl each of the above-mentioned HPLC active fractions of rat whole brain extracts (Fraction numbers 18, 20 and 22 to 23) was added to 100 μl of 0.2 M ammonium acetate and incubated at 37° C. for 2 hours with 3 μg of Pronase. Subsequently, Pronase was inactivated by heating in boiling water for 10 minutes. To this solution, 1 ml of distilled water containing 0.05 mg of BSA and 0.05 mg of CHAPS was added. Further, it was lyophilized. For the lyophilized sample, promoting activity for intracellular cAMP production was assayed by adding to TGR23-2 expressing CHO cells according to the method shown in REFERENCE EXAMPLE 3.

As the result, an activity of each fraction was completely diminished by treatment with Pronase.

Therefore, it was clarified that the active substances in rat whole brain extracts, which specifically exhibits a promoting activity of cAMP production on TGR23-2 expressing CHO cells are protein or peptide, respectively.

Reference Example 8

Determination of an Amino Acid Sequence of an Active Substance Obtained from the Fraction Number 20 in Rat Whole Brain Extracts, which Specifically Exhibits a Promoting Activity for cAMP Production on TGR23-2 Expressing CHO Cells As shown in REFERENCE EXAMPLE 7, since it was expected that the active substances specifically exhibiting promoting activity for cAMP production on TGR23-2 expressing CHO cells, which are contained in the three fractions of rat whole brain extracts, may be protein, respectively, an amino acid sequence for each fraction was analyzed as follows.

Determination of an amino acid sequence and mass spectrometry for the active substance obtained from the fraction number 20 in rat whole brain extracts as shown in REFERENCE EXAMPLE 6, which specifically exhibits a promoting activity for cAMP production on TGR23-2 expressing CHO cells, were carried out. As the result of amino acid sequence analysis of the amino terminus using eluate containing the active peak with Procise 491c LC Protein Sequencer (Applied Biosystems), the amino acid sequence from N terminus to the 18th residue having SFRNGVGSGVKKTSFRRA (SEQ ID NO: 25) was obtained. Where mass spectrometry was carried out using Thermo Finnigan LCQ ion trap mass spectrometer (ThermoQuest) equipped with nano spray ion sources (Protana), the mass weight calculating from the amino acid sequence represented by SEQ ID NO: 25 was found (the found value: 1954.9; the calculated value: 1954.2).

From the results, it was determined that the active substance obtained from the fraction number 20 in rat whole brain extracts, which specifically exhibits a promoting activity for cAMP production on TGR23-2 expressing CHO cells, have the amino acid sequence represented by SEQ ID NO: 25.

Reference Example 9

Determination of an Amino Acid Sequence of an Active Substance Obtained from the Fraction Numbers 22 and 23 in Rat Whole Brain Extracts, which Specifically Exhibits a Promoting Activity of cAMP Production on TGR23-2 Expressing CHO Cells Determination of an amino acid sequence and mass spectrometry for the active substance obtained from the fraction numbers 22 and 23 in rat whole brain extracts as shown in REFERENCE EXAMPLE 6, which specifically exhibits a promoting activity for cAMP production on TGR23-2 expressing CHO cells, were carried out. As the result of amino acid sequence analysis of the amino terminus using eluate containing the active peak with Procise 491 c LC Protein Sequencer (Applied Biosystems), the amino acid sequence from N terminus to the 15th residue having SFRNGVGSGVKKTSF (SEQ ID NO: 26) was obtained. Where mass spectrometry was carried out using Thermo Finnigan LCQ ion trap mass spectrometer (ThermoQuest) equipped with nano spray ion sources (Protana), the mass weight calculating from the amino acid sequence represented by SEQ ID NO: 0.26 was found (the found value: 1570.8; the calculated value: 1570.8).

From the results, it was determined that the active substance obtained from the fraction numbers 22 and 23 in rat whole brain extracts, which specifically exhibits a promoting activity for cAMP production on TGR23-2 expressing CHO cells, have the amino acid sequence represented by SEQ ID NO: 26.

Reference Example 10

Determination of an Amino Acid Sequence of an Active Substance Obtained from the Fraction Number 18 in Rat Whole Brain Extracts, which Specifically Exhibits a Promoting Activity of cAMP Production on TGR23-2 Expressing CHO Cells Determination of an amino acid sequence and mass spectrometry for the active substance obtained from the fraction number 18 in rat whole brain extracts as shown in REFERENCE EXAMPLE 6, which specifically exhibits a promoting activity for cAMP production on TGR23-2 expressing CHO cells, were carried out. As the result of amino acid sequence analysis of the amino terminus using eluate containing the active peak with Procise 491 c LC Protein Sequencer (Applied Biosystems), the amino acid sequence from N terminus to the 14th residue having SFRNGVGSGVKKTS (SEQ ID NO: 27) was obtained. Where mass spectrometry was carried out using Thermo Finnigan LCQ ion trap mass spectrometer (ThermoQuest) equipped with nano spray ion sources (Protana), the mass weight calculating from the amino acid sequence represented by SEQ ID NO: 27 was found (the found value: 1424.1; the calculated value: 1423.6).

From the results, it was determined that the active substance obtained from the fraction number 18 in rat whole brain extracts, which specifically exhibits a promoting activity for cAMP production on TGR23-2 expressing CHO cells, have the amino acid sequence represented by SEQ ID NO: 27.

Reference Example 11

Cloning of cDNA Encoding Human TGR23-2 Ligand Precursor

In order to clone cDNA encoding a precursor of human homologue (in the specification, sometimes referred to as human TGR23-2 ligand) for an active peptide exhibiting a promoting activity for cAMP production specific to TGR23-2 expressing CHO cells, which is obtained from rat whole brain extracts (in the specification, referred to as rat TGR23-2 ligand), using cDNA derived from human hypothalamus as a template, PCR was carried out.

Using the following synthetic DNA primers and cDNA derived from human hypothalamus as a template, amplification by PCR method was performed. The reaction solution in the above reaction comprised of 0.8 μl of human hypothalamus Marathon Ready cDNA (CLONTECH), 1.0 μM each of synthetic DNA primers represented by SEQ ID NO: 28 and SEQ ID NO: 29, 0.2 mM dNTPs, 0.1 μl of ExTaq (Takara Shuzo) and ExTaq Buffer attached to the enzyme to make the total volume 20 μl. The PCR reaction was carried out using a thermal cycler (PE Biosystems) by heating of 94° C. for 300 seconds, then a cycle set to include 94° C. for 10 seconds followed by 55° C. for 30 seconds and 72° C. for 30 seconds, which was repeated 35 times, and finally, extension reaction at 72° C. for 5 minutes. Subsequently, 2 μl of the PCR reaction solution diluted by 50-fold with DNase, Rnase-free distilled water, 1.0 μM each of synthetic DNA primers represented by SEQ ID NO: 28 and SEQ ID NO: 30, 0.2 mM dNTPs, 0.1 μl of ExTaq polymerase (Takara Shuzo) and ExTaq Buffer attached to the enzyme were made to 20 μl of total volume. The reaction solution was incubated using a thermal cycler (PE Biosystems) by heating of 94° C. for 300 seconds, then a cycle set to include 94° C. for 10 seconds followed by 55° C. for 30 seconds and 72° C. for 30 seconds, which was repeated 35 times, and finally, extension reaction at 72° C. for 5 minutes. The amplified DNA was separated by 2.0% agarose gel electrophoresis and the band of the DNA was excised by razor blade. The DNA was recovered using QIAquick Gel Extraction Kit (Qiagen). This DNA was cloned to pGEM-T Easy vector in accordance with the protocol of pGEM-T Easy Vector System (Promega). After transformation of *Escherichia coli* JM109 competent cell (Takara Shuzo) by introducing the above-mentioned vector, clones harboring cDNA insert fragment was selected on LB agar medium containing ampicillin and X-gal. All the white-colored clones were isolated with sterilized toothpick, then the transformants were obtained. Respective clones were cultured in LB medium containing ampicillin for overnight. Subsequently, the plasmid DNA was prepared using QIAwell 8 Plasmid Kit (Qiagen). The reaction for determination of the base sequence was carried out using BigDye Terminator Cycle Sequencing Ready Reaction Kit (PE Biosystems). As a result, after decoding with the fluorescent automated sequencer, the DNA sequence represented by SEQ ID NO: 31, was obtained.

Since in the base sequence of the DNA represented by SEQ ID NO: 31, a frame encoding extremely similar amino acid sequence to that of rat TGR23-2 ligand obtained from rat whole brain, which are represented by SEQ ID NO: 25, SEQ ID NO: 26 and SEQ ID NO: 27 exits, it was presumed that the DNA are cDNA encoding a precursor or a portion of human TGR23-2 ligand.

In the frame encoding an amino acid sequence that is considered to be human TGR23-2 ligand, there exists two ATG, which are expected to be a translation initiation codon, upstream of 5'-end of the amino acid sequence translated from the sequence represented by SEQ ID NO: 31. When hydrophobicity was plotted, since high hydrophobic region, which was expected to be a signal sequence, was appeared in the case when it was translated from ATG located further upstream of 5'-end, it was presumed that this ATG was an initiation codon. In 3'-end, there was a termination codon downstream of the sequence, which was considered that human TGR23-2 ligand was encoded. The amino acid sequence of human TGR23-2 ligand precursor deduced from these results is shown as SEQ ID NO: 32. In this sequence, there exists Lys-Arg sequence, which physiologically active substances are generally excised from its precursor protein (Seidah, N. G. et al., Ann. N.Y. Acad. Sci., Vol. 839, pp. 9-24, 1998) in the N-terminus of the amino acid sequence corresponding to human TGR23-2 ligand. On the other hand, in the C-terminus, there exists a termination codon. In addition, there exists two more residues between termination codon and the sequence corresponding to rat TGR23-2 ligand having an amino acid sequence represented by SEQ ID NO: 25.

From these results, it was presumed that the amino acid sequence of human TGR23-2 ligand was the amino acid sequences represented by SEQ ID NO: 33 [human TGR23-2 ligand (1-18)], SEQ ID NO: 34 [human TGR23-2 ligand (1-15)] and SEQ ID NO: 35 [human TGR23-2 ligand (1-14)], wherein the above-mentioned sequences were corresponded to the amino acid sequences of rat TGR23-2 ligand: SEQ ID NO: 25 [rat TGR23-2 ligand (1-18)], SEQ ID NO: 26 [rat TGR23-2 ligand (1-15)] and SEQ ID NO: 27 [rat TGR23-2 ligand (1-14)], respectively; and further the amino acid sequence represented by SEQ ID NO: 36 [human TGR23-2 ligand (1-20)], to which two residues were extended in the C-terminus of the sequence represented by SEQ ID NO: 33. In addition, since the sequence of human TGR23-2 ligand has not Arg-Arg sequence, but Glu-Arg sequence, which characteristic is different from that of the sequences of mouse TGR23-2 ligand and rat TGR23-2 ligand, it was presumed that the amino acid sequence having 16 residues represented by SEQ ID NO: 62 [human TGR23-2 ligand (1-16)] was also a ligand sequence.

Reference Example 12

Cloning of cDNA Encoding Mouse TGR23-2 Ligand Precursor

In order to clone cDNA encoding a precursor of mouse homologue (in the specification, sometimes referred to as mouse TGR23-2 ligand) for rat TGR23-2 ligand, which is obtained from rat whole brain extracts, using cDNA derived from mouse whole brain as a template, PCR was carried out.

Using the following synthetic DNA primers and cDNA derived from mouse whole brain as a template, amplification by PCR method was performed. The reaction solution in the above reaction comprised of 0.8 μl of mouse whole brain Marathon Ready cDNA (CLONTECH), 1.0 μM each of synthetic DNA primers represented by SEQ ID NO: 37 and SEQ ID NO: 38, 0.2 mM dNTPs, 0.1 μl of ExTaq (Takara Shuzo) and ExTaq Buffer attached to the enzyme to make the total volume 20 μl. The PCR reaction was carried out using a thermal cycler (PE Biosystems) by heating of 94° C. for 5 minutes, then a cycle set to include 94° C. for 10 seconds followed by 65° C. for 30 seconds and 72° C. for 30 seconds, which was repeated 35 times, and finally, extension reaction at 72° C. for 5 minutes. Subsequently, 2 μl of the PCR reaction solution diluted by 100-fold with DNase, Rnase-free distilled water, 1.0 μM each of synthetic DNA primers represented by SEQ ID NO: 37 and SEQ ID NO: 39, 0.2 mM dNTPs, 0.1 μl of ExTaq polymerase (Takara Shuzo) and ExTaq Buffer attached to the enzyme were made to 20 μl of total volume. The reaction solution was incubated using a thermal cycler (PE Biosystems) by heating of 94° C. for 5 minutes, then a cycle set to include 94° C. for 10 seconds followed by 60° C. for 30 seconds and 72° C. for 30 seconds, which was repeated 30 times, and finally, extension reaction at 72° C. for 5 minutes. The amplified DNA was separated by 2.0% agarose gel electrophoresis and the DNA having about 440 bases length was excised by razor blade. The DNA was recovered using QIAquick Gel Extraction Kit (Qiagen). This DNA was cloned to pGEM-T Easy vector in accordance with the protocol of pGEM-T Easy Vector System (Promega). After transformation of *Escherichia coli* JM109 competent cell (Takara Shuzo) by introducing the above-mentioned vector, clones harboring cDNA insert fragment was selected on LB agar medium containing ampicillin and X-gal. All the white-colored clones were isolated with sterilized toothpick, then the transformants were obtained. Respective clones were cultured in LB medium containing ampicillin for overnight. Subsequently, the plasmid DNA was prepared using QIAwell 8 Plasmid Kit (Qiagen). The reaction for determination of the base sequence was carried out using BigDye Terminator Cycle Sequencing Ready Reaction Kit (PE Biosystems). As a result, after decoding with the fluorescent automated sequencer, the DNA sequence represented by SEQ ID NO: 40, was obtained.

Since in the base sequence of the DNA represented by SEQ ID NO: 40, a frame encoding extremely similar amino acid sequence to that of rat TGR23-2 ligand obtained from rat whole brain, which are represented by SEQ ID NO: 25, SEQ ID NO: 26 and SEQ ID NO: 27 exits, it was presumed that the DNA are cDNA encoding a precursor or a portion of mouse TGR23-2 ligand.

In the frame encoding an amino acid sequence that is considered to be mouse TGR23-2 ligand, there exists two ATG, which are expected to be a translation initiation codon, upstream of 5'-end of the amino acid sequence translated from the sequence represented by SEQ ID NO: 40. When hydrophobicity was plotted, since high hydrophobic region, which was expected to be a signal sequence, was appeared in the case when it was translated from ATG located further upstream of 5'-end, it was presumed that this ATG was an initiation codon. In 3'-end, there was a termination codon downstream of the sequence, which was considered that mouse TGR23-2 ligand was encoded. The amino acid sequence of mouse TGR23-2 ligand precursor deduced from these results is shown as SEQ ID NO: 41. In this sequence, there exists Lys-Arg sequence, which physiologically active substances are generally excised from its precursor protein (Seidah, N. G. et al., Ann. N.Y. Acad. Sci., Vol. 839, pp. 9-24, 1998) in the N-terminus of the amino acid sequence corresponding to human TGR23-2 ligand. On the other hand, in the C-terminus, there exists a termination codon. In addition, there exists two more residues between termination codon and the sequence corresponding to rat TGR23-2 ligand having an amino acid sequence represented by SEQ ID NO: 25.

From these results, it was presumed that the amino acid sequence of mouse TGR23-2 ligand was the amino acid sequences represented by SEQ ID NO: 42 [mouse TGR23-2 ligand (1-18)], SEQ ID NO: 43 [mouse TGR23-2 ligand (1-15)] and SEQ ID NO: 44 [mouse TGR23-2 ligand (1-14)], wherein the above-mentioned sequences were corresponded to the amino acid sequences of rat TGR23-2 ligand: SEQ ID NO: 25 [rat TGR23-2 ligand (1-18)], SEQ ID NO: 26 [rat TGR23-2 ligand (1-15)] and SEQ ID NO: 27 [rat TGR23-2 ligand (1-14)], respectively; and further the amino acid sequence represented by SEQ ID NO: 45 [mouse TGR23-2 ligand (1-20)], to which two residues were extended in the C-terminus of the sequence represented by SEQ ID NO: 42.

Reference Example 13

Cloning of cDNA Encoding a Portion of Rat TGR23-2 Ligand Precursor

In order to clone cDNA encoding a precursor of rat TGR23-2 ligand, using cDNA derived from rat whole brain as a template, PCR was carried out.

Using the following synthetic DNA primers and cDNA derived from rat whole brain as a template, amplification by PCR method was performed. The reaction solution in the above reaction comprised of 0.8 μl of rat whole brain Marathon Ready cDNA (CLONTECH), 1.0 μM each of synthetic DNA primers represented by SEQ ID NO: 46 and SEQ ID NO: 38, 0.2 mM dNTPs, 0.1 μl of ExTaq (Takara Shuzo) and ExTaq Buffer attached to the enzyme to make the total volume 20 μl. The PCR reaction was carried out using a thermal cycler (PE Biosystems) by heating of 94° C. for 5 minutes, then a cycle set to include 94° C. for 10 seconds followed by 65° C. for 30 seconds and 72° C. for 30 seconds, which was repeated 35 times, and finally, extension reaction at 72° C. for 5 minutes. Subsequently, 2 μl of the PCR reaction solution diluted by 100-fold with DNase, Rnase-free distilled water, 1.0 μM of primer represented by SEQ ID NO: 46, 0.2 μM of primer represented by SEQ ID NO: 39, 0.2 mM dNTPs, 0.1 μl of ExTaq polymerase (Takara Shuzo) and ExTaq Buffer attached to the enzyme were made to 20 μl of total volume. The reaction solution was incubated using a thermal cycler (PE Biosystems) by heating of 94° C. for 5 minutes, then a cycle set to include 94° C. for 10 seconds followed by 60° C. for 30 seconds and 72° C. for 30 seconds, which was repeated 30 times, and finally, extension reaction at 72° C. for 5 minutes. The amplified DNA was separated by 2.0% agarose gel electrophoresis and the DNA having about 200 bases length was excised by razor blade. The DNA was recovered using QIAquick Gel Extraction Kir (Qiagen). This DNA was cloned to pGEM-T Easy vector in accordance with the protocol of pGEM-T Easy Vector System (Promega). After transformation of *Escherichia coli* JM109 competent cell (Takara Shuzo) by introducing the above-mentioned vector, clones harboring cDNA insert fragment was selected on LB agar medium containing ampicillin and X-gal. All the white-colored clones were isolated with sterilized toothpick, then the transformants were obtained. Respective clones were cultured in LB medium containing ampicillin for overnight. Subsequently, the plasmid DNA was prepared using QIAwell 8 Plasmid Kit (Qiagen). The reaction for determination of the base sequence was carried out using BigDye Terminator Cycle Sequencing Ready Reaction Kit (PE Biosystems). As a result, after decoding with the fluorescent automated sequencer, the DNA sequence represented by SEQ ID NO: 47, was obtained.

In the base sequence of the DNA represented by SEQ ID NO: 47, there exists a frame encoding an amino acid sequence of rat TGR23-2 ligand obtained from rat whole brain, which are represented by SEQ ID NO: 25, SEQ ID NO: 26 and SEQ ID NO: 27. Where the DNA sequence was translated using this frame as a reading frame, the amino acid sequence represented by SEQ ID NO: 48 was obtained. As compared this sequence with the amino acid sequence of mouse TGR23-2 ligand precursor (SEQ ID NO: 40) that was obtained in REFERENCE EXAMPLE 12, it was presumed that this sequence corresponds to a sequence consisting of 54 amino acids at the C-terminus, which is a portion of rat TGR23-2 ligand precursor. In 3'-end, there was a termination codon downstream of the sequence, which was considered that rat TGR23-2 ligand was encoded. In this sequence, there exists Lys-Arg sequence, which physiologically active substances are generally excised from its precursor protein (Seidah, N. G. et al., Ann. N.Y. Acad. Sci., Vol. 839, pp. 9-24, 1998) in the N-terminus of the amino acid sequence corresponding to human TGR23-2 ligand. On the other hand, in the C-terminus, there exists a termination codon. In addition, there exists two more residues between termination codon and the sequence corresponding to rat TGR23-2 ligand having an amino acid sequence represented by SEQ ID NO: 25.

From these results, it was presumed that the amino acid sequence of rat TGR23-2 ligand was the amino acid sequences represented by SEQ ID NO: 25 [rat TGR23-2 ligand (1-18)], SEQ ID NO: 26 [rat TGR23-2 ligand (1-15)] and SEQ ID NO: 27 [rat TGR23-2 ligand (1-14)], and further the amino acid sequence represented by SEQ ID NO: 49 [rat TGR23-2 ligand (1-20)], to which two residues were extended in the C-terminus of the sequence represented by SEQ ID NO: 25.

Reference Example 14

Cloning of cDNA Encoding rat TGR23-2 Ligand Precursor

In order to clone cDNA encoding a precursor of rat TGR23-2 ligand, using cDNA derived from rat whole brain as a template, PCR was carried out.

Using the following synthetic DNA primers and cDNA derived from rat whole brain as a template, amplification by PCR method was performed. The reaction solution in the above reaction comprised of 0.8 μl of rat whole brain Marathon Ready cDNA (CLONTECH), 1.0 μM each of synthetic DNA primers represented by SEQ ID NO: 68 and SEQ ID NO: 69, 0.2 mM dNTPs, 0.1 μl of ExTaq (Takara Shuzo) and ExTaq Buffer attached to the enzyme to make the total volume 20 μl. The PCR reaction was carried out using a thermal cycler (PE Biosystems) by heating of 94° C. for 5 minutes, then a cycle set to include 94° C. for 10 seconds followed by 65° C. for 30 seconds and 72° C. for 30 seconds, which was repeated 35 times, and finally, extension reaction at 72° C. for 5 minutes. Subsequently, 2 μl of the PCR reaction solution diluted by 50-fold with DNase, Rnase-free distilled water, 1.0 μM of primer represented by SEQ ID NO: 70, 0.2 μM of primer represented by SEQ ID NO: 69, 0.2 mM dNTPs, 0.1 μl of ExTaq polymerase (Takara Shuzo) and ExTaq Buffer attached to the enzyme were made to 20 μl of total volume. The reaction solution was incubated using a thermal cycler (PE Biosystems) by heating of 94° C. for 5 minutes, then a cycle set to include 94° C. for 10 seconds followed by 65° C. for 30 seconds and 72° C. for 30 seconds, which was repeated 30 times, and finally, extension reaction at 72° C. for 5 minutes. The amplified DNA was separated by 2.0% agarose gel electrophoresis and the DNA having about 350 bases length was excised by razor blade. The DNA was recovered using QIAquick Gel Extraction Kir (Qiagen). This DNA was cloned to pGEM-T Easy vector in accordance with the protocol of pGEM-T Easy Vector System (Promega). After transformation of *Escherichia coli* JM109 competent cell (Takara Shuzo) by introducing the above-mentioned vector, clones harboring cDNA insert fragment was selected on LB agar medium containing ampicillin and X-gal. All the white-colored clones were isolated with sterilized toothpick, then the transformants were obtained. Respective clones were cultured in LB medium containing ampicillin for overnight. Subsequently, the plasmid DNA was prepared using QIAwell 8 Plasmid Kit (Qiagen). The reaction for determination of the base sequence was carried out using BigDye Terminator Cycle Sequencing Ready Reaction Kit (PE Biosystems). As a result, after decoding with the fluorescent automated sequencer, the DNA sequence represented by SEQ ID NO: 71, was obtained.

The base sequence of the DNA represented by SEQ ID NO: 71, was a sequence, wherein the DNA sequence encoding a portion of rat TGR23-2 ligand precursor obtained in REFERENCE EXAMPLE 13 (SEQ ID NO: 47) was further extended to 5' direction. Where the DNA sequence was translated using a frame encoding an amino acid sequence identical to that of rat TGR23-2 ligand precursor obtained from rat whole brain, which are represented by SEQ ID NO: 25, SEQ ID NO: 26 and SEQ ID NO: 27 as a reading frame, there was one site of ATG in 5' upstream at the position corresponding to ATG, which is presumed to be an initiation codon of protein translation that located in cDNA (SEQ ID NO: 31 and SEQ ID NO: 40) being expected to encode human TGR23-2 ligand precursor and mouse TGR23-2 ligand precursor. In addition, in further upstream of 5'-end of this ATG codon, a termination codon was appeared on the same frame. In 3'-end, there was a termination codon downstream of the sequence, which was considered that mouse TGR23-2 ligand was encoded. From these results, it was presumed that the sequence represented by SEQ ID NO: 71 was the cDNA sequence encoding rat TGR23-2 ligand precursor. The amino acid sequence translated from the base sequence of cDNA represented by SEQ ID NO: 71 is shown as SEQ ID NO: 72.

Reference Example 15

Preparation of TGR23-1 (Hereinafter, Sometimes Human TGR23-1 is Merely Referred to as TGR23-1) Expressing CHO Cells Using the plasmid pTB2173 obtained in EXAMPLE 1 as a template and two primers, namely, primer 1 attached to Sal I recognition sequence (SEQ ID NO: 20) and primer 2 attached to Spe I recognition sequence (SEQ ID NO: 21), PCR was carried out. The reaction solution in the above reaction comprised of 10 ng of the plasmid as a template, 2.5 U of Pfu Turbo DNA Polymerase (STRATAGENE), 1.0 μM each of primer 1 (SEQ ID NO: 20) and primer 2 (SEQ ID NO: 21), 200 μM of dNTPs, and 25 μl of 2xGC Buffer I (Takara) to make the total volume 50 μl. The PCR reaction was carried out by reaction of 95° C. for 1 minute, then a cycle set to include 95° C. for 60 seconds followed by 95° C. for 60 seconds, 55° C. for 60 seconds and 72° C. for 70 seconds, which was repeated 25 times, and finally, extension reaction at 72° C. for 10 minutes. The PCR product was subcloned into plasmid vector pCR-Blunt II-TOPO (Invitrogen) following the instructions attached to the Zero Blunt TOPO PCR Cloning Kit (Invitrogen). The plasmid was then introduced into *Escherichia coli* TOP10 (Invitrogen), and the clones having the cDNA of TGR23-1, which is contained in pTB2173, were selected on LB agar plates containing kanamycin. From *E. coli* clones transformed by the plasmid thus obtained, in which the TGR23-1 was introduced, the plasmid was prepared using Plasmid Miniprep Kit (BIO RAD) and digested with the restriction enzymes Sal I and Spe I to excise the insert, wherein TGR23-1 was attached to Sal I recognition sequence at 5' end and Spe I recognition sequence at 3' end. The insert DNA was electrophoresed to excise from agarose gel and recovered using the Gel Extraction Kit (Qiagen). This insert DNA was added to the expression vector plasmid for animal cells, pAKKO-111H (the same vector plasmid as pAKKO1.11H described in Biochim. Biophys. Acta, Vol. 1219, pp. 251-259 (1994) by Hinuma, S. et al.), which has been cleaved with Sal I and Spe I, and both DNAs were ligated by the DNA Ligation Kit Ver. 2 (Takara Shuzo). Thus, the plasmid pAKKO-TGR23-1 for protein expression was constructed. After cultivating *E. coli* TOP10 transformed with this pAKKO-TGR23-1, plasmid DNA of pAKKO-TGR23-1 was prepared using Plasmid Miniprep Kit (BIO RAD). $1\times10^5$ cells of hamster CHO/dhfr$^-$ cell were seeded in Falcon dish (3.5 cm diameter) with α-MEM medium (with ribonucleosides and deoxyribonucleosides, GIBCO, Cat No. 12571) containing 10% Fetal Bovine Serum, and cultivated at 37° C. for overnight in 5% $CO_2$ incubater. Two μg of the above-mentioned expression plasmid, pAKKO-TGR23-1 was transfected using Transfection Reagent FuGENE 6 (Roche) in accordance with the procedures described in the attached instruction. After 18 hours of cultivation, the medium was exchanged to a fresh medium for growth. Further cultivation for 10 hours, the transfected cells were harvested by treatment with Trypsin-EDTA, and seeded to 10 of 96-well flat bottomed plates with a selection medium (α-MEM medium (without ribonucleosides and deoxyribonucleosides, GIBCO, Cat No. 12561) containing 10% dialyzed Fetal Bovine Serum). Cultivation was continued while the selection medium was exchanged every 3 or 4 days, and 81 clones of DHFR$^+$ cell, which grew as a colony, were acquired after 2 or 3 weeks.

Reference Example 16

Quantification of TGR23-1 Expression Level in TGR23-1 Expressing CHO Cell Lines Using TaqMan PCR Method The 81 clones of TGR23-1 expressing CHO cells obtained in REFERENCE EXAMPLE 15 were cultured in the 96-well plate, and total RNA was prepared using RNeasy 96 Kit (Qiagen). Using 50 to 200 ng of total RNA obtained and TaqMan Gold RT-PCR Kit (PE Biosystems), a reverse transcription reaction was performed. Using 25 μl of the reaction mixture containing a reverse transcript corresponding to 5 to 20 ng of the total RNA obtained or a standard cDNA prepared as described below, 1× Universal PCR Master Mix (PE Biosystems), 500 nM each of primers represented by SEQ ID NO: 22 and SEQ ID NO: 23, and 100 nM TaqMan probe represented by SEQ ID NO: 24 (Fam-acctggtttg ccgagtggtc cgctattt-Tamra; in the sequence, Fam and Tamra represent 6-carboxy-fluorescein and 6-carboxy-tetramethyl-rhodamine, respectively), PCR was performed with ABI PRISM 7700 Sequence Detector (PE Biosystems). The PCR was carried out by reaction of 50° C. for 2 minutes and 95° C. for 10 minutes, then a cycle set to include 95° C. for 15 seconds followed by 60° C. for 60 seconds, which was repeated 40 times.

After concentration of the plasmid pTB2174 obtained in EXAMPLE 1 was calculated by measuring absorbance at 260 nm and accurate copy numbers were calculated, 2 to $2\times10^6$ copies of standard cDNA solution were prepared by diluting with 10 mM Tris-HCl (pH8.0) containing 1 mM EDTA. In addition, probe and primers for TaqMan PCR were designed by Primer Express Version 1.0 (PE Biosystems).

The expression level was calculated by ABI PRISM 7700 SDS Software. Cycle numbers at the moment when fluorescent intensity of reporter comes to preset values indicated as a vertical axis, and logarithm of an initial concentration of the standard cDNA as a horizontal axis. From this standard curve, the expression level of TGR23-1 gene per total RNA of each clone was found by calculating an initial concentration of each reverse transcript. As a result, 11 clones of CHO cell lines, in which the expression of TGR23-1 was high, were selected and cultured in 24-well plate. For these cells, the expression level of TGR23-2 was re-examined. After preparation of total RNA with Rneasy Mini Kits (Qiagen), the RNA was treated with DNase by RNase-free DNase Set (Qiagen). From total RNA obtained, the reverse transcription reaction was carried out in the same manner as described above, and the expression level of TGR23-1 gene per total RNA of each clone was found by the TaqMan PCR method. From this, it was revealed that the clones No. 49 and No. 52 of CHO cell lines expressing TGR23-1 were highly expressed.

In REFERENCE EXAMPLES described below, these two clones of the TGR23-1 expressing cells were used.

Reference Example 17

Manufacture of Human TGR23-2 Ligand (1-20): Ser-Phe-Arg-Asn-Gly-Val-Gly-Thr-Gly-Met-Lys-Lys-Thr-Ser-Phe-Gln-Arg-Ala-Lys-Ser (SEQ ID NO: 36)

Commercially available Boc-Ser(Bzl)-$OCH_2$-PAM resin was charged in a reaction tank of peptide synthesizer, ACT90. After swelling with DCM, the resin was treated with TFA to remove Boc and neutralized with DI EA. The resin was suspended in NMP and Boc-Lys(Cl-Z) was condensed to the amino group by the HOBt-DIPCI. Ninhydrin test was conducted to examine if any unreacted amino group was present. Where the ninhydrin test was positive, the same amino acid was condensed again. Where the ninhydrin test was also positive after re-condensation, peptide was acethylated with acetic anhydrite. By repeating this cycle, Boc-Ala, Boc-Arg(Tos), Boc-Gln, Boc-Phe, Boc-Ser(Bzl), Boc-Thr(Bzl), Boc-Lys(Cl-Z), Boc-Met, Boc-Gly, Boc-Thr(Bzl), Boc-Gly, Boc-Val, Boc-Gly, Boc-Asn, Boc-Arg(Tos), Boc-Phe and Boc-Ser(Bzl) were condensed in this order. As a result, 0.24 g of protected peptide resin, which was desired, was obtained. The resin was reacted in about 15 ml of hydrogen fluoride together with 1.5 ml of p-cresol at 0° C. for 60 minutes. After removing the hydrogen fluoride by distillation in vacuum, diethyl ether was added to the residue, and filtrated. Water and acetic acid were added to the filtrate in order to extract the peptide. Finally, it was separated from the resin. The extract was concentrated, and the concentrate obtained was applied to a column of Sephadex (trade mark) G-25 (2.0×80 cm) equilibrated with 50% acetic acid, developed with the same solvent. Main fractions were collected and lyophilized. The part of the peptide (45 mg) was applied to a reversed phase column (2.6×60 cm) filled up with LiChroprep (trade name) RP-18 followed by carrying out the washing with 200 ml of 0.1% aqueous TFA and the linear gradient elution using 300 ml of 0.1% aqueous TFA and 300 ml of 25% acetonitrile aqueous solution containing 0.1% TFA. Main fractions were collected and lyophilized to give 12.7 mg of objective peptide.

ESI-MS: molecular weight MW 2188.0 (theoretical value 2187.5) Elution time on HPLC: 10.6 minutes Column Conditions: Column: Wakosil 5C18T (4.6×100 mm) Eluant: linear density gradient elution (25 minutes) with A/B: 95/5 to 45/55, using solution A (0.1% TFA) and solution B (acetonitrile solution containing 0.1% TFA) Flow rate: 1.0 m/min.

Reference Example 18

Figure 14:
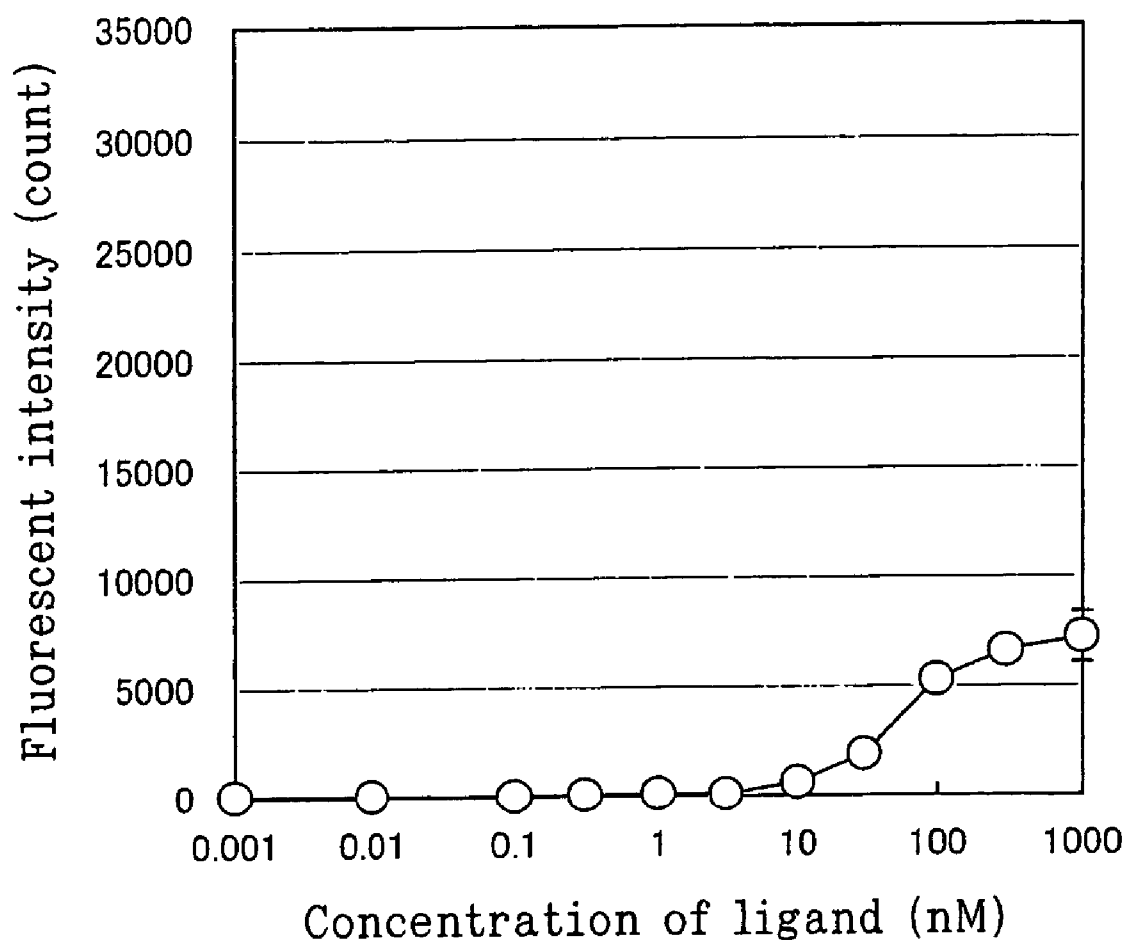
FIG. 14 shows an activity of increasing intracellular Ca ion concentration in TGR23-1 expressing CHO cell using various concentration of human TGR23-2 ligand (1-20) measured by FLIPR.
Figure 15:
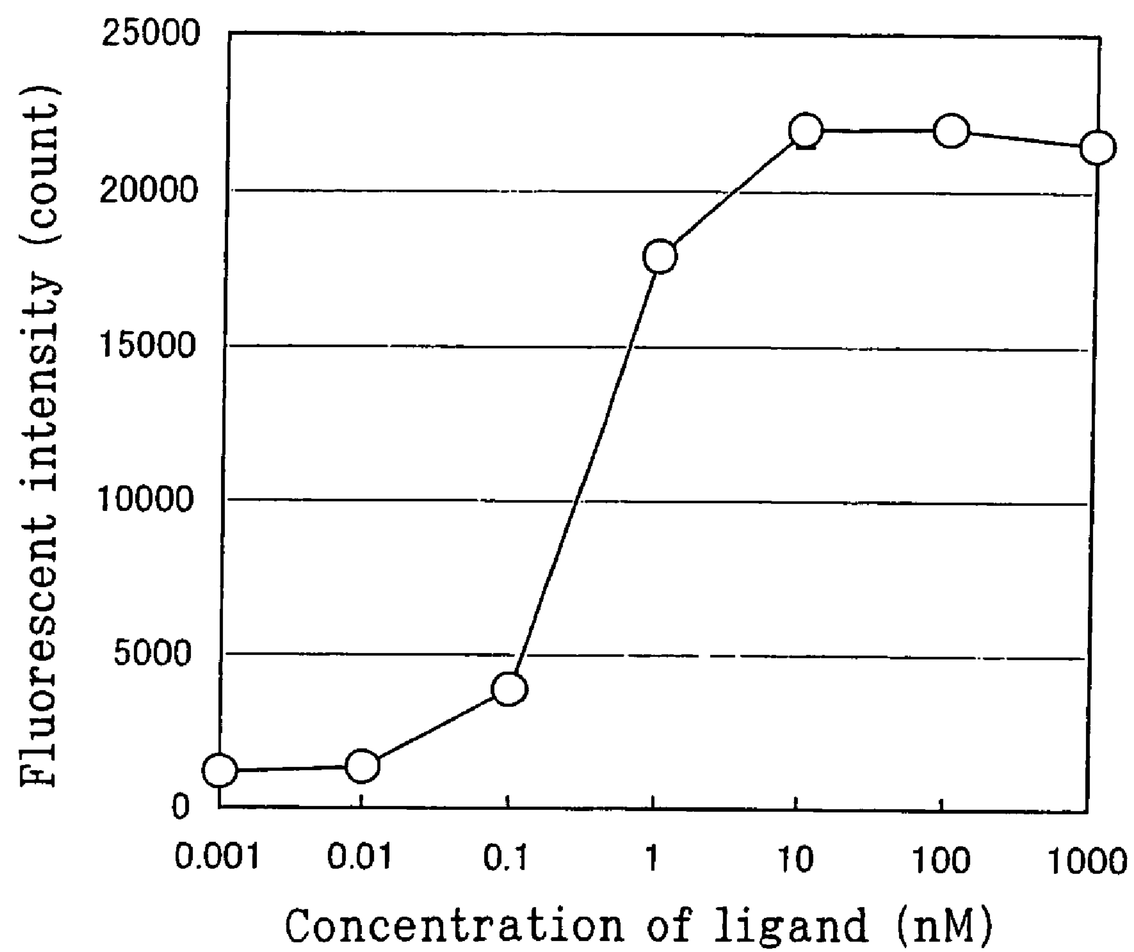
FIG. 15 shows an activity of increasing intracellular Ca ion concentration in TGR23-2 expressing CHO cell using various concentration of human TGR23-2 ligand (1-20) measured by FLIPR.

Assay for Increasing Activity of Intracellular Ca Ion Concentration on TGR23-1 Expressing CHO Cells and TGR23-2 Expressing CHO Cells by Human TGR23-2 Ligand (1-20) Using FLIPR Human TGR23-2 ligand (1-20) obtained in EXAMPLE 17 was administered to TGR23-1 expressing CHO cells and TGR23-2 expressing CHO cells at a variety of concentrations according to the method described in REFERENCE EXAMPLE 5, and the increasing activity of intracellular Ca ion concentration was determined using FLIPR. As a result, human TGR23-2 ligand (1-20) promotes an increase of intracellular Ca ion concentration on TGR23-1 expressing CHO cells and TGR23-2 expressing CHO cells depending on the concentration. The results are shown in FIG. 14 and FIG. 15.

From these results, it is clear that the polypeptide having an amino acid sequence represented by SEQ ID NO: 36 [human TGR23-2 ligand (1-20)] possesses an increasing activity of intracellular Ca ion concentration on TGR23-1 expressing CHO cells and TGR23-2 expressing CHO cells.

INDUSTRIAL APPLICABILITY

The G protein-coupled receptor protein of the present invention, its partial peptides, or salts thereof and the polynucleotides encoding the receptor protein or its partial peptide (e.g. DNA, RNA, and its derivatives) can be used for; (1) determination of ligands (agonists); (2) preparation of antibodies and antisera; (3) construction of recombinant receptor protein expression systems; (4) development of the receptor binding assay systems using the expression systems and screening of pharmaceutical candidate compounds; (5) effecting drug design based on comparison with structurally similar ligand receptors; (6) reagents for preparation of probes and PCR primers for gene diagnosis; (7) production of transgenic animals; and (8) drugs for the gene prophylaxis and gene therapy.

The invention claimed is:

1. An isolated G protein-coupled receptor protein having the amino acid sequence of SEQ ID NO: 3, or a salt thereof.

2. A method of manufacturing the isolated G protein-coupled receptor protein or its salt according to claim 1 which comprises culturing a host cell transformed with an expressible recombinant vector encoding for said protein for sufficient time and under conditions to produce said protein, and producing the G protein-coupled receptor protein according to claim 1.

3. An isolated polynucleotide containing a polynucleotide encoding the amino acid sequence of SEQ ID NO: 3.

4. An isolated polynucleotide according to claim 3, which is DNA.

5. An isolated DNA according to claim 4, having the nucleic acid sequence of SEQ ID NO: 4.

6. A recombinant vector containing the isolated polynucleotide according to claim 3.

7. A transformed host cell which has been transformed with the recombinant vector according to claim 6.

8. A diagnostic product comprising the polynucleotide according to claim 3.

9. The diagnostic product according to claim 8, which is a diagnostic product for colon cancer.

10. A diagnostic product, which comprises combining (i) the polynucleotide according to claim 3 and (ii) a polynucleotide encoding the amino acid sequence represented by SEQ ID NO: 16, or a polynucleotide encoding a G protein coupled receptor protein having an amino acid sequence represented by SEQ ID NO: 18.

11. The diagnostic product according to claim 10, which is a diagnostic product for colon cancer.

12. A diagnostic method, which comprises measunng an expression level of a G protein coupled receptor protein having the amino acid sequence of SEQ ID NO: 3, or its salt by using a polynucleotide according to claim 3 said method comprising quantifying mRNA encoding for said proteins using said polynucleotide.

13. The diagnostic method according to claim 12, which is a diagnostic method for colon cancer.

14. A method of determining a ligand to a G protein-coupled receptor protein with the amino acid sequence of SEQ ID NO: 3, or a salt thereof, which comprises using the G protein-coupled receptor protein or salts thereof in an assay comprising combining a test ligand with said protein, and determining the amount of binding of said test ligand to said protein.

15. A method of screening a compound that alters the binding property between a ligand and the G protein-coupled receptor protein with the amino acid sequence of SEQ ID NO: 3, or a salt thereof, in a screening assay which comprises i) contacting the G protein-coupled receptor protein or salt thereof with a ligand; ii) contacting the G protein-coupled receptor protein or salt thereof with a ligand and a test compound; iii) determining the amount of ligand bound in i) and ii); iv) comparing the values obtained.

16. A kit for screening a compound that alters the binding property between a ligand and the G protein-coupled receptor protein with the amino acid sequence of SEQ ID NO: 3, or a salt thereof, which comprises the G protein-coupled receptor protein, or salts thereof in an assay.

17. A diagnostic product, which comprises combining a polynucleotide containing a polynucleotide containing a base sequence represented by SEQ ID NO: 2 and a polynucleotide containing a base sequence represented by SEQ ID NO: 4.

18. The diagnostic product according to claim 17, which is a diagnostic product for colon cancer.

19. A diagnostic method for colon cancer which comprises measuring an expression level of an isolated G protein coupled receptor protein having the amino acid sequence of SEQ ID NO: 3 or its salt, by using a polynucleotide containing a polynucleotide containing a base sequence represented by SEQ ID NO: 2, and a polynucleotide containing a polynucleotide containing a base sequence represented by SEQ ID NO: 4 said method comprising quantifying mRNA encoding for said isolated protein using said polynucleotides.

20. The diagnostic method according to claim 19, which is used for diagnosing colon cancer.

* * * * *

```
                         SEQUENCE LISTING

<160> NUMBER OF SEQ ID NOS: 72

<210> SEQ ID NO 1
<211> LENGTH: 371
<212> TYPE: PRT
<213> ORGANISM: Human

<400> SEQUENCE: 1

Met Pro Ala Asn Phe Thr Glu Gly Ser Phe Asp Ser Ser Gly Thr Gly
                5                   10                  15

Gln Thr Leu Asp Ser Ser Pro Val Ala Cys Thr Glu Thr Val Thr Phe
            20                  25                  30

Thr Glu Val Val Glu Gly Lys Glu Trp Gly Ser Phe Tyr Tyr Ser Phe
        35                  40                  45

Lys Thr Glu Gln Leu Ile Thr Leu Trp Val Leu Phe Val Phe Thr Ile
    50                  55                  60

Val Gly Asn Ser Val Val Leu Phe Ser Thr Trp Arg Arg Lys Lys Lys
65                  70                  75                  80

Ser Arg Met Thr Phe Phe Val Thr Gln Leu Ala Ile Thr Asp Ser Phe
                85                  90                  95

Thr Gly Leu Val Asn Ile Leu Thr Asp Ile Asn Trp Arg Phe Thr Gly
            100                 105                 110

Asp Phe Thr Ala Pro Asp Leu Val Cys Arg Val Val Arg Tyr Leu Gln
        115                 120                 125

Val Val Leu Leu Tyr Ala Ser Thr Tyr Val Leu Val Ser Leu Ser Ile
    130                 135                 140

Asp Arg Tyr His Ala Ile Val Tyr Pro Met Lys Phe Leu Gln Gly Glu
145                 150                 155                 160

Lys Gln Ala Arg Val Leu Ile Val Ile Ala Trp Ser Leu Ser Phe Leu
                165                 170                 175

Phe Ser Ile Pro Thr Leu Ile Ile Phe Gly Lys Arg Thr Leu Ser Asn
            180                 185                 190

Gly Glu Val Gln Cys Trp Ala Leu Trp Pro Asp Asp Ser Tyr Trp Thr
        195                 200                 205

Pro Tyr Met Thr Ile Val Ala Phe Leu Val Tyr Phe Ile Pro Leu Thr
    210                 215                 220

Ile Ile Ser Ile Met Tyr Gly Ile Val Ile Arg Thr Ile Trp Ile Lys
225                 230                 235                 240

Ser Lys Thr Tyr Glu Thr Val Ile Ser Asn Cys Ser Asp Gly Lys Leu
```

```
                245                 250                 255

Cys Ser Ser Tyr Asn Arg Gly Leu Ile Ser Lys Ala Lys Ile Lys Ala
            260                 265                 270

Ile Lys Tyr Ser Ile Ile Ile Ile Leu Ala Phe Ile Cys Cys Trp Ser
        275                 280                 285

Pro Tyr Phe Leu Phe Asp Ile Leu Asp Asn Phe Asn Leu Leu Pro Asp
    290                 295                 300

Thr Gln Glu Arg Phe Tyr Ala Ser Val Ile Ile Gln Asn Leu Pro Ala
305                 310                 315                 320

Leu Asn Ser Ala Ile Asn Pro Leu Ile Tyr Cys Val Phe Ser Ser Ser
                325                 330                 335

Ile Ser Phe Pro Cys Arg Glu Gln Arg Ser Gln Asp Ser Arg Met Thr
            340                 345                 350

Phe Arg Glu Arg Thr Glu Arg His Glu Met Gln Ile Leu Ser Lys Pro
        355                 360                 365

Glu Phe Ile
    370


<210> SEQ ID NO 2
<211> LENGTH: 1113
<212> TYPE: DNA
<213> ORGANISM: Human

<400> SEQUENCE: 2

atgccagcca acttcacaga gggcagcttc gattccagtg ggaccgggca gacgctggat      60

tcttccccag tggcttgcac tgaaacagtg acttttactg aagtggtgga aggaaaggaa     120

tggggttcct tctactactc ctttaagact gagcaattga taactctgtg ggtcctcttt     180

gtttttacca ttgttggaaa ctccgttgtg ctttttttcca catggaggag aaagaagaag    240

tcaagaatga ccttctttgt gactcagctg gccatcacag attctttcac aggactggtc     300

aacatcttga cagatattaa ttggcgattc actggagact tcacggcacc tgacctggtt     360

tgccgagtgg tccgctattt gcaggttgtg ctgctctacg cctctaccta cgtcctggtg     420

tccctcagca tagacagata ccatgccatc gtctacccca tgaagttcct tcaaggagaa     480

aagcaagcca gggtcctcat tgtgatcgcc tggagcctgt cttttctgtt ctccattccc     540

accctgatca tatttgggaa gaggacactg tccaacggtg aagtgcagtg ctgggccctg     600

tggcctgacg actcctactg gaccccatac atgaccatcg tggccttcct ggtgtacttc     660

atccctctga caatcatcag catcatgtat ggcattgtga tccgaactat ttggattaaa     720

agcaaaacct acgaaacagt gatttccaac tgctcagatg ggaaactgtg cagcagctat     780

aaccgaggac tcatctcaaa ggcaaaaatc aaggctatca agtatagcat catcatcatt     840

cttgccttca tctgctgttg gagtccatac ttcctgtttg acattttgga caatttcaac     900

ctccttccag acacccagga gcgtttctat gcctctgtga tcattcagaa cctgccagca     960

ttgaatagtg ccatcaaccc cctcatctac tgtgtcttca gcagctccat ctctttcccc    1020

tgcagggagc aaagatcaca ggattccaga atgacgttcc gggagagaac tgagaggcat    1080

gagatgcaga ttctgtccaa gccagaattc atc                                 1113


<210> SEQ ID NO 3
<211> LENGTH: 371
<212> TYPE: PRT
<213> ORGANISM: Human

<400> SEQUENCE: 3
```

```
Met Pro Ala Asn Phe Thr Glu Gly Ser Phe Asp Ser Ser Gly Thr Gly
                5                  10                  15

Gln Thr Leu Asp Ser Ser Pro Val Ala Cys Thr Glu Thr Val Thr Phe
            20                  25                  30

Thr Glu Val Val Glu Gly Lys Glu Trp Gly Ser Phe Tyr Tyr Ser Phe
        35                  40                  45

Lys Thr Glu Gln Leu Ile Thr Leu Trp Val Leu Phe Val Phe Thr Ile
    50                  55                  60

Val Gly Asn Ser Val Val Leu Phe Ser Thr Trp Arg Arg Lys Lys Lys
 65                  70                  75                  80

Ser Arg Met Thr Phe Phe Val Thr Gln Leu Ala Ile Thr Asp Ser Phe
                85                  90                  95

Thr Gly Leu Val Asn Ile Leu Thr Asp Ile Ile Trp Arg Phe Thr Gly
            100                 105                 110

Asp Phe Thr Ala Pro Asp Leu Val Cys Arg Val Val Arg Tyr Leu Gln
        115                 120                 125

Val Val Leu Leu Tyr Ala Ser Thr Tyr Val Leu Val Ser Leu Ser Ile
    130                 135                 140

Asp Arg Tyr His Ala Ile Val Tyr Pro Met Lys Phe Leu Gln Gly Glu
145                 150                 155                 160

Lys Gln Ala Arg Val Leu Ile Val Ile Ala Trp Ser Leu Ser Phe Leu
                165                 170                 175

Phe Ser Ile Pro Thr Leu Ile Ile Phe Gly Lys Arg Thr Leu Ser Asn
            180                 185                 190

Gly Glu Val Gln Cys Trp Ala Leu Trp Pro Asp Asp Ser Tyr Trp Thr
        195                 200                 205

Pro Tyr Met Thr Ile Val Ala Phe Leu Val Tyr Phe Ile Pro Leu Thr
    210                 215                 220

Ile Ile Ser Ile Met Tyr Gly Ile Val Ile Arg Thr Ile Trp Ile Lys
225                 230                 235                 240

Ser Lys Thr Tyr Glu Thr Val Ile Ser Asn Cys Ser Asp Gly Lys Leu
                245                 250                 255

Cys Ser Ser Tyr Asn Arg Gly Leu Ile Ser Lys Ala Lys Ile Lys Ala
            260                 265                 270

Ile Lys Tyr Ser Ile Ile Ile Ile Leu Ala Phe Ile Cys Cys Trp Ser
        275                 280                 285

Pro Tyr Phe Leu Phe Asp Ile Leu Asp Asn Phe Asn Leu Leu Pro Asp
    290                 295                 300

Thr Gln Glu Arg Phe Tyr Ala Ser Val Ile Ile Gln Asn Leu Pro Ala
305                 310                 315                 320

Leu Asn Ser Ala Ile Asn Pro Leu Ile Tyr Cys Val Phe Ser Ser Ser
                325                 330                 335

Ile Ser Phe Pro Cys Arg Glu Arg Arg Ser Gln Asp Ser Arg Met Thr
            340                 345                 350

Phe Arg Glu Arg Thr Glu Arg His Glu Met Gln Ile Leu Ser Lys Pro
        355                 360                 365

Glu Phe Ile
    370


<210> SEQ ID NO 4
<211> LENGTH: 1113
<212> TYPE: DNA
<213> ORGANISM: Human
```

<400> SEQUENCE: 4

```
atgccagcca acttcacaga gggcagcttc gattccagtg ggaccgggca gacgctggat     60
tcttccccag tggcttgcac tgaaacagtg acttttactg aagtggtgga aggaaaggaa    120
tggggttcct tctactactc ctttaagact gagcaattga taactctgtg ggtcctcttt    180
gtttttacca ttgttggaaa ctccgttgtg cttttttcca catggaggag aaagaagaag    240
tcaagaatga ccttctttgt gactcagctg gccatcacag attctttcac aggactggtc    300
aacatcttga cagatattat ttggcgattc actggagact tcacggcacc tgacctggtt    360
tgccgagtgg tccgctattt gcaggttgtg ctgctctacg cctctaccta cgtcctggtg    420
tccctcagca tagacagata ccatgccatc gtctacccca tgaagttcct tcaaggagaa    480
aagcaagcca gggtcctcat tgtgatcgcc tggagcctgt cttttctgtt ctccattccc    540
accctgatca tatttgggaa gaggacactg tccaacggtg aagtgcagtg ctgggccctg    600
tggcctgacg actcctactg gaccccatac atgaccatcg tggcctttct ggtgtacttc    660
atccctctga caatcatcag catcatgtat ggcattgtga tccgaactat ttggattaaa    720
agcaaaacct acgaaacagt gatttccaac tgctcagatg ggaaactgtg cagcagctat    780
aaccgaggac tcatctcaaa ggcaaaaatc aaggctatca agtatagcat catcatcatt    840
cttgccttca tctgctgttg gagtccatac ttcctgtttg acattttgga caatttcaac    900
ctccttccag acacccagga gcgtttctat gcctctgtga tcattcagaa cctgccagca    960
ttgaatagtg ccatcaaccc cctcatctac tgtgtcttca gcagctccat ctctttcccc   1020
tgcagggagc gaagatcaca ggattccaga atgacgttcc gggagagaac cgagaggcat   1080
gagatgcaga ttctgtccaa gccagaattc atc                                1113
```

<210> SEQ ID NO 5
<211> LENGTH: 22
<212> TYPE: DNA
<213> ORGANISM: Artificial Sequence
<220> FEATURE:
<223> OTHER INFORMATION: Designed oligonucleotide primer to amplify DNA encoding TGR23-1 or TGR23-2
<400> SEQUENCE: 5

```
atgccagcca acttcacaga gg                                               22
```

<210> SEQ ID NO 6
<211> LENGTH: 24
<212> TYPE: DNA
<213> ORGANISM: Artificial Sequence
<220> FEATURE:
<223> OTHER INFORMATION: Designed oligonucleotide primer to amplify DNA encoding TGR23-1 or TGR23-2
<400> SEQUENCE: 6

```
ctagatgaat tctggcttgg acag                                             24
```

<210> SEQ ID NO 7
<211> LENGTH: 21
<212> TYPE: DNA
<213> ORGANISM: Artificial Sequence
<220> FEATURE:
<223> OTHER INFORMATION: Designed oligonucleotide primer to amplify DNA encoding human TGR23-1 or TGR23-2

<400> SEQUENCE: 7

```
ttcactggag acttcacggc a                                                21
```

<210> SEQ ID NO 8

-continued

```
<211> LENGTH: 22
<212> TYPE: DNA
<213> ORGANISM: Artificial Sequence
<220> FEATURE:
<223> OTHER INFORMATION: Designed oligonucleotide primer to amplify DNA
      encoding human TGR23-1 or TGR23-2

<400> SEQUENCE: 8

tagaggcgta gagcagcaca ac                                            22


<210> SEQ ID NO 9
<211> LENGTH: 28
<212> TYPE: DNA
<213> ORGANISM: Artificial Sequence
<220> FEATURE:
<223> OTHER INFORMATION: Designed oligonucleotide probe (labeled with
      FAM (5') and TAMRA (3'))

<400> SEQUENCE: 9

acctggtttg ccgagtggtc cgctattt                                      28


<210> SEQ ID NO 10
<211> LENGTH: 353
<212> TYPE: PRT
<213> ORGANISM: Mouse

<400> SEQUENCE: 10

Met Pro Ala Asn Leu Thr Glu Gly Ser Phe His Ala Asn Gln Thr Val
                5                   10                  15

Pro Met Leu Asp Ser Ser Pro Val Ala Cys Thr Glu Ile Val Thr Phe
            20                  25                  30

Thr Glu Ala Leu Val Ala Glu Glu Trp Gly Ser Phe Tyr Ser Ser Phe
        35                  40                  45

Lys Thr Glu Gln Leu Ile Thr Leu Trp Val Leu Phe Val Val Thr Ile
    50                  55                  60

Val Gly Asn Ser Val Val Leu Phe Ser Thr Cys Arg Arg Lys Arg Lys
 65                  70                  75                  80

Ser Arg Met Thr Phe Phe Val Thr Gln Leu Ala Ile Thr Gly Asp Phe
                85                  90                  95

Met Ala Pro Asp Leu Val Cys Arg Val Val Arg Tyr Leu Gln Val Val
            100                 105                 110

Leu Leu Tyr Ala Ser Thr Tyr Val Leu Val Ser Leu Ser Ile Asp Arg
        115                 120                 125

Tyr His Ala Ile Val Tyr Pro Met Lys Phe Leu Gln Gly Glu Lys Gln
    130                 135                 140

Ala Lys Val Leu Ile Gly Ile Ala Trp Ser Leu Ser Phe Leu Phe Ser
145                 150                 155                 160

Ile Pro Thr Leu Ile Ile Phe Gly Lys Arg Thr Leu Ser Asn Gly Glu
                165                 170                 175

Val Gln Cys Trp Ala Leu Trp Pro Asp Asp Ser Tyr Trp Thr Pro Tyr
            180                 185                 190

Met Thr Ile Val Ala Phe Leu Val Tyr Phe Ile Pro Leu Ala Ile Ile
        195                 200                 205

Ser Val Ile Tyr Gly Leu Val Ile Arg Thr Ile Trp Met Lys Ser Lys
    210                 215                 220

Thr His Glu Thr Val Ile Ser Asn Cys Ser Asp Gly Lys Leu Cys Cys
225                 230                 235                 240

Ser Tyr Asn Arg Gly Leu Ile Ser Lys Ala Lys Ile Lys Ala Ile Lys
                245                 250                 255
```

-continued

```
Tyr Ser Ile Val Ile Ile Leu Ala Phe Ile Cys Cys Trp Ser Pro Tyr
            260                 265                 270

Phe Leu Phe Asp Ile Leu Asp Asn Phe Asn Val Leu Pro Asp Thr Lys
        275                 280                 285

Glu Arg Phe Tyr Ala Ser Val Ile Ile Gln Asn Leu Pro Ala Leu Asn
    290                 295                 300

Ser Ala Ile Asn Pro Leu Ile Tyr Cys Ile Phe Ser Ser Ser Ile Cys
305                 310                 315                 320

Ser Pro Cys Lys Met Gln Arg Ser Gln Asp Ser Arg Met Thr Tyr Arg
                325                 330                 335

Glu Arg Ser Glu Arg His Glu Met Gln Ile Leu Ser Lys Pro Glu Phe
            340                 345                 350

Ile


<210> SEQ ID NO 11
<211> LENGTH: 1059
<212> TYPE: DNA
<213> ORGANISM: Mouse

<400> SEQUENCE: 11

atgccagcca acctcacaga gggcagcttt catgccaacc agactgtgcc gatgctagat     60

tcttccccag tagcttgcac tgaaattgtg acgttcactg aagcactggt ggctgaggag    120

tggggctcct tctactcctc ctttaagaca gaacagctga taaccctgtg ggtcctgttt    180

gtcgtcacta ttgtgggaaa ctctgttgtg ctgttctcca cgtgcagaag aaaaagaaag    240

tccagaatga ccttctttgt gacacaattg gccatcacag gagacttcat ggcccctgac    300

ctggtttgca gagtcgtccg ctacttgcag gttgtcctgc tgtatgcctc tacctacgtc    360

ctggtgtccc tcagcataga cagataccat gccatcgttt accccatgaa gtttcttcaa    420

ggagagaagc aagccaaagt cctcatcgga atagcgtgga gcctctcgtt cctgttctcc    480

attcccacgc tgatcatatt tgggaaaagg acactttcca atggtgaggt gcagtgctgg    540

gcactgtggc cggatgactc ctactggacc ccgtacatga ccatcgtcgc ctttctggtg    600

tacttcattc ccttggcaat tatcagcgtt atctatggcc ttgtgatccg aactatttgg    660

atgaaaagca aaacccatga gacggtgatt tccaactgct cagatggcaa actatgctgc    720

agctacaacc gagggctcat ctctaaggca aaaatcaagg ccatcaagta tagcatcgtc    780

ataatccttg ctttcatctg ctgctggagc ccatacttcc tctttgacat attagacaac    840

ttcaacgtcc ttccagacac caaggagcgt ttctatgcct ctgtgattat ccagaacctg    900

cccgccttga acagtgccat taacccccctc atctactgca tcttcagcag ctccatctgc    960

tccccctgca agatgcaaag atcacaggat tccagaatga cataccgaga gagaagcgag   1020

agacacgaga tgcagattct ctccaagccg gaattcatc                          1059


<210> SEQ ID NO 12
<211> LENGTH: 21
<212> TYPE: DNA
<213> ORGANISM: Artificial Sequence
<220> FEATURE:
<223> OTHER INFORMATION: Designed oligonucleotide primer to amplify DNA
      encoding mouse TGR23-A

<400> SEQUENCE: 12

tgcagagaca gtgagacctg a                                               21
```

<210> SEQ ID NO 13
<211> LENGTH: 24
<212> TYPE: DNA
<213> ORGANISM: Artificial Sequence
<220> FEATURE:
<223> OTHER INFORMATION: Designed oligonucleotide primer to amplify DNA encoding mouse TGR23-A

<400> SEQUENCE: 13
aagttcagcc tagcactact gcct 24

<210> SEQ ID NO 14
<211> LENGTH: 371
<212> TYPE: PRT
<213> ORGANISM: Mouse

<400> SEQUENCE: 14

```
Met Pro Ala Asn Leu Thr Glu Gly Ser Phe His Ala Asn Gln Thr Val
                5                   10                  15

Pro Met Leu Asp Ser Ser Pro Val Ala Cys Thr Glu Ile Val Thr Phe
            20                  25                  30

Thr Glu Ala Leu Val Ala Glu Glu Trp Gly Ser Phe Tyr Ser Ser Phe
        35                  40                  45

Lys Thr Glu Gln Leu Ile Thr Leu Trp Val Leu Phe Val Val Thr Ile
    50                  55                  60

Val Gly Asn Ser Val Val Leu Phe Ser Thr Cys Arg Arg Lys Arg Lys
 65                 70                  75                  80

Ser Arg Met Thr Phe Phe Val Thr Gln Leu Ala Ile Thr Asp Ser Phe
                85                  90                  95

Thr Gly Leu Ile Asn Ile Leu Thr Asp Ile Ile Trp Arg Phe Thr Gly
            100                 105                 110

Asp Phe Met Ala Pro Asp Leu Val Cys Arg Val Val Arg Tyr Leu Gln
        115                 120                 125

Val Val Leu Leu Tyr Ala Ser Thr Tyr Val Leu Val Ser Leu Ser Ile
    130                 135                 140

Asp Arg Tyr His Ala Ile Val Tyr Pro Met Lys Phe Leu Gln Gly Glu
145                 150                 155                 160

Lys Gln Ala Lys Val Leu Ile Gly Ile Ala Trp Ser Leu Ser Phe Leu
                165                 170                 175

Phe Ser Ile Pro Thr Leu Ile Ile Phe Gly Lys Arg Thr Leu Ser Asn
            180                 185                 190

Gly Glu Val Gln Cys Trp Ala Leu Trp Pro Asp Asp Ser Tyr Trp Thr
        195                 200                 205

Pro Tyr Met Thr Ile Val Ala Phe Leu Val Tyr Phe Ile Pro Leu Ala
    210                 215                 220

Ile Ile Ser Val Ile Tyr Gly Leu Val Ile Arg Thr Ile Trp Met Lys
225                 230                 235                 240

Ser Lys Thr His Glu Thr Val Ile Ser Asn Cys Ser Asp Gly Lys Leu
                245                 250                 255

Cys Cys Ser Tyr Asn Arg Gly Leu Ile Ser Lys Ala Lys Ile Lys Ala
            260                 265                 270

Ile Lys Tyr Ser Ile Val Ile Ile Leu Ala Phe Ile Cys Cys Trp Ser
        275                 280                 285

Pro Tyr Phe Leu Phe Asp Ile Leu Asp Asn Phe Asn Val Leu Pro Asp
    290                 295                 300

Thr Lys Glu Arg Phe Tyr Ala Ser Val Ile Ile Gln Asn Leu Pro Ala
305                 310                 315                 320
```

```
Leu Asn Ser Ala Ile Asn Pro Leu Ile Tyr Cys Ile Phe Ser Ser Ser
                325                 330                 335

Ile Cys Ser Pro Cys Lys Met Gln Arg Ser Gln Asp Ser Arg Met Thr
            340                 345                 350

Tyr Arg Glu Arg Ser Glu Arg His Glu Met Gln Ile Leu Ser Lys Pro
        355                 360                 365

Glu Phe Ile
    370


<210> SEQ ID NO 15
<211> LENGTH: 1113
<212> TYPE: DNA
<213> ORGANISM: Mouse

<400> SEQUENCE: 15

atgccagcca acctcacaga gggcagcttt catgccaacc agactgtgcc gatgctagat     60

tcttccccag tagcttgcac tgaaattgtg acgttcactg aagcactggt ggctgaggag    120

tggggctcct tctactcctc ctttaagaca gaacagctga taaccctgtg ggtcctgttt    180

gtcgtcacta ttgtgggaaa ctctgttgtg ctgttctcca cgtgcagaag aaaaagaaag    240

tccagaatga ccttctttgt gacacaattg gccatcacag actccttcac gggcctgatc    300

aacatcttga cagacattat ttggcgattc acaggagact tcatggcccc tgacctggtt    360

tgcagagtcg tccgctactt gcaggttgtc ctgctgtatg cctctaccta cgtcctggtg    420

tccctcagca tagacagata ccatgccatc gtttacccca tgaagtttct tcaaggagag    480

aagcaagcca aagtcctcat cggaatagcg tggagcctct cgttcctgtt ctccattccc    540

acgctgatca tatttgggaa aaggacactt tccaatggtg aggtgcagtg ctgggcactg    600

tggccggatg actcctactg gaccccgtac atgaccatcg tcgcctttct ggtgtacttc    660

attcccttgg caattatcag cgttatctat ggccttgtga tccgaactat ttggatgaaa    720

agcaaaaccc atgagacggt gatttccaac tgctcagatg gcaaactatg ctgcagctac    780

aaccgagggc tcatctctaa ggcaaaaatc aaggccatca agtatagcat cgtcataatc    840

cttgctttca tctgctgctg gagcccatac ttcctctttg acatattaga caacttcaac    900

gtccttccag acaccaagga gcgtttctat gcctctgtga ttatccagaa cctgcccgcc    960

ttgaacagtg ccattaaccc cctcatctac tgcatcttca gcagctccat ctgctccccc   1020

tgcaagatgc aaagatcaca ggattccaga atgacatacc gagagagaag cgagagacac   1080

gagatgcaga ttctctccaa gccggaattc atc                                1113


<210> SEQ ID NO 16
<211> LENGTH: 371
<212> TYPE: PRT
<213> ORGANISM: Human
<220> FEATURE:
<221> NAME/KEY:
<222> LOCATION: (273)
<223> OTHER INFORMATION: Xaa represents Val or Ile
<220> FEATURE:
<221> NAME/KEY:
<222> LOCATION: (308)
<223> OTHER INFORMATION: Xaa represents Arg or His

<400> SEQUENCE: 16

Met Pro Ala Asn Phe Thr Glu Gly Ser Phe Asp Ser Ser Gly Thr Gly
                5                   10                  15

Gln Thr Leu Asp Ser Ser Pro Val Ala Cys Thr Glu Thr Val Thr Phe
```

-continued

```
            20                  25                  30

Thr Glu Val Val Glu Gly Lys Glu Trp Gly Ser Phe Tyr Tyr Ser Phe
        35                  40                  45

Lys Thr Glu Gln Leu Ile Thr Leu Trp Val Leu Phe Val Phe Thr Ile
    50                  55                  60

Val Gly Asn Ser Val Val Leu Phe Ser Thr Trp Arg Arg Lys Lys Lys
65                  70                  75                  80

Ser Arg Met Thr Phe Phe Val Thr Gln Leu Ala Ile Thr Asp Ser Phe
                85                  90                  95

Thr Gly Leu Val Asn Ile Leu Thr Asp Ile Asn Trp Arg Phe Thr Gly
            100                 105                 110

Asp Phe Thr Ala Pro Asp Leu Val Cys Arg Val Val Arg Tyr Leu Gln
        115                 120                 125

Val Val Leu Leu Tyr Ala Ser Thr Tyr Val Leu Val Ser Leu Ser Ile
    130                 135                 140

Asp Arg Tyr His Ala Ile Val Tyr Pro Met Lys Phe Leu Gln Gly Glu
145                 150                 155                 160

Lys Gln Ala Arg Val Leu Ile Val Ile Ala Trp Ser Leu Ser Phe Leu
                165                 170                 175

Phe Ser Ile Pro Thr Leu Ile Ile Phe Gly Lys Arg Thr Leu Ser Asn
            180                 185                 190

Gly Glu Val Gln Cys Trp Ala Leu Trp Pro Asp Asp Ser Tyr Trp Thr
        195                 200                 205

Pro Tyr Met Thr Ile Val Ala Phe Leu Val Tyr Phe Ile Pro Leu Thr
    210                 215                 220

Ile Ile Ser Ile Met Tyr Gly Ile Val Ile Arg Thr Ile Trp Ile Lys
225                 230                 235                 240

Ser Lys Thr Tyr Glu Thr Val Ile Ser Asn Cys Ser Asp Gly Lys Leu
                245                 250                 255

Cys Ser Ser Tyr Asn Arg Gly Leu Ile Ser Lys Ala Lys Ile Lys Ala
            260                 265                 270

Xaa Lys Tyr Ser Ile Ile Ile Ile Leu Ala Phe Ile Cys Cys Trp Ser
        275                 280                 285

Pro Tyr Phe Leu Phe Asp Ile Leu Asp Asn Phe Asn Leu Leu Pro Asp
    290                 295                 300

Thr Gln Glu Xaa Phe Tyr Ala Ser Val Ile Ile Gln Asn Leu Pro Ala
305                 310                 315                 320

Leu Asn Ser Ala Ile Asn Pro Leu Ile Tyr Cys Val Phe Ser Ser Ser
                325                 330                 335

Ile Ser Phe Pro Cys Arg Glu Arg Arg Ser Gln Asp Ser Arg Met Thr
            340                 345                 350

Phe Arg Glu Arg Thr Glu Arg His Glu Met Gln Ile Leu Ser Lys Pro
        355                 360                 365

Glu Phe Ile
    370


<210> SEQ ID NO 17
<211> LENGTH: 1113
<212> TYPE: DNA
<213> ORGANISM: Human
<220> FEATURE:
<221> NAME/KEY:
<222> LOCATION: (817)
<223> OTHER INFORMATION: r represents a or g
<220> FEATURE:
<221> NAME/KEY:
```

<222> LOCATION: (923)
<223> OTHER INFORMATION: r represents a or g

<400> SEQUENCE: 17

```
atgccagcca acttcacaga gggcagcttc gattccagtg ggaccgggca gacgctggat     60
tcttccccag tggcttgcac tgaaacagtg acttttactg aagtggtgga aggaaaggaa    120
tggggttcct tctactactc ctttaagact gagcaattga taactctgtg ggtcctcttt    180
gtttttacca ttgttggaaa ctccgttgtg ctttttttcca catggaggag aaagaagaag    240
tcaagaatga ccttctttgt gactcagctg gccatcacag attctttcac aggactggtc    300
aacatcttga cagatattaa ttggcgattc actggagact tcacggcacc tgacctggtt    360
tgccgagtgg tccgctattt gcaggttgtg ctgctctacg cctctaccta cgtcctggtg    420
tccctcagca tagacagata ccatgccatc gtctacccca tgaagttcct tcaaggagaa    480
aagcaagcca gggtcctcat tgtgatcgcc tggagcctgt cttttctgtt ctccattccc    540
accctgatca tatttgggaa gaggacactg tccaacggtg aagtgcagtg ctgggccctg    600
tggcctgacg actcctactg gaccccatac atgaccatcg tggccttcct ggtgtacttc    660
atccctctga caatcatcag catcatgtat ggcattgtga tccgaactat ttggattaaa    720
agcaaaacct acgaaacagt gatttccaac tgctcagatg ggaaactgtg cagcagctat    780
aaccgaggac tcatctcaaa ggcaaaaatc aaggctrtca agtatagcat catcatcatt    840
cttgccttca tctgctgttg gagtccatac ttcctgtttg acattttgga caatttcaac    900
ctccttccag acacccagga gcrtttctat gcctctgtga tcattcagaa cctgccagca    960
ttgaatagtg ccatcaaccc cctcatctac tgtgtcttca gcagctccat ctctttcccc   1020
tgcagggagc gaagatcaca ggattccaga atgacgttcc gggagagaac cgagaggcat   1080
gagatgcaga ttctgtccaa gccagaattc atc                                1113
```

<210> SEQ ID NO 18
<211> LENGTH: 371
<212> TYPE: PRT
<213> ORGANISM: Human

<400> SEQUENCE: 18

```
Met Pro Ala Asn Phe Thr Glu Gly Ser Phe Asp Ser Ser Gly Thr Gly
                5                   10                  15

Gln Thr Leu Asp Ser Ser Pro Val Ala Cys Thr Glu Thr Val Thr Phe
            20                  25                  30

Thr Glu Val Val Glu Gly Lys Glu Trp Gly Ser Phe Tyr Tyr Ser Phe
        35                  40                  45

Lys Thr Glu Gln Leu Ile Thr Leu Trp Val Leu Phe Val Phe Thr Ile
    50                  55                  60

Val Gly Asn Ser Val Val Leu Phe Ser Thr Trp Arg Arg Lys Lys Lys
65                  70                  75                  80

Ser Arg Met Thr Phe Phe Val Thr Gln Leu Ala Ile Thr Asp Ser Phe
                85                  90                  95

Thr Gly Leu Val Asn Ile Leu Thr Asp Ile Ile Trp Arg Phe Thr Gly
            100                 105                 110

Asp Phe Thr Ala Pro Asp Leu Val Cys Arg Val Val Arg Tyr Leu Gln
        115                 120                 125

Val Val Leu Leu Tyr Ala Ser Thr Tyr Val Leu Val Ser Leu Ser Ile
    130                 135                 140

Asp Arg Tyr His Ala Ile Val Tyr Pro Met Lys Phe Leu Gln Gly Glu
```

-continued

```
145                 150                 155                 160

Lys Gln Ala Arg Val Leu Ile Val Ile Ala Trp Ser Leu Ser Phe Leu
                165                 170                 175

Phe Ser Ile Pro Thr Leu Ile Ile Phe Gly Lys Arg Thr Leu Ser Asn
            180                 185                 190

Gly Glu Val Gln Cys Trp Ala Leu Trp Pro Gly Asp Ser Tyr Trp Thr
        195                 200                 205

Pro Tyr Met Thr Ile Val Ala Phe Leu Val Tyr Phe Ile Pro Leu Thr
    210                 215                 220

Ile Ile Ser Ile Met Tyr Gly Ile Val Ile Arg Thr Ile Trp Ile Lys
225                 230                 235                 240

Ser Lys Thr Tyr Glu Thr Val Ile Ser Asn Cys Ser Asp Gly Lys Leu
                245                 250                 255

Cys Ser Ser Tyr Asn Arg Gly Leu Ile Ser Lys Ala Lys Ile Lys Ala
            260                 265                 270

Ile Lys Tyr Ser Ile Ile Ile Ile Leu Ala Phe Ile Cys Cys Trp Ser
        275                 280                 285

Pro Tyr Phe Leu Phe Asp Ile Leu Asp Asn Phe Asn Leu Leu Pro Asp
    290                 295                 300

Thr Gln Glu Arg Phe Tyr Ala Ser Val Ile Ile Gln Asn Leu Pro Ala
305                 310                 315                 320

Leu Asn Ser Ala Ile Asn Pro Pro Ile Tyr Cys Val Phe Ser Ser Ser
                325                 330                 335

Ile Ser Phe Pro Cys Arg Glu Gln Arg Ser Gln Asp Ser Arg Met Thr
            340                 345                 350

Phe Arg Glu Arg Thr Glu Arg His Glu Met Gln Ile Leu Ser Lys Pro
        355                 360                 365

Glu Phe Ile
    370
```

<210> SEQ ID NO 19
<211> LENGTH: 1113
<212> TYPE: DNA
<213> ORGANISM: Human

<400> SEQUENCE: 19

```
atgccagcca acttcacaga gggcagcttc gattccagtg ggaccgggca gacgctggat     60

tcttccccag tggcttgcac tgaaacagtg acttttactg aagtggtgga aggaaaggaa    120

tggggttcct tctactactc ctttaagact gagcaattga taactctgtg ggtcctcttt    180

gtttttacca ttgttggaaa ctccgttgtg cttttttcca catggaggag aaagaagaag    240

tcaagaatga ccttctttgt gactcagctg gccatcacag attctttcac aggactggtc    300

aacatcttga cagatattat ttggcgattc actggagact tcacggcacc tgacctggtt    360

tgccgagtgg tccgctattt gcaggttgtg ctgctctacg cctctaccta cgtcctggtg    420

tccctcagca tagacagata ccatgccatc gtctacccca tgaagttcct tcaaggagaa    480

aagcaagcca gggtcctcat tgtgatcgcc tggagcctgt cttttctgtt ctccattccc    540

accctgatca tatttgggaa gaggacactg tccaacggtg aagtgcagtg ctgggccctg    600

tggcctggcg actcctactg gaccccatac atgaccatcg tggccttcct ggtgtacttc    660

atccctctga caatcatcag catcatgtat ggcattgtga tccgaactat ttggattaaa    720

agcaaaacct acgaaacagt gatttccaac tgctcagatg ggaaactgtg cagcagctat    780

aaccgaggac tcatctcaaa ggcaaaaatc aaggctatca agtatagcat tatcatcatt    840
```

-continued cttgccttca tctgctgttg gagtccatac ttcctgtttg acattttgga caatttcaac 900
ctccttccag acacccagga gcgtttctat gcctctgtga tcattcagaa cctgccagca 960
ttgaatagtg ccatcaaccc ccccatctac tgtgtcttca gcagctccat ctctttcccc 1020
tgcagggagc aaagatcaca ggattccaga atgacgttcc gggagagaac tgagaggcat 1080
gagatgcaga ttctgtccaa gccagaattc atc 1113

<210> SEQ ID NO 20
<211> LENGTH: 27
<212> TYPE: DNA
<213> ORGANISM: Artificial Sequence
<220> FEATURE:
<223> OTHER INFORMATION: Primer

<400> SEQUENCE: 20
tatagtcgac atgccagcca acttcac 27

<210> SEQ ID NO 21
<211> LENGTH: 28
<212> TYPE: DNA
<213> ORGANISM: Artificial Sequence
<220> FEATURE:
<223> OTHER INFORMATION: Primer

<400> SEQUENCE: 21
tgtcactagt ctagatgaat tctggctt 28

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
ttcactggag acttcacggc a 21

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
tagaggcgta gagcagcaca ac 22

<210> SEQ ID NO 24
<211> LENGTH: 28
<212> TYPE: DNA
<213> ORGANISM: Artificial Sequence
<220> FEATURE:
<223> OTHER INFORMATION: Probe

<400> SEQUENCE: 24
acctggtttg ccgagtggtc cgctattt 28

<210> SEQ ID NO 25
<211> LENGTH: 18
<212> TYPE: PRT
<213> ORGANISM: Rat

<400> SEQUENCE: 25

Ser Phe Arg Asn Gly Val Gly Ser Gly Val Lys Lys Thr Ser Phe Arg
5 10 15

Arg Ala
18

<210> SEQ ID NO 26
<211> LENGTH: 15
<212> TYPE: PRT
<213> ORGANISM: Rat

<400> SEQUENCE: 26

Ser Phe Arg Asn Gly Val Gly Ser Gly Val Lys Lys Thr Ser Phe
5 10 15

<210> SEQ ID NO 27
<211> LENGTH: 14
<212> TYPE: PRT
<213> ORGANISM: Rat

<400> SEQUENCE: 27

Ser Phe Arg Asn Gly Val Gly Ser Gly Val Lys Lys Thr Ser
5 10 14

<210> SEQ ID NO 28
<211> LENGTH: 24
<212> TYPE: DNA
<213> ORGANISM: Artificial Sequence
<220> FEATURE:
<223> OTHER INFORMATION: Primer

<400> SEQUENCE: 28
cagattttgg gaagtccaaa atga 24

<210> SEQ ID NO 29
<211> LENGTH: 24
<212> TYPE: DNA
<213> ORGANISM: Artificial Sequence
<220> FEATURE:
<223> OTHER INFORMATION: Primer

<400> SEQUENCE: 29
gagtacgtca gtcacactct acag 24

<210> SEQ ID NO 30
<211> LENGTH: 24
<212> TYPE: DNA
<213> ORGANISM: Artificial Sequence
<220> FEATURE:
<223> OTHER INFORMATION: Primer

<400> SEQUENCE: 30
agattaattc cccgagtcct ttgc 24

<210> SEQ ID NO 31
<211> LENGTH: 322
<212> TYPE: DNA
<213> ORGANISM: Human

<400> SEQUENCE: 31
cagattttgg gaagtccaaa atgattagct cagtaaaact caatctcatc ctagttctgt 60
cgctgtccac aatgcatgtg ttttggtgtt atccagttcc atcttctaag gtgtctggaa 120
aatctgatta ctttctcatt ctgctgaaca gctgcccaac cagattggac aggagcaaag 180
aactagcttt tctaaagcca attttggaga agatgtttgt gaaaaggtcc tttcgcaatg 240
gagttggcac agggatgaaa aaaacttcct ttcaaagagc aaaatcatga ctaagtgtgc 300
aaaggactcg gggaattaat ct 322

<210> SEQ ID NO 32
<211> LENGTH: 89
<212> TYPE: PRT
<213> ORGANISM: Human

<400> SEQUENCE: 32

Met Ile Ser Ser Val Lys Leu Asn Leu Ile Leu Val Leu Ser Leu Ser
5 10 15

Thr Met His Val Phe Trp Cys Tyr Pro Val Pro Ser Ser Lys Val Ser
20 25 30

Gly Lys Ser Asp Tyr Phe Leu Ile Leu Leu Asn Ser Cys Pro Thr Arg
35 40 45

Leu Asp Arg Ser Lys Glu Leu Ala Phe Leu Lys Pro Ile Leu Glu Lys
50 55 60

Met Phe Val Lys Arg Ser Phe Arg Asn Gly Val Gly Thr Gly Met Lys
65 70 75 80

Lys Thr Ser Phe Gln Arg Ala Lys Ser
85

<210> SEQ ID NO 33
<211> LENGTH: 18
<212> TYPE: PRT
<213> ORGANISM: Human

<400> SEQUENCE: 33

Ser Phe Arg Asn Gly Val Gly Thr Gly Met Lys Lys Thr Ser Phe Gln
5 10 15

Arg Ala
18

<210> SEQ ID NO 34
<211> LENGTH: 15
<212> TYPE: PRT
<213> ORGANISM: Human

<400> SEQUENCE: 34

Ser Phe Arg Asn Gly Val Gly Thr Gly Met Lys Lys Thr Ser Phe
5 10 15

<210> SEQ ID NO 35
<211> LENGTH: 14
<212> TYPE: PRT
<213> ORGANISM: Human

<400> SEQUENCE: 35

Ser Phe Arg Asn Gly Val Gly Thr Gly Met Lys Lys Thr Ser
5 10 14

<210> SEQ ID NO 36
<211> LENGTH: 20
<212> TYPE: PRT
<213> ORGANISM: Human

<400> SEQUENCE: 36

Ser Phe Arg Asn Gly Val Gly Thr Gly Met Lys Lys Thr Ser Phe Gln
5 10 15
Arg Ala Lys Ser
20

<210> SEQ ID NO 37
<211> LENGTH: 24
<212> TYPE: DNA
<213> ORGANISM: Artificial Sequence
<220> FEATURE:
<223> OTHER INFORMATION: Primer

<400> SEQUENCE: 37
ccagtcacac aggagggatc tcaa 24

<210> SEQ ID NO 38
<211> LENGTH: 24
<212> TYPE: DNA
<213> ORGANISM: Artificial Sequence
<220> FEATURE:
<223> OTHER INFORMATION: Primer

<400> SEQUENCE: 38
gcacatcagt cacactctac atag 24

<210> SEQ ID NO 39
<211> LENGTH: 24
<212> TYPE: DNA
<213> ORGANISM: Artificial Sequence
<220> FEATURE:
<223> OTHER INFORMATION: Primer

<400> SEQUENCE: 39
agattaattc ccagagtcct ttgc 24

<210> SEQ ID NO 40
<211> LENGTH: 443
<212> TYPE: DNA
<213> ORGANISM: Mouse

<400> SEQUENCE: 40
ccagtcacac aggagggatc tcaatgacat ttttacttct gaacttttct aatataaaag 60
ggccacccaa gcaggctcag acagcaaacg tgaggaaatt ggcaataaaa acccatctgc 120
gcaggtctcg gaaaatccaa aatgattggc tcgttaaaac tcagcttcgt cttagctctg 180
tcgctgtctg taatgcacgt gctttggtgt tatccggtcc tctcttccaa ggtgcctggg 240
aagcctgatt actttctcat cttgctgagc agctgcccag ccaggctgga ggggagcgac 300
aggctagctt ttctaaagcc aattttggag aagacatcga tgaaaaggtc ctttcgcaac 360
ggagtcggct caggggcgaa aaaaacttcg tttcgaagag caaagcaatg aataagtgtg 420
caaaggactc tgggaattaa tct 443

<210> SEQ ID NO 41
<211> LENGTH: 89
<212> TYPE: PRT
<213> ORGANISM: Mouse

<400> SEQUENCE: 41

Met Ile Gly Ser Leu Lys Leu Ser Phe Val Leu Ala Leu Ser Leu Ser
5 10 15

Val Met His Val Leu Trp Cys Tyr Pro Val Leu Ser Ser Lys Val Pro
20 25 30

Gly Lys Pro Asp Tyr Phe Leu Ile Leu Leu Ser Ser Cys Pro Ala Arg
35 40 45

Leu Glu Gly Ser Asp Arg Leu Ala Phe Leu Lys Pro Ile Leu Glu Lys

-continued

```
     50                  55                  60

Thr Ser Met Lys Arg Ser Phe Arg Asn Gly Val Gly Ser Gly Ala Lys
 65                 70                  75                  80

Lys Thr Ser Phe Arg Arg Ala Lys Gln
                 85


<210> SEQ ID NO 42
<211> LENGTH: 18
<212> TYPE: PRT
<213> ORGANISM: Mouse

<400> SEQUENCE: 42

Ser Phe Arg Asn Gly Val Gly Ser Gly Ala Lys Lys Thr Ser Phe Arg
                  5                  10                  15

Arg Ala
     18


<210> SEQ ID NO 43
<211> LENGTH: 15
<212> TYPE: PRT
<213> ORGANISM: Mouse

<400> SEQUENCE: 43

Ser Phe Arg Asn Gly Val Gly Ser Gly Ala Lys Lys Thr Ser Phe
                  5                  10                  15


<210> SEQ ID NO 44
<211> LENGTH: 14
<212> TYPE: PRT
<213> ORGANISM: Mouse

<400> SEQUENCE: 44

Ser Phe Arg Asn Gly Val Gly Ser Gly Ala Lys Lys Thr Ser
                  5                  10              14


<210> SEQ ID NO 45
<211> LENGTH: 20
<212> TYPE: PRT
<213> ORGANISM: Mouse

<400> SEQUENCE: 45

Ser Phe Arg Asn Gly Val Gly Ser Gly Ala Lys Lys Thr Ser Phe Arg
                  5                  10                  15

Arg Ala Lys Gln
             20


<210> SEQ ID NO 46
<211> LENGTH: 24
<212> TYPE: DNA
<213> ORGANISM: Artificial Sequence
<220> FEATURE:
<223> OTHER INFORMATION: Primer

<400> SEQUENCE: 46

ctgattactt tctcatyytg ctga                                             24


<210> SEQ ID NO 47
<211> LENGTH: 199
<212> TYPE: DNA
<213> ORGANISM: Rat

<400> SEQUENCE: 47

ctgattactt tctcattttg ctgagtacct gcccagccag gctggagggg agcgacgggc     60
```

```
tagcttttct aaagccaatt ttggagaaga cgtcgatgaa aaggtccttt cgcaacggag    120

tcggctcagg ggtgaaaaaa acttcatttc gaagagcaaa gcaatgaata agtgtgcaaa    180

ggactctggg aattaatct                                                 199


<210> SEQ ID NO 48
<211> LENGTH: 54
<212> TYPE: PRT
<213> ORGANISM: Rat

<400> SEQUENCE: 48

Asp Tyr Phe Leu Ile Leu Leu Ser Thr Cys Pro Ala Arg Leu Glu Gly
                5                   10                  15

Ser Asp Gly Leu Ala Phe Leu Lys Pro Ile Leu Glu Lys Thr Ser Met
            20                  25                  30

Lys Arg Ser Phe Arg Asn Gly Val Gly Ser Gly Val Lys Lys Thr Ser
        35                  40                  45

Phe Arg Arg Ala Lys Gln
    50


<210> SEQ ID NO 49
<211> LENGTH: 20
<212> TYPE: PRT
<213> ORGANISM: Mouse

<400> SEQUENCE: 49

Ser Phe Arg Asn Gly Val Gly Ser Gly Val Lys Lys Thr Ser Phe Arg
                5                   10                  15

Arg Ala Lys Gln
            20


<210> SEQ ID NO 50
<211> LENGTH: 54
<212> TYPE: DNA
<213> ORGANISM: Rat

<400> SEQUENCE: 50

tcctttcgca acggagtcgg ctcaggggtg aaaaaaactt catttcgaag agca           54


<210> SEQ ID NO 51
<211> LENGTH: 45
<212> TYPE: DNA
<213> ORGANISM: Rat

<400> SEQUENCE: 51

tcctttcgca acggagtcgg ctcaggggtg aaaaaaactt cattt                     45


<210> SEQ ID NO 52
<211> LENGTH: 42
<212> TYPE: DNA
<213> ORGANISM: Rat

<400> SEQUENCE: 52

tcctttcgca acggagtcgg ctcaggggtg aaaaaaactt ca                        42


<210> SEQ ID NO 53
<211> LENGTH: 60
<212> TYPE: DNA
<213> ORGANISM: Rat

<400> SEQUENCE: 53
```

-continued tcctttcgca acggagtcgg ctcaggggtg aaaaaaactt catttcgaag agcaaagcaa 60

<210> SEQ ID NO 54
<211> LENGTH: 54
<212> TYPE: DNA
<213> ORGANISM: Human

<400> SEQUENCE: 54
tcctttcgca atggagttgg cacagggatg aaaaaaactt cctttcaaag agca 54

<210> SEQ ID NO 55
<211> LENGTH: 45
<212> TYPE: DNA
<213> ORGANISM: Human

<400> SEQUENCE: 55
tcctttcgca atggagttgg cacagggatg aaaaaaactt ccttt 45

<210> SEQ ID NO 56
<211> LENGTH: 42
<212> TYPE: DNA
<213> ORGANISM: Human

<400> SEQUENCE: 56
tcctttcgca atggagttgg cacagggatg aaaaaaactt cc 42

<210> SEQ ID NO 57
<211> LENGTH: 60
<212> TYPE: DNA
<213> ORGANISM: Human

<400> SEQUENCE: 57
tcctttcgca atggagttgg cacagggatg aaaaaaactt cctttcaaag agcaaaatca 60

<210> SEQ ID NO 58
<211> LENGTH: 54
<212> TYPE: DNA
<213> ORGANISM: Mouse

<400> SEQUENCE: 58
tcctttcgca acggagtcgg ctcaggggcg aaaaaaactt cgtttcgaag agca 54

<210> SEQ ID NO 59
<211> LENGTH: 45
<212> TYPE: DNA
<213> ORGANISM: Mouse

<400> SEQUENCE: 59
tcctttcgca acggagtcgg ctcaggggcg aaaaaaactt cgttt 45

<210> SEQ ID NO 60
<211> LENGTH: 42
<212> TYPE: DNA
<213> ORGANISM: Mouse

<400> SEQUENCE: 60
tcctttcgca acggagtcgg ctcaggggcg aaaaaaactt cg 42

<210> SEQ ID NO 61
<211> LENGTH: 60
<212> TYPE: DNA
<213> ORGANISM: Mouse

<400> SEQUENCE: 61

```
tcctttcgca acggagtcgg ctcaggggcg aaaaaaactt cgtttcgaag agcaaagcaa     60


<210> SEQ ID NO 62
<211> LENGTH: 16
<212> TYPE: PRT
<213> ORGANISM: Human

<400> SEQUENCE: 62

Ser Phe Arg Asn Gly Val Gly Thr Gly Met Lys Lys Thr Ser Phe Gln
                  5                  10                  15


<210> SEQ ID NO 63
<211> LENGTH: 48
<212> TYPE: DNA
<213> ORGANISM: Human

<400> SEQUENCE: 63

tcctttcgca atggagttgg cacagggatg aaaaaaactt cctttcaa                  48


<210> SEQ ID NO 64
<211> LENGTH: 371
<212> TYPE: PRT
<213> ORGANISM: Rat

<400> SEQUENCE: 64

Met Pro Ala Asn Leu Thr Glu Gly Ser Phe His Ala Asn Gln Thr Val
                 5                  10                  15

Pro Met Leu Asp Ser Ser Pro Val Ala Cys Thr Glu Ile Val Thr Phe
            20                  25                  30

Thr Glu Ala Leu Glu Ala Glu Glu Trp Gly Ser Phe Tyr Ser Ser Phe
        35                  40                  45

Lys Thr Glu Gln Leu Ile Thr Leu Trp Val Leu Phe Val Phe Thr Ile
     50                  55                  60

Val Gly Asn Ser Val Val Leu Phe Ser Thr Trp Arg Arg Lys Arg Lys
 65                  70                  75                  80

Ser Arg Met Thr Phe Phe Val Thr Gln Leu Ala Ile Thr Asp Ser Phe
                 85                  90                  95

Thr Gly Leu Ile Asn Ile Leu Thr Asp Ile Ile Trp Arg Phe Thr Gly
            100                 105                 110

Asp Phe Met Ala Pro Asp Leu Val Cys Arg Ile Val Arg Tyr Leu Gln
        115                 120                 125

Val Val Leu Leu Tyr Ala Ser Thr Tyr Val Leu Val Ser Leu Ser Ile
    130                 135                 140

Asp Arg Tyr His Ala Ile Val Tyr Pro Met Lys Phe Leu Gln Gly Glu
145                 150                 155                 160

Lys Gln Ala Lys Val Leu Ile Gly Ile Ala Trp Ser Leu Ser Phe Leu
                165                 170                 175

Phe Ser Ile Pro Thr Leu Ile Ile Phe Gly Lys Arg Thr Leu Ser Asn
            180                 185                 190

Gly Glu Val Gln Cys Trp Ala Leu Trp Pro Asp Asp Ser Tyr Trp Thr
        195                 200                 205

Pro Tyr Met Thr Ile Val Ala Phe Leu Val Tyr Phe Ile Pro Leu Thr
    210                 215                 220

Ile Ile Ser Val Ile Tyr Gly Leu Val Ile Arg Thr Ile Trp Ile Lys
225                 230                 235                 240

Ser Lys Ala His Glu Thr Val Ile Ser Asn Cys Ser Asp Gly Glu Leu
                245                 250                 255
```

```
Cys Cys Ser Tyr Asn Arg Gly Leu Ile Ser Lys Ala Lys Ile Lys Ala
            260                 265                 270

Ile Lys Tyr Ser Ile Val Ile Ile Leu Ala Phe Ile Cys Cys Trp Ser
        275                 280                 285

Pro Tyr Phe Leu Phe Asp Met Leu Asp Asn Phe Asn Leu Leu Pro Asp
    290                 295                 300

Thr Lys Glu Arg Phe Tyr Ala Ser Val Ile Ile Gln Asn Leu Pro Ala
305                 310                 315                 320

Leu Asn Ser Ala Ile Asn Pro Leu Ile Tyr Cys Ile Phe Ser Gly Ser
                325                 330                 335

Leu Cys Ser Pro Cys Lys Val Gln Arg Ser Gln Asp Ser Arg Met Thr
            340                 345                 350

Tyr Arg Glu Arg Ser Glu Arg His Glu Met Gln Ile Leu Ser Lys Pro
        355                 360                 365

Glu Phe Ile
    370
```

<210> SEQ ID NO 65
<211> LENGTH: 1113
<212> TYPE: DNA
<213> ORGANISM: Rat

<400> SEQUENCE: 65

```
atgccggcca acctcacaga gggcagcttt catgccaacc agactgtgcc gatgctagat     60

tcttcccctg tagcttgcac tgaaattgtg actttcactg aagcgctgga ggctgaggag    120

tggggctcct tctactcgtc ctttaagaca gagcagctga taaccctgtg ggtcctgttt    180

gtcttcacta ttgtgggaaa ctcggtcgtg ctgttctcca catggagaag aaaaagaaag    240

tccagaatga ccttctttgt gactcaattg gccatcacag actccttcac aggcctgatc    300

aacatcctga cagacattat ttggcgattc acgggagact tcatggcccc tgacctggtc    360

tgcagaatcg tccgctactt acaggttgtc ctgctttatg cctctaccta tgtcctggtg    420

tccctcagca tagacagata ccatgccatc gtttacccca tgaaattcct tcaaggagag    480

aagcaagcca aagtcctcat cggaatagca tggagcctct ccttcctgtt ctccatcccc    540

acactgatca tatttgggaa aaggacactt tccaatggtg aggtacagtg ctgggcactg    600

tggccagacg actcctactg gaccccatat atgaccatcg ttgcctttct ggtgtacttc    660

atccccttga caattatcag cgtcatctat ggccttgtga tccgaactat ttggattaaa    720

agcaaagccc atgagacggt gatttccaac tgctcagatg gagaactatg ctgcagctac    780

aaccgaggcc tcatctcaaa agcaaaaatc aaggccatca agtacagcat cgtcataatc    840

cttgctttca tctgctgctg gagtccatac ttcctctttg acatgttaga caacttcaac    900

ctccttccag acaccaagga gcgtttctat gcctctgtga ttatccagaa cctgcctgcc    960

ttgaacagtg ccattaaccc cctcatctac tgcatcttca gcggctccct ctgctccccc   1020

tgcaaggtgc aaagatccca ggattccaga atgacgtacc gagagagaag cgagaggcat   1080

gagatgcaga ttctctccaa gcctgaattc atc                                1113
```

<210> SEQ ID NO 66
<211> LENGTH: 36
<212> TYPE: DNA
<213> ORGANISM: Artificial Sequence
<220> FEATURE:
<223> OTHER INFORMATION: Designed oligonucleotide primer to amplify DNA encoding rat TGR23

<400> SEQUENCE: 66
gtcgacatgc cggccaacct cacagagggc agcttt 36

<210> SEQ ID NO 67
<211> LENGTH: 36
<212> TYPE: DNA
<213> ORGANISM: Artificial Sequence
<220> FEATURE:
<223> OTHER INFORMATION: Designed oligonucleotide primer to amplify DNA encoding rat TGR23

<400> SEQUENCE: 67
actagtttag atgaattcag gcttggagag aatctg 36

<210> SEQ ID NO 68
<211> LENGTH: 24
<212> TYPE: DNA
<213> ORGANISM: Artificial Sequence
<220> FEATURE:
<223> OTHER INFORMATION: Primer

<400> SEQUENCE: 68
cttaacaaga acaaaaggcc acag 24

<210> SEQ ID NO 69
<211> LENGTH: 26
<212> TYPE: DNA
<213> ORGANISM: Artificial Sequence
<220> FEATURE:
<223> OTHER INFORMATION: Primer

<400> SEQUENCE: 69
ttattcattg ctttgctctt cgaaat 26

<210> SEQ ID NO 70
<211> LENGTH: 26
<212> TYPE: DNA
<213> ORGANISM: Artificial Sequence
<220> FEATURE:
<223> OTHER INFORMATION: Primer

<400> SEQUENCE: 70
ccacccaagc aggctcagac agcgag 26

<210> SEQ ID NO 71
<211> LENGTH: 353
<212> TYPE: DNA
<213> ORGANISM: Rat

<400> SEQUENCE: 71
ccacccaagc aggctcagac agcgagcgtg aggaatttgg caataaaaac ccatctgcac 60
agatctcgga aaatccaaaa tgattggctc attaaaactc aacctcatct tagctctgtc 120
gctgtccgtg gtacacgtga tttggagtta tccggtcctc tcttccaagg tgcctgggaa 180
gcctgattac tttctcattt tgctgagtac ctgcccagcc aggctggagg ggagcgacgg 240
gctagctttt ctaaagccaa ttttggagaa gacgtcgatg aaaaggtcct ttcgcaacgg 300
agtcggctca ggggtgaaaa aaacttcatt tcgaagagca aagcaatgaa taa 353

<210> SEQ ID NO 72
<211> LENGTH: 89
<212> TYPE: PRT
<213> ORGANISM: Rat

-continued

```
<400> SEQUENCE: 72

Met Ile Gly Ser Leu Lys Leu Asn Leu Ile Leu Ala Leu Ser Leu Ser
                5                   10                  15

Val Val His Val Ile Trp Ser Tyr Pro Val Leu Ser Ser Lys Val Pro
            20                  25                  30

Gly Lys Pro Asp Tyr Phe Leu Ile Leu Leu Ser Thr Cys Pro Ala Arg
        35                  40                  45

Leu Glu Gly Ser Asp Gly Leu Ala Phe Leu Lys Pro Ile Leu Glu Lys
    50                  55                  60

Thr Ser Met Lys Arg Ser Phe Arg Asn Gly Val Gly Ser Gly Val Lys
65                  70                  75                  80

Lys Thr Ser Phe Arg Arg Ala Lys Gln
                    85
```